US012678168B2

(12) United States Patent
Privitera et al.

(10) Patent No.: US 12,678,168 B2
(45) Date of Patent: Jul. 14, 2026

(54) APPENDAGE CLAMP DEPLOYMENT ASSIST DEVICE

(71) Applicant: AtriCure, Inc., Mason, OH (US)

(72) Inventors: Salvatore Privitera, Mason, OH (US);
Matthew Monti, Cincinnati, OH (US);
Adam Harp, Cincinnati, OH (US);
Kenneth Miller, Hamilton, OH (US);
Jason Glithero, McDonough, GA (US)

(73) Assignee: AtriCure, Inc., Mason, OH (US)

( * ) Notice: Subject to any disclaimer, the term of this patent is extended or adjusted under 35 U.S.C. 154(b) by 0 days.

(21) Appl. No.: 18/535,973

(22) Filed: Dec. 11, 2023

(65) Prior Publication Data

US 2024/0130735 A1    Apr. 25, 2024

Related U.S. Application Data

(63) Continuation of application No. 18/342,508, filed on Jun. 27, 2023, now Pat. No. 11,883,035, which is a
(Continued)

(51) Int. Cl.
*A61B 17/122* (2006.01)
*A61B 17/128* (2006.01)
(Continued)

(52) U.S. Cl.
CPC ...... *A61B 17/1227* (2013.01); *A61B 17/1285* (2013.01); *A61B 34/30* (2016.02);
(Continued)

(58) Field of Classification Search
CPC ............ A61B 17/1227; A61B 17/1285; A61B 17/128; A61B 17/122; A61B 2017/12004;
(Continued)

(56) References Cited

U.S. PATENT DOCUMENTS 119,938 A      10/1871  Mellish
1,152,492 A     9/1915  Deming
(Continued)

FOREIGN PATENT DOCUMENTS

EP        1584293 A1    10/2005
EP        1600108 A2    11/2005
(Continued)

OTHER PUBLICATIONS

Final Office Action mailed on Feb. 27, 2024, for U.S. Appl. No. 18/342,519, filed Jun. 27, 2023, 9 pages.
(Continued)

*Primary Examiner* — Diane D Yabut
(74) *Attorney, Agent, or Firm* — Dorton & Willis LLP; Ryan Willis

(57) ABSTRACT

The instant disclosure is directed to devices and methods for deploying a biased occlusion clamp. In addition, the present disclosure includes devices and methods for deploying a biased occlusion clamp using robotics. Moreover, the present disclosure includes devices and methods for reducing the force necessary to open an occlusion clamp without permanently compromising the clamping force of the clamp itself.

20 Claims, 23 Drawing Sheets

Related U.S. Application Data continuation of application No. 16/536,936, filed on Aug. 9, 2019, now Pat. No. 12,178,442, which is a continuation of application No. 14/585,712, filed on Dec. 30, 2014, now Pat. No. 10,433,854, which is a continuation of application No. 13/282,775, filed on Oct. 27, 2011, now Pat. No. 9,017,349.

(60) Provisional application No. 61/407,150, filed on Oct. 27, 2010.

(51) Int. Cl.
*A61B 34/30* (2016.01)
*A61B 17/00* (2006.01)

(52) U.S. Cl.
CPC ............... *A61B 2017/00526* (2013.01); *Y10T 29/49826* (2015.01)

(58) Field of Classification Search
CPC ........ A61F 2/2478; A61F 2/2481; A61F 6/20; A61F 6/202; A61F 6/206; A61F 6/208; A61F 6/204
See application file for complete search history.

(56) References Cited

U.S. PATENT DOCUMENTS

| | | | |
|---|---|---|---|
| 1,162,578 | A | 11/1915 | Forge |
| 1,205,889 | A | 11/1916 | Halvorson |
| 1,357,233 | A | 11/1920 | William |
| 1,491,941 | A | 4/1924 | Wood |
| 1,684,721 | A | 9/1928 | Wood |
| 2,051,174 | A | 8/1936 | Martin |
| 2,060,724 | A | 11/1936 | Carroll |
| 2,371,978 | A | 3/1945 | Perham |
| 2,384,697 | A | 9/1945 | Peter |
| 2,540,722 | A | 2/1951 | Gardner |
| 2,593,201 | A | 4/1952 | Saunders |
| 2,815,557 | A | 12/1957 | Jorgensen |
| 3,032,039 | A | 5/1962 | Beaty |
| 3,496,932 | A | 2/1970 | Prisk et al. |
| 3,503,396 | A | 3/1970 | Pierie et al. |
| 3,503,398 | A | 3/1970 | Fogarty et al. |
| 3,579,751 | A | 5/1971 | Jonckheere |
| 3,682,180 | A | 8/1972 | Mcfarlane |
| 3,818,784 | A | 6/1974 | Mc |
| 3,854,482 | A | 12/1974 | Laugherty et al. |
| 3,856,016 | A | 12/1974 | Davis |
| 3,856,017 | A | 12/1974 | Chancholle et al. |
| 3,856,018 | A | 12/1974 | Perisse et al. |
| 3,954,108 | A | 5/1976 | Davis |
| 4,120,302 | A | 10/1978 | Ziegler |
| 4,226,239 | A | 10/1980 | Polk et al. |
| 4,231,360 | A | 11/1980 | Zloczysti et al. |
| 4,274,415 | A | 6/1981 | Kanamoto et al. |
| 4,428,374 | A | 1/1984 | Auburn |
| 4,493,319 | A | 1/1985 | Polk et al. |
| 4,552,128 | A | 11/1985 | Haber |
| RE32,269 | E | 10/1986 | Bisk et al. |
| 4,716,634 | A | 1/1988 | Fan |
| 4,788,966 | A | 12/1988 | Yoon |
| 4,791,707 | A | 12/1988 | Tucker |
| 4,821,719 | A | 4/1989 | Fogarty |
| 4,869,268 | A | 9/1989 | Yoon |
| 4,917,677 | A | 4/1990 | McCarthy |
| 4,950,284 | A | 8/1990 | Green et al. |
| 5,026,379 | A | 6/1991 | Yoon |
| 5,063,645 | A | 11/1991 | Crespo |
| 5,075,935 | A | 12/1991 | Abdi |
| 5,100,416 | A | 3/1992 | Oh et al. |
| 5,108,420 | A | 4/1992 | Marks |
| 5,119,804 | A | 6/1992 | Anstadt |
| 5,171,250 | A | 12/1992 | Yoon |
| 5,171,252 | A | 12/1992 | Friedland |
| 5,190,541 | A | 3/1993 | Abele et al. |
| 5,217,030 | A | 6/1993 | Yoon |
| 5,217,473 | A | 6/1993 | Yoon |
| 5,258,000 | A | 11/1993 | Gianturco |
| 5,282,811 | A | 2/1994 | Booker et al. |
| 5,282,829 | A | 2/1994 | Hermes |
| 5,282,844 | A | 2/1994 | Stokes et al. |
| 5,290,299 | A | 3/1994 | Fain et al. |
| 5,306,234 | A | 4/1994 | Johnson |
| 5,309,927 | A | 5/1994 | Welch |
| 5,334,209 | A | 8/1994 | Yoon |
| 5,336,252 | A | 8/1994 | Cohen |
| 5,342,373 | A | 8/1994 | Stefanchik et al. |
| 5,366,459 | A | 11/1994 | Yoon |
| 5,402,558 | A | 4/1995 | Santapa |
| 5,403,311 | A | 4/1995 | Abele et al. |
| 5,403,343 | A | 4/1995 | Sugarbaker |
| 5,425,740 | A | 6/1995 | Hutchinson, Jr. |
| 5,439,156 | A | 8/1995 | Grant et al. |
| 5,445,167 | A | 8/1995 | Yoon et al. |
| 5,452,733 | A | 9/1995 | Sterman et al. |
| 5,549,628 | A | 8/1996 | Cooper et al. |
| 5,575,795 | A | 11/1996 | Anderson |
| 5,582,616 | A | 12/1996 | Bolduc et al. |
| 5,609,599 | A | 3/1997 | Levin |
| 5,620,452 | A | 4/1997 | Yoon |
| 5,634,932 | A | 6/1997 | Schmidt |
| 5,643,255 | A | 7/1997 | Organ |
| 5,643,291 | A | 7/1997 | Pier et al. |
| 5,653,720 | A | 8/1997 | Johnson et al. |
| 5,665,100 | A | 9/1997 | Yoon |
| 5,667,518 | A | 9/1997 | Pannell |
| 5,676,636 | A | 10/1997 | Chin |
| 5,681,330 | A | 10/1997 | Hughett et al. |
| 5,683,405 | A | 11/1997 | Yacoubian et al. |
| 5,695,505 | A | 12/1997 | Yoon |
| 5,702,411 | A | 12/1997 | Back et al. |
| 5,707,377 | A | 1/1998 | Keller et al. |
| 5,709,224 | A | 1/1998 | Behl et al. |
| 5,727,569 | A | 3/1998 | Benetti et al. |
| 5,728,121 | A | 3/1998 | Bimbo et al. |
| 5,733,295 | A | 3/1998 | Back et al. |
| 5,735,848 | A | 4/1998 | Yates et al. |
| 5,758,420 | A | 6/1998 | Schmidt et al. |
| 5,762,255 | A | 6/1998 | Chrisman et al. |
| 5,766,217 | A | 6/1998 | Christy |
| 5,782,397 | A | 7/1998 | Koukline |
| 5,782,844 | A | 7/1998 | Yoon et al. |
| 5,797,960 | A | 8/1998 | Stevens et al. |
| 5,810,851 | A | 9/1998 | Yoon |
| 5,810,882 | A | 9/1998 | Bolduc et al. |
| 5,823,956 | A | 10/1998 | Roth et al. |
| 5,824,008 | A | 10/1998 | Bolduc et al. |
| 5,827,216 | A | 10/1998 | Igo et al. |
| 5,827,306 | A | 10/1998 | Yoon |
| 5,830,221 | A | 11/1998 | Stein et al. |
| 5,833,700 | A | 11/1998 | Fogelberg et al. |
| 5,843,101 | A | 12/1998 | Fry |
| 5,843,121 | A | 12/1998 | Yoon |
| 5,843,152 | A | 12/1998 | Tu et al. |
| 5,849,019 | A | 12/1998 | Yoon |
| 5,865,791 | A | 2/1999 | Whayne et al. |
| 5,891,162 | A | 4/1999 | Sugarbaker et al. |
| 5,893,863 | A | 4/1999 | Yoon |
| 5,919,202 | A | 7/1999 | Yoon |
| 5,921,997 | A | 7/1999 | Fogelberg et al. |
| 5,922,001 | A | 7/1999 | Yoon |
| 5,922,002 | A | 7/1999 | Yoon |
| 5,964,772 | A | 10/1999 | Bolduc et al. |
| 5,984,917 | A | 11/1999 | Fleischman et al. |
| 5,984,938 | A | 11/1999 | Yoon |
| 5,984,939 | A | 11/1999 | Yoon |
| 6,007,552 | A | 12/1999 | Fogarty et al. |
| 6,016,452 | A | 1/2000 | Kasevich |
| 6,019,722 | A | 2/2000 | Spence et al. |
| 6,023,818 | A | 2/2000 | Shang |
| 6,042,563 | A | 3/2000 | Morejohn et al. |
| 6,045,571 | A | 4/2000 | Hill et al. |
| 6,074,418 | A | 6/2000 | Buchanan et al. |

(56)                    References Cited

U.S. PATENT DOCUMENTS

| | | |
|---|---|---|
| 6,077,261 A | 6/2000 | Behl et al. |
| 6,080,173 A | 6/2000 | Williamson, IV et al. |
| 6,088,889 A | 7/2000 | Luther et al. |
| 6,096,052 A | 8/2000 | Callister et al. |
| 6,099,539 A | 8/2000 | Howell et al. |
| 6,099,550 A | 8/2000 | Yoon |
| 6,152,144 A | 11/2000 | Lesh et al. |
| 6,152,936 A | 11/2000 | Christy et al. |
| 6,161,543 A | 12/2000 | Cox et al. |
| 6,165,183 A | 12/2000 | Kuehn et al. |
| 6,179,850 B1 | 1/2001 | Goradia |
| 6,193,732 B1 | 2/2001 | Frantzen et al. |
| 6,203,541 B1 | 3/2001 | Keppel |
| 6,231,561 B1 | 5/2001 | Frazier et al. |
| 6,237,605 B1 | 5/2001 | Vaska et al. |
| 6,241,727 B1 | 6/2001 | Tu et al. |
| 6,248,124 B1 | 6/2001 | Pedros et al. |
| 6,258,105 B1 | 7/2001 | Hart et al. |
| 6,270,516 B1 | 8/2001 | Tanner et al. |
| 6,277,065 B1 | 8/2001 | Donofrio |
| 6,280,415 B1 | 8/2001 | Johnson |
| 6,290,674 B1 | 9/2001 | Roue et al. |
| 6,296,656 B1 | 10/2001 | Bolduc et al. |
| 6,299,612 B1 | 10/2001 | Ouchi |
| 6,312,447 B1 | 11/2001 | Grimes |
| 6,315,715 B1 | 11/2001 | Taylor et al. |
| 6,322,494 B1 | 11/2001 | Bullivant et al. |
| 6,328,688 B1 | 12/2001 | Borst et al. |
| 6,330,964 B1 | 12/2001 | Kayan et al. |
| 6,334,843 B1 | 1/2002 | Borst et al. |
| 6,336,898 B1 | 1/2002 | Borst et al. |
| 6,340,344 B1 | 1/2002 | Christopher |
| 6,357,100 B2 | 3/2002 | Speller, Jr. et al. |
| 6,387,105 B1 | 5/2002 | Gifford, III et al. |
| 6,402,765 B1 | 6/2002 | Monassevitch et al. |
| 6,416,554 B1 | 7/2002 | Alferness et al. |
| 6,428,548 B1 | 8/2002 | Durgin et al. |
| 6,436,088 B2 | 8/2002 | Frazier et al. |
| 6,447,542 B1 | 9/2002 | Weadock |
| 6,450,391 B1 | 9/2002 | Kayan et al. |
| 6,464,700 B1 | 10/2002 | Koblish et al. |
| 6,465,196 B1 | 10/2002 | Hobbs et al. |
| 6,485,407 B2 | 11/2002 | Alferness et al. |
| 6,488,689 B1 | 12/2002 | Kaplan et al. |
| 6,491,701 B2 | 12/2002 | Tierney et al. |
| 6,491,706 B1 | 12/2002 | Alferness et al. |
| 6,494,211 B1 | 12/2002 | Boyd et al. |
| 6,506,149 B2 | 1/2003 | Peng et al. |
| 6,508,829 B1 | 1/2003 | Levinson et al. |
| 6,514,265 B2 | 2/2003 | Ho et al. |
| 6,520,974 B2 | 2/2003 | Tanner et al. |
| 6,562,051 B1 | 5/2003 | Bolduc et al. |
| 6,578,585 B1 | 6/2003 | Stachowski et al. |
| 6,579,304 B1 * | 6/2003 | Hart ........................ A61B 17/02 |
| | | 606/205 |
| 6,584,360 B2 | 6/2003 | Francischelli et al. |
| 6,607,504 B2 | 8/2003 | Haarala et al. |
| 6,607,542 B1 | 8/2003 | Wild |
| 6,610,074 B2 | 8/2003 | Santilli |
| 6,645,196 B1 | 11/2003 | Nixon et al. |
| 6,652,515 B1 | 11/2003 | Maguire et al. |
| 6,666,861 B1 | 12/2003 | Grabek |
| 6,676,684 B1 | 1/2004 | Morley et al. |
| 6,679,268 B2 | 1/2004 | Stevens et al. |
| 6,701,929 B2 | 3/2004 | Hussein |
| 6,709,442 B2 | 3/2004 | Miller et al. |
| 6,712,804 B2 | 3/2004 | Roue et al. |
| 6,719,767 B1 | 4/2004 | Kimblad |
| 6,746,461 B2 | 6/2004 | Fry |
| 6,770,081 B1 | 8/2004 | Cooper et al. |
| 6,793,664 B2 | 9/2004 | Mazzocchi et al. |
| 6,849,075 B2 | 2/2005 | Bertolero et al. |
| 6,849,078 B2 | 2/2005 | Durgin et al. |
| 6,872,210 B2 | 3/2005 | Hearn |
| 6,896,684 B2 | 5/2005 | Monassevitch et al. |
| 6,911,032 B2 | 6/2005 | Jugenheimer et al. |
| 6,955,175 B2 | 10/2005 | Stevens et al. |
| 6,955,643 B2 | 10/2005 | Gellman et al. |
| 6,960,218 B2 | 11/2005 | Rennich |
| 6,981,628 B2 | 1/2006 | Wales |
| 7,008,401 B2 | 3/2006 | Thompson et al. |
| 7,011,669 B2 | 3/2006 | Kimblad |
| 7,033,378 B2 | 4/2006 | Smith et al. |
| 7,044,134 B2 | 5/2006 | Khairkhahan et al. |
| 7,056,294 B2 | 6/2006 | Khairkhahan et al. |
| 7,077,851 B2 | 7/2006 | Lutze et al. |
| 7,113,831 B2 | 9/2006 | Hooven |
| 7,118,582 B1 | 10/2006 | Wang et al. |
| 7,169,164 B2 | 1/2007 | Borillo et al. |
| 7,207,997 B2 | 4/2007 | Shipp et al. |
| 7,209,783 B2 | 4/2007 | Fellows et al. |
| 7,226,458 B2 | 6/2007 | Kaplan et al. |
| 7,250,195 B1 | 7/2007 | Storey et al. |
| 7,318,829 B2 | 1/2008 | Kaplan et al. |
| 7,344,543 B2 | 3/2008 | Sra |
| 7,424,965 B2 | 9/2008 | Racenet et al. |
| 7,473,261 B2 | 1/2009 | Rennich |
| 7,527,634 B2 | 5/2009 | Zenati et al. |
| 7,572,266 B2 | 8/2009 | Young et al. |
| 7,644,848 B2 | 1/2010 | Swayze et al. |
| 7,862,571 B2 | 1/2011 | Dennis |
| 7,881,762 B2 | 2/2011 | Kling et al. |
| 7,892,244 B2 | 2/2011 | Monassevitch et al. |
| 7,896,895 B2 | 3/2011 | Boudreaux et al. |
| 8,172,870 B2 | 5/2012 | Shipp |
| 8,201,310 B1 | 6/2012 | Abdi et al. |
| 8,313,508 B2 | 11/2012 | Belson et al. |
| 8,578,571 B2 | 11/2013 | Schmidt et al. |
| 8,636,754 B2 | 1/2014 | Hughett, Sr. et al. |
| 8,852,218 B2 | 10/2014 | Hughett, Sr. et al. |
| 8,979,876 B2 | 3/2015 | Kassab et al. |
| 9,017,349 B2 | 4/2015 | Privitera et al. |
| 9,089,391 B2 | 7/2015 | Kassab et al. |
| 9,393,023 B2 | 7/2016 | Privitera et al. |
| 9,737,213 B1 | 8/2017 | Heaton, II et al. |
| 9,883,863 B2 | 2/2018 | Hughett, Sr. et al. |
| 9,901,351 B2 | 2/2018 | Winkler et al. |
| 10,166,024 B2 | 1/2019 | Williamson, IV et al. |
| 10,433,854 B2 * | 10/2019 | Miller ................ A61B 17/1285 |
| 10,898,204 B2 | 1/2021 | Winkler et al. |
| 11,266,413 B2 | 3/2022 | Winkler et al. |
| 11,471,161 B2 | 10/2022 | Hughett, Sr. et al. |
| 11,883,035 B2 * | 1/2024 | Privitera ............ A61B 17/1285 |
| 11,911,042 B2 | 2/2024 | Winkler et al. |
| 2001/0005787 A1 | 6/2001 | Oz et al. |
| 2001/0029384 A1 | 10/2001 | Nicholas et al. |
| 2001/0039419 A1 | 11/2001 | Francischelli et al. |
| 2001/0039434 A1 | 11/2001 | Frazier et al. |
| 2001/0039435 A1 | 11/2001 | Roue et al. |
| 2002/0013605 A1 | 1/2002 | Bolduc et al. |
| 2002/0022860 A1 | 2/2002 | Borillo et al. |
| 2002/0026214 A1 | 2/2002 | Tanner et al. |
| 2002/0026216 A1 | 2/2002 | Grimes |
| 2002/0032454 A1 | 3/2002 | Durgin et al. |
| 2002/0035374 A1 | 3/2002 | Borillo et al. |
| 2002/0049457 A1 | 4/2002 | Kaplan et al. |
| 2002/0055750 A1 | 5/2002 | Durgin et al. |
| 2002/0058967 A1 | 5/2002 | Jervis |
| 2002/0062130 A1 | 5/2002 | Jugenheimer et al. |
| 2002/0065524 A1 | 5/2002 | Miller et al. |
| 2002/0077660 A1 | 6/2002 | Kayan et al. |
| 2002/0099390 A1 | 7/2002 | Kaplan et al. |
| 2002/0103492 A1 | 8/2002 | Kaplan et al. |
| 2002/0111637 A1 | 8/2002 | Kaplan et al. |
| 2002/0111641 A1 | 8/2002 | Peterson et al. |
| 2002/0111643 A1 | 8/2002 | Herrmann et al. |
| 2002/0111647 A1 | 8/2002 | Khairkhahan et al. |
| 2002/0169377 A1 | 11/2002 | Khairkhahan et al. |
| 2002/0177859 A1 | 11/2002 | Monassevitch et al. |
| 2002/0177862 A1 | 11/2002 | Aranyi et al. |
| 2002/0183768 A1 | 12/2002 | Deem et al. |
| 2003/0009441 A1 | 1/2003 | Holsten et al. |
| 2003/0018362 A1 | 1/2003 | Fellows et al. |
| 2003/0023248 A1 | 1/2003 | Parodi |

(56) References Cited

U.S. PATENT DOCUMENTS

| | | | |
|---|---|---|---|
| 2003/0023266 A1 | 1/2003 | Borillo et al. | |
| 2003/0055422 A1 | 3/2003 | Lesh | |
| 2003/0083677 A1 | 5/2003 | Damarati | |
| 2003/0158464 A1 | 8/2003 | Bertolero | |
| 2004/0030335 A1 | 2/2004 | Zenati et al. | |
| 2004/0064138 A1 | 4/2004 | Grabek | |
| 2004/0073241 A1 | 4/2004 | Barry et al. | |
| 2004/0097982 A1 | 5/2004 | Jugenheimer et al. | |
| 2004/0215216 A1 | 10/2004 | Gannoe et al. | |
| 2005/0021062 A1 | 1/2005 | Dennis | |
| 2005/0085808 A1 | 4/2005 | Nakao | |
| 2005/0149068 A1 | 7/2005 | Williams et al. | |
| 2005/0149069 A1 | 7/2005 | Bertolero et al. | |
| 2005/0203561 A1 | 9/2005 | Palmer et al. | |
| 2005/0240219 A1 | 10/2005 | Kahle et al. | |
| 2005/0251183 A1 | 11/2005 | Buckman et al. | |
| 2005/0277959 A1 | 12/2005 | Cosgrove et al. | |
| 2006/0020271 A1 | 1/2006 | Stewart et al. | |
| 2006/0084974 A1 | 4/2006 | Privitera et al. | |
| 2006/0100646 A1 | 5/2006 | Hart et al. | |
| 2006/0100649 A1 | 5/2006 | Hart | |
| 2006/0161147 A1 | 7/2006 | Privitera et al. | |
| 2006/0161149 A1 | 7/2006 | Privitera et al. | |
| 2006/0212049 A1 | 9/2006 | Mohiuddin | |
| 2006/0229594 A1 | 10/2006 | Francischelli et al. | |
| 2006/0253129 A1 | 11/2006 | Liddicoat et al. | |
| 2006/0271089 A1 | 11/2006 | Alejandro et al. | |
| 2007/0016228 A1 | 1/2007 | Salas | |
| 2007/0021761 A1 | 1/2007 | Phillips | |
| 2007/0027456 A1 | 2/2007 | Gartner et al. | |
| 2007/0032807 A1 | 2/2007 | Ortiz et al. | |
| 2007/0149988 A1 | 6/2007 | Michler et al. | |
| 2007/0149989 A1 | 6/2007 | Santilli et al. | |
| 2007/0213585 A1 | 9/2007 | Monassevitch et al. | |
| 2007/0213747 A1 | 9/2007 | Monassevitch et al. | |
| 2008/0004637 A1 | 1/2008 | Klassen et al. | |
| 2008/0033457 A1 | 2/2008 | Francischelli et al. | |
| 2008/0039879 A1 | 2/2008 | Chin et al. | |
| 2008/0125795 A1 | 5/2008 | Kaplan et al. | |
| 2008/0208324 A1 | 8/2008 | Glithero et al. | |
| 2008/0244880 A1 | 10/2008 | Rankin et al. | |
| 2009/0012545 A1* | 1/2009 | Williamson, IV | A61B 17/1227 606/157 |
| 2009/0069823 A1 | 3/2009 | Foerster et al. | |
| 2009/0209986 A1 | 8/2009 | Stewart et al. | |
| 2009/0240266 A1 | 9/2009 | Dennis | |
| 2009/0253961 A1 | 10/2009 | Le et al. | |
| 2010/0004663 A1 | 1/2010 | Murphy et al. | |
| 2010/0114124 A1 | 5/2010 | Kelleher et al. | |
| 2010/0179570 A1* | 7/2010 | Privitera | A61B 17/122 606/157 |
| 2010/0204716 A1 | 8/2010 | Stewart et al. | |
| 2010/0298849 A1 | 11/2010 | Lazic | |
| 2011/0046437 A1 | 2/2011 | Kassab et al. | |
| 2011/0046641 A1 | 2/2011 | Kassab et al. | |
| 2011/0152922 A1 | 6/2011 | Jeong | |
| 2011/0224700 A1 | 9/2011 | Schmidt et al. | |
| 2011/0288571 A1 | 11/2011 | Steinhilper et al. | |
| 2011/0313437 A1 | 12/2011 | Yeh | |
| 2012/0035622 A1 | 2/2012 | Kiser et al. | |
| 2012/0035631 A1 | 2/2012 | Hughett, Sr. et al. | |
| 2012/0109161 A1 | 5/2012 | Privitera et al. | |
| 2012/0149990 A1 | 6/2012 | Buehler et al. | |
| 2014/0058411 A1 | 2/2014 | Soutorine et al. | |
| 2014/0142597 A1 | 5/2014 | Winkler et al. | |
| 2014/0172084 A1 | 6/2014 | Callas et al. | |
| 2014/0358168 A1 | 12/2014 | Hughett, Sr. et al. | |
| 2015/0057684 A1 | 2/2015 | Zieris | |
| 2015/0374380 A1 | 12/2015 | Miller et al. | |
| 2016/0008001 A1 | 1/2016 | Winkler et al. | |
| 2018/0199944 A1 | 7/2018 | Hughett, Sr. et al. | |
| 2018/0317922 A1 | 11/2018 | Winkler et al. | |
| 2019/0357912 A1 | 11/2019 | Privitera et al. | |
| 2021/0106336 A1 | 4/2021 | Winkler et al. | |
| 2023/0009892 A1 | 1/2023 | Winkler et al. | |
| 2023/0023804 A1 | 1/2023 | Hughett, Sr. et al. | |
| 2023/0338031 A1 | 10/2023 | Winkler et al. | |
| 2023/0338032 A1 | 10/2023 | Winkler et al. | |
| 2023/0338033 A1 | 10/2023 | Winkler et al. | |
| 2023/0338040 A1 | 10/2023 | Winkler et al. | |
| 2023/0338041 A1 | 10/2023 | Winkler et al. | |
| 2023/0338043 A1 | 10/2023 | Privitera et al. | |
| 2023/0389928 A1 | 12/2023 | Hughett et al. | |

FOREIGN PATENT DOCUMENTS

| | | |
|---|---|---|
| WO | WO-9315791 A1 | 8/1993 |
| WO | WO-9818389 A1 | 5/1998 |
| WO | WO-9824488 A2 | 6/1998 |
| WO | WO-9913785 A1 | 3/1999 |
| WO | WO-9913936 A1 | 3/1999 |
| WO | WO-9962409 A1 | 12/1999 |
| WO | WO-0135832 A2 | 5/2001 |
| WO | WO-0197696 A1 | 12/2001 |
| WO | WO-03011150 A1 | 2/2003 |
| WO | WO-03096881 A2 | 11/2003 |
| WO | WO-2006009729 A2 | 1/2006 |
| WO | WO-2007009099 A2 | 1/2007 |
| WO | WO-2007019268 A2 | 2/2007 |
| WO | WO-2006009729 A3 | 5/2007 |
| WO | WO-2007093198 A1 | 8/2007 |
| WO | WO-2007102152 A2 | 9/2007 |
| WO | WO-2007127664 A1 | 11/2007 |
| WO | WO-2010011661 A1 | 1/2010 |
| WO | WO-2013025841 A1 | 2/2013 |
| WO | WO-2013110089 A1 | 7/2013 |
| WO | WO-2015077528 A1 | 5/2015 |
| WO | WO-2016094647 A1 | 6/2016 |

OTHER PUBLICATIONS

Notice of Allowance mailed on Nov. 2, 2023, for U.S. Appl. No. 17/131,975, filed Dec. 23, 2020, 12 pages.

Notice of Allowance mailed on Oct. 20, 2023, for U.S. Appl. No. 17/676,516, filed Feb. 21, 2022, 15 pages.

Al-Saady et al., "Left atrial appendage: structure, function, and role in thromboembolism" Heart (1999) 82:547-555, St. George's Hosp Med School, London UK.

Aytac et al., "Intrapericardial aneurysm of the left atrial appendix" J. Cardiovas. Surg., 21, 1980, pp. 509-511.

Blackshear, J.L. et al., (Feb. 1996). "Appendage Obliteration to Reduce Stroke in Cardiac Surgical Patients With Atrial Fibrillation," Ann. Thorac. Surg. 61(2), 755-9, 13 pages.

Blackshear, J.L. et al., (Oct. 1, 2003). "Thorascopic Extracardiac Obliteration of the Left Atrial Appendage for Stroke Risk Reduction in Atrial Fibrillation," J. Am. Coll. Cardiol. 42(7):1249-1252.

Burke, R.P. et al., (1992). "Improved Surgical Approach to Left Atrial Appendage Aneurysm," Journal of Cardiac Surgery 7(2):104-107.

Coffin, L.H. (Jun. 1985). "Use of the Surgical Stapler to Obliterate the Left Atrial Appendage," Surgery, Gynecology & Obstetric 160:565-566.

Cohn et al., "Right thoracotomy, femorofemoral bypass, and deep hypothermia for re- replacement of the mitral valve" Ann Thorac Surg (1989) 48:69-71, © 1989 Society of Thoracic Surgeons, USA.

Coselli et al., "Congenital intrapericardial aneurysmal dilatation of the left atrial appendage", Case Reports: The Annals of Thoracic Surgery, vol. 39, No. 5, May 1985, pp. 466-468.

Cox et al., "Five-Year Experience with the Maze Procedure for Atrial Fibrillation" Ann Thorac Surg (1993) 56:814-284.

Crystal et al., "Left Atrial Appendage Occlusion Study (Laaos): A Randomized Clinical Trial of Left Atrial Appendage Occlusion During Routine Coronary Artery Bypass Graft Surgery for Long-term Stroke Prevention," Am Heart J (2003) 145:174-178, © 2003 Mosby, Inc., USA.

Dictionary.com definition for "adjacent" as accessed Oct. 17, 2023; https://www.dictionary.com/browse/adjacent, 5 pages.

Disesa et al., "Ligation of the Left Atrial Appendage Using an Automatic Surgical Stapler" Accepted for publication Jul. 26, 1988,

(56) References Cited

OTHER PUBLICATIONS

Div. of Cardiac Surgery, Brigham and Women's Hospital, Boston, MA., 3 pages.

Examiner's Answer to Appeal Brief mailed on Jan. 28, 2021, for U.S. Appl. No. 15/874,257, filed Jan. 18, 2028, 20 pages.

Final Office Action mailed on Feb. 4, 2013, for U.S. Appl. No. 13/010,509, filed Jan. 20, 2011, 28 pages.

Final Office Action mailed on Jan. 11, 2017, for U.S. Appl. No. 14/462,930, filed Aug. 19, 2014, 13 pages.

Final Office Action mailed on Jun. 22, 2020, for U.S. Appl. No. 15/874,257, filed Jan. 18, 2028, 15 pages.

Final Office Action mailed on Jun. 18, 2021, for U.S. Appl. No. 16/536,936, filed Aug. 9, 2019, 11 pages.

Final Office Action mailed on Jan. 26, 2023, for U.S. Appl. No. 16/536,936, filed Aug. 9, 2019, 18 pages.

Final Office Action mailed on Oct. 2, 2017, for U.S. Appl. No. 14/585,712, filed Dec. 30, 2014, 24 pages.

Final Office Action mailed on Feb. 5, 2019, for U.S. Appl. No. 14/585,712, filed Dec. 30, 2014, 21 pages.

Final Office Action mailed on Aug. 21, 2014, for U.S. Appl. No. 13/282,775, filed Oct. 27, 2011, 7 pages.

Final Office Action mailed on May 27, 2020, for U.S. Appl. No. 15/904,541, filed Feb. 26, 2018, 12 pages.

Final Office Action mailed on Nov. 24, 2015, for U.S. Appl. No. 14/085,836, filed Nov. 21, 2013, 9 pages.

Final Office Action mailed on Dec. 23, 2016, for U.S. Appl. No. 14/085,836, filed Nov. 21, 2013, 9 pages.

Final Office Action mailed on Sep. 5, 2017, for U.S. Appl. No. 14/549,811, filed Nov. 21, 2014, 18 pages.

Final Office Action mailed on Dec. 18, 2018, for U.S. Appl. No. 14/549,811, filed Nov. 21, 2014, 18 pages.

Final Office Action mailed on May 13, 2020, for U.S. Appl. No. 14/549,811, filed Nov. 21, 2014, 19 pages.

Final Office Action mailed on Dec. 22, 2023, for U.S. Appl. No. 18/342,542, filed Jun. 27, 2023, 9 pages.

Fisher, D.C. et al. (Dec. 1998). "Large Gradient Across a Partially Ligated Left Atrial Appendage," Journal of the American Society of Echocardiography 11(12):1163-1165.

Fumoto et al., "A novel device for left atrial appendage exclusion: The third-generation atrial exclusion device" J Thorac Cardiov Surg (2008) 136:1019-27 © 2008 American Association for Thoracic Surgery, USA.

Ganeshakrishnan et al., "Congenital Intrapericardial Aneurysm of the Left-Atrial Appendage" Case Report: Thorac. Cardiovasc. Surgeon (1992) 40(6):382-384.

Garcia-Fernandez, M.A. et al., (Oct. 1, 2003). "Role of Left Atrial Appendage Obliteration in Stroke Reduction in Patients With Mitral Valve Prosthesis," Journal of the American College of Cardiology 42(7):1253-1258.

Gillinov, et al., "Stapled excision of the left atrial appendage" J Thorac Cardiovasc Surg (2005) 129:679-680.

Grundeman et al., "Experimental videothoracoscopic cannulation of the left atrial appendix" Surg Enclose (1993) 7:511-513, © 1993 Springer-Verlag New York, Inc., USA.

Halperin, J.L. et al., (Oct. 1, 2003). "Obliteration of the Left Atrial Appendage for Prevention of Thromboembolism," Journal of the American College of Cardiology 42(7):1259-1261.

Hoit, B.D. et al., (Jan. 1993). "Altered Left Atrial Compliance After Atrial Appendectomy. Influence on Left Atrial and Ventricular Filling," Circulation Research 72(1):167-175.

Hondo et al., "The Role of the Left Atrial Appendage; A vol. Loading Study in Open-chest Dogs" Jpn Heart J, Mar. 1995, pp. 225-234, Japan.

Johnson, W.D. et al. (2000). "The Left Atrial Appendage: Our Most Lethal Human Attachment! Surgical Implications," Euro. J. Cardiothoracic. Surg. 17:718-722.

Kamohara et al., "A novel device for left atrial appendage exclusion" J Thorac Cardiov Surg (2005) 130(6):1639-1644.

Kamohara et al., "Impact of left atrial appendage exclusion on left atrial function" J Thorac Cardiov Surg (2007) 133:174-81, © 2007 American Association for Thoracic Surgery, USA.

Kamohara, K. et al., (Aug. 2006). "Evaluation of a Novel Device for Left Atrial Appendage Exclusion: The Second-generation Atrial Exclusion Device," The Journal of Thoracic and Cardiovascular Surgery 132(2):340-346.

Katz, E.S. et al., (Aug. 2000). "Surgical Left Atrial Appendage Ligation is Frequently Incomplete: A Transesophageal Echocardiographic Study," Journal of the American College of Cardiology 36(2):468-471.

Kaymaz et al., "Location, Size and Morphological Characteristics of Left Atrial Thrombi as Assessed by Echocardiography in Patients with Rheumatic Mitral Valve Disease" Eur. J Echocardiography, vol. 2, Issue 4, Dec. 2001, pp. 270-276, © 2001 The European Society of Cardiology.

Landymore et al., "Staple Closure of the Left Atrial Appendage" The Canadian Journal of Surgery, vol. 27, No. 2, Mar. 1984, pp. 144-145.

Landymore, M.D., R. W., "Stapling of Left Atrial Appendage" to the Editor: Ann Thorac Surg (1989) 47:794. 2 pages.

Lindsay, B.D. (1996). "Obliteration of the Left Atrial Appendage: A Concept Worth Testing," The Annals of Thoracic Surgery 61:515. 1 page.

Lipkin et al., "Aneurysmal dilation of left atrial appendage diagnosed by cross sectional echocardiography and surgically removed" Br Heart J (1985) 53:69-71, National Heart Hospital, London, UK.

Lynch et al., "Recanalization of the Left Atrial Appendage Demonstrated by Transesophageal Echocardiography" Ann Thorac Surg (1997) 63:1774-1775.

Mole et al., "Desmoid Tumour in Thoractomy Scar 5 Years After Excision of a Left Giant Atrial Appendage Aneurysm in Female with a Family History of Gardner's Syndrome" Thorac Cardiovasc Surg 40 (1991) pp. 300-302, © 1992 Georg Thieme Verlag Stuttgart, New York.

Non-Final Office Action mailed on Aug. 17, 2012, for U.S. Appl. No. 13/010,509, filed Jan. 20, 2011, 19 pages.

Non-Final Office Action mailed on Aug. 28, 2013, for U.S. Appl. No. 13/010,509, filed Jan. 20, 2011, 22 pages.

Non-Final Office Action mailed on Apr. 22, 2016, for U.S. Appl. No. 14/462,930, filed Aug. 19, 2014, 14 pages.

Non-Final Office Action mailed on Feb. 24, 2020, for U.S. Appl. No. 15/874,257, filed Jan. 18, 2028, 13 pages.

Non-Final Office Action mailed on Feb. 9, 2021, for U.S. Appl. No. 16/536,936, filed Aug. 9, 2019, 12 pages.

Non-Final Office Action mailed on Jul. 12, 2022, for U.S. Appl. No. 16/536,936, filed Aug. 9, 2019, 13 pages.

Non-Final Office Action mailed on Mar. 13, 2017, for U.S. Appl. No. 14/585,712, filed Dec. 30, 2014, 10 pages.

Non-Final Office Action mailed on May 17, 2018, for U.S. Appl. No. 14/585,712, filed Dec. 30, 2014, 35 pages.

Non-Final Office Action mailed on Feb. 25, 2014, for U.S. Appl. No. 13/282,775, filed Oct. 27, 2011, 10 pages.

Non-Final Office Action mailed on Jan. 17, 2020, for U.S. Appl. No. 15/904,541, filed Feb. 26, 2018, 10 pages.

Non-Final Office Action mailed on Jun. 17, 2015, for U.S. Appl. No. 14/085,836, filed Nov. 21, 2013, 10 pages.

Non-Final Office Action mailed on Aug. 15, 2016, for U.S. Appl. No. 14/085,836, filed Nov. 21, 2013, 7 pages.

Non-Final Office Action mailed on Jun. 27, 2017, for U.S. Appl. No. 14/085,836, filed Nov. 21, 2013, 6 pages.

Non-Final Office Action mailed on Jun. 16, 2023, for U.S. Appl. No. 17/676,516, filed Feb. 21, 2022, 11 pages.

Non-Final Office Action mailed on Feb. 8, 2017, for U.S. Appl. No. 14/549,811, filed Nov. 21, 2014, 18 pages.

Non-Final Office Action mailed on May 2, 2018, for U.S. Appl. No. 14/549,811, filed Nov. 21, 2014, 17 pages.

Non-Final Office Action mailed on Oct. 28, 2019, for U.S. Appl. No. 14/549,811, filed Nov. 21, 2014, 17 pages.

Non-Final Office Action mailed on May 20, 2021, for U.S. Appl. No. 14/549,811, filed Nov. 21, 2014, 20 pages.

Non-Final Office Action mailed on Sep. 8, 2023, for U.S. Appl. No. 18/342,542, filed Jun. 27, 2023, 12 pages.

(56) References Cited

OTHER PUBLICATIONS

Non-Final Office Action mailed on Sep. 11, 2023, for U.S. Appl. No. 18/342,556, filed Jun. 27, 2023, 10 pages.
Non-Final Office Action mailed on Sep. 12, 2023, for U.S. Appl. No. 18/342,566, filed Jun. 27, 2023, 10 pages.
Non-Final Office Action mailed on Oct. 23, 2023, for U.S. Appl. No. 18/342,519, filed Jun. 27, 2023, 11 pages.
Non-Final Office Action mailed on Dec. 1, 2023, for U.S. Appl. No. 18/342,481, filed Jun. 27, 2023, 11 pages.
Non-Final Office Action mailed on Dec. 26, 2023, for U.S. Appl. No. 18/342,556, filed Jun. 27, 2023, 9 pages.
Non-Final Office Action mailed on Jan. 3, 2024, for U.S. Appl. No. 18/342,533, filed Jun. 27, 2023, 7 pages.
Notice of Allowance mailed on Mar. 25, 2014, for U.S. Appl. No. 13/010,509, filed Jan. 20, 2011, 15 pages.
Notice of Allowance mailed on Oct. 20, 2017, for U.S. Appl. No. 14/462,930, filed Aug. 19, 2014, 10 pages.
Notice of Allowance mailed on Jun. 13, 2022, for U.S. Appl. No. 15/874,257, filed Jan. 18, 2028, 8 pages.
Notice of Allowance mailed on May 23, 2019, for U.S. Appl. No. 14/585,712, filed Dec. 30, 2014, 11 pages.
Notice of Allowance mailed on Dec. 11, 2014, for U.S. Appl. No. 13/282,775, filed Oct. 27, 2011, 8 pages.
Notice of Allowance mailed on Sep. 18, 2020, for U.S. Appl. No. 15/904,541, filed Feb. 26, 2018, 8 pages.
Notice of Allowance mailed on Oct. 17, 2017, for U.S. Appl. No. 14/085,836, filed Nov. 21, 2013, 9 pages.
Notice of Allowance mailed on Nov. 10, 2021, for U.S. Appl. No. 14/549,811, filed Nov. 21, 2014, 11 pages.
Notice of Allowance mailed on Oct. 23, 2023, for U.S. Appl. No. 18/342,508, filed Jun. 27, 2023, 8 pages.
Notice of Allowance mailed on Dec. 28, 2023, for U.S. Appl. No. 18/342,566, filed Jun. 27, 2023, 13 pages.
Odell, J.A. et al., (1996). "Thorascopic Obliteration of the Left Atrial Appendage: Potential for Stroke Reduction?" Ann. Thorac. Surg. 61:565-569.
Omari et al., "Effect of right atrial appendectomy on the release of atrial natriuretic hormone" J Thorac Cardiovasc Surg (1991) 102:272-279, USA.
PCT/US2006/027553 Prelim Report W/ Written Opinion Jan. 16, 2008 IDX Medical Ltd, 7 pages.
PCT/US2009/051270 Prelim Rprt on Patbl, Atricure, Inc., Feb. 3, 2011. 7 pages.
PCT/US2012/051002 Intl Search Report W/ Written Opinion Oct. 23, 2012 Atricure, Inc., 10 pages.
Riley et al., "Mitral Valve Repair" CTSNET Experts' Techniques, doc 5729, pp. 1-7, (2004).

Robin et al., "Strangulation of the Left Atrial Appendage through a Congenital Partial Pericardial Defect" CHEST, 67:3, Mar. 1975, pp. 354-355.
Rosenzweig et al., "Thromboembolus from a Ligated Left Atrial Appendage" J Am Soc Echocardiography, vol. 14, pp. 396-398, May 2001, © 2001 American Society of Echocardiography, USA.
Salzberg et al., "Left atrial appendage clip occlusion: Early clinical results" J Thorac Cardiov Surg, (2010) vol. 139, No. 5, pp. 1269-1274.
Salzberg, S.P. et al., (2008). "Surgical Left Atrial Appendage Occlusion: Evaluation of a Novel Device with Magnetic Resonance Imaging," European Journal of Cardiothoracic Surgery 34:766-770.
Stollberger, C. et al., (2007). "Leave the Left Atrial Appendage Untouched for Stroke Prevention!" Journal of Thoracic and Cardiovascular Surgery 134(2):549-550.
Stollberger, C. et al., (Dec. 2003). "Elimination of the Left Atrial Appendage to Prevent Stroke or Embolism ?: Anatomic, Physiologic, and Pathophysiologic Considerations," 124(6):2356-2362.
Stollberger et al., "Is left atrial appendage occlusion useful for prevention of stroke or embolism in atrial fibrillation?" Z Kardiol 91:376-379 (2002).
Stollberger et al., "Stroke Prevention By Means of Left Atrial Appendage Strangulation?" to the Editor: J Thorac Cardiovasc Surg (2010) 140(3): p. 732.
Tabata, T. et al. (Feb. 1, 1998). "Role of Left Atrial Appendage in left Atrial Reservoir Function as Evaluated by Left Atrial Appendage Clamping During Cardiac Surgery," The American Journal of Cardiology 81:327-332.
Thomas, TV, "Left atrial appendage and valve replacement" Am Heart Journal, vol. 84, No. 6, Dec. 1972, pp. 838-839.
Unknown, Endowrist Instruments and Accessories Catalog, Intuitive Surgical, Sunnyvale, California, Sep. 2005. 11 pages.
Unknown, Surgical procedure report to track prior art with regards to a minimally invasive left atrial appendage exclusion, Jan. 1, 2007, USA. 2 pages.
Unknown, "Transesophageal Echocardiographic Correlates of Thromboembolism in High Risk Patients with Nonvalvular Atrial Fibrillation" The American College of Physicians, Apr. 1998, pp. 639-647, © 1998 American College of Physicians, USA.
Veinot et al., "Anatomy of the Normal Left Atrial Appendage: A Quantitative Study of Age-Related Changes in 500 autopsy hearts: implications for echocardiographic examination" Circulation (1997) 96:3112-3115, USA.
Wakabayashi, Md., "Expanded applications of diagnostic and therapeutic thoracoscopy" J. Thorac Cardiovasc Surg (1991) 102:721-723.
Wudel, J.H. et al. (Apr. 3, 2008). "Video-Assisted Epicardial Ablation and left Atrial Appendage Exclusion for Atrial Fibrillation: Extended Follow-Up," The Annals of Thoracic Surgery 85:34-38.

* cited by examiner

APPENDAGE CLAMP DEPLOYMENT ASSIST DEVICE

CROSS REFERENCE TO RELATED APPLICATIONS

This application is a continuation of U.S. application Ser. No. 18/342,508 filed Jun. 27, 2023, which is a continuation of U.S. application Ser. No. 16/536,936 filed Aug. 9, 2019, which is a continuation of U.S. application Ser. No. 14/585, 712 filed Dec. 30, 2014, now U.S. Pat. No. 10,433,854, which is a continuation of U.S. application Ser. No. 13/282, 775, filed Oct. 27, 2011, now U.S. Pat. No. 9,017,349, which claims the benefit of U.S. Provisional Application No. 61/407,150, filed Oct. 27, 2010, the contents of each of which are incorporated herein by reference in their entireties.

RELATED ART

Field of the Invention

The present invention is directed to devices and methods for deploying a biased appendage clamp. More specifically, the present disclosure is directed to devices that overcome the bias of an appendage clamp to facilitate deployment of the clamp in the open position and thereafter release the clamp from the device in order to close the clamp around the desired tissue.

INTRODUCTION TO THE INVENTION

It is a first aspect of the present invention to provide an occlusion device comprising: (a) an occlusion clamp comprising a first beam and a second beam biased toward one another; and, (b) an occlusion clamp deployment device comprising a repositionable frame removably coupled to the occlusion clamp, the repositionable frame comprising a plurality of repositionable links that are mounted to one another and are oriented around the occlusion clamp.

In a more detailed embodiment of the first aspect, the first beam includes a first end coupled to a first end of the second beam by a first occlusion spring, and the first beam includes a second end coupled to a second end of the second beam by a second occlusion spring. In yet another more detailed embodiment, the first beam, the second beam, the first occlusion spring, and the second occlusion spring comprise a continuous loop. In a further detailed embodiment, the plurality of repositionable links include: (i) a first link extending along a length of the first beam; (ii) a second link extending along a length of the second beam; (iii) a first series of links concurrently mounted to the first link and the second link; and, (iv) a second series of links concurrently mounted to the first link and the second link, where the first link, the second link, the first series of links, and the second series of links create a loop around the occlusion clamp, and where the first and second series of links are repositionable with respect to the first link and the second link to vary a spacing between the first and second links. In still a further detailed embodiment, the first series of links comprises at least two links repositionably connected to one another, the second series of links comprises at least two links repositionably connected to one another, and the repositionable frame includes a tether operatively coupled to the first series of links and the second series of links, the tether being repositionable to vary the spacing between the first and second links. In a more detailed embodiment, the deployment device further includes a deployment shaft operatively coupled to the repositionable frame, where the first series of links comprises at least two links repositionably connected to one another, the second series of links comprises at least two links repositionably connected to one another, the repositionable frame includes a tether operatively coupled to the first series of links and the second series of links, the tether being repositionable to vary the spacing between the first and second links, and at least a portion of the tether is threaded through the deployment shaft and repositionable within the deployment shaft.

It is a second aspect of the present invention to provide a method of fabricating an occlusion device, the method comprising mounting an occlusion clamp deployment device to an occlusion clamp, the occlusion clamp comprising a first beam and a second beam biased toward one another, the occlusion clamp deployment device including a counterbias spring biasing the first and second beams of the occlusion clamp away from one another, wherein the biasing of the counterbias spring exerts a force less than a force biasing the first beam and the second beam toward one another.

In a more detailed embodiment of the second aspect, the first beam includes a first end coupled to a first end of the second beam by a first occlusion spring, the first beam includes a second end coupled to a second end of the second beam by a second occlusion spring, and the first beam, the second beam, the first occlusion spring, and the second occlusion spring comprise a continuous loop. In still another more detailed embodiment, the act of mounting the occlusion clamp deployment device to the occlusion clamp includes removably mounting the occlusion clamp deployment device to the occlusion clamp by using a suture to concurrently mount the occlusion clamp deployment device to the occlusion clamp.

It is a third aspect of the present invention to provide an occlusion device comprising: (a) an occlusion clamp comprising a first beam and a second beam biased toward one another; and, (b) an occlusion clamp deployment device including a counterbias spring removably mounted to the occlusion clamp, the counterbias spring biasing the first and second beam of the occlusion clamp away from one another, where the biasing of the counterbias spring exerts a force less than a force biasing the first beam and the second beam toward one another.

In a more detailed embodiment of the third aspect, the first beam includes a first end coupled to a first end of the second beam by a first occlusion spring, and the first beam includes a second end coupled to a second end of the second beam by a second occlusion spring. In still another more detailed embodiment, the counterbias spring comprises a continuous loop that includes a pair of torsion springs coupled to one another by a pair of crosspieces. In a further detailed embodiment, a first crosspiece of the pair of crosspieces is mounted to the first beam of the occlusion clamp, a second crosspiece of the pair of crosspieces is mounted to the second beam of the occlusion clamp, and the pair of torsion springs is laterally outset from the first and second beams. In still a further detailed embodiment, the first beam, the second beam, the first occlusion spring, and the second occlusion spring comprise a continuous loop. In a more detailed embodiment, the counterbias spring includes: (i) a first support; (ii) a second support; (iii) a first coil spring concurrently mounted to and extending between the first and second support; and, (iv) a second coil spring concurrently mounted to and extending between the first and second support. In a more detailed embodiment, a first cable operatively coupled to at least one of the first support and the second support, and the first cable is repositionable to compress at least one of the first and second coils to reduce a distance between the first and second supports. In another more detailed embodiment, the counterbias spring further includes a first cable operatively coupled to at least one of the first support and the second support, the first cable is repositionable to compress the first coil to reduce a first distance between the first and second supports, and a second cable operatively coupled to at least one of the first support and the second support, the second cable is repositionable to compress the second coil to reduce a second distance between the first and second supports. In yet another more detailed embodiment, the first cable is operatively coupled to the second support, the second cable is operatively coupled to the second support, and the first and second cable are mounted to a drum repositionably mounted to the first support.

DETAILED DESCRIPTION

The exemplary embodiments of the present disclosure are described and illustrated below to encompass devices and methods for deploying a biased appendage clamp. Of course, it will be apparent to those of ordinary skill in the art that the embodiments discussed below are exemplary in nature and may be reconfigured without departing from the scope and spirit of the present disclosure. However, for clarity and precision, the exemplary embodiments as discussed below may include optional steps, methods, and features that one of ordinary skill should recognize as not being a requisite to fall within the scope of the present disclosure.

Figure 1A:
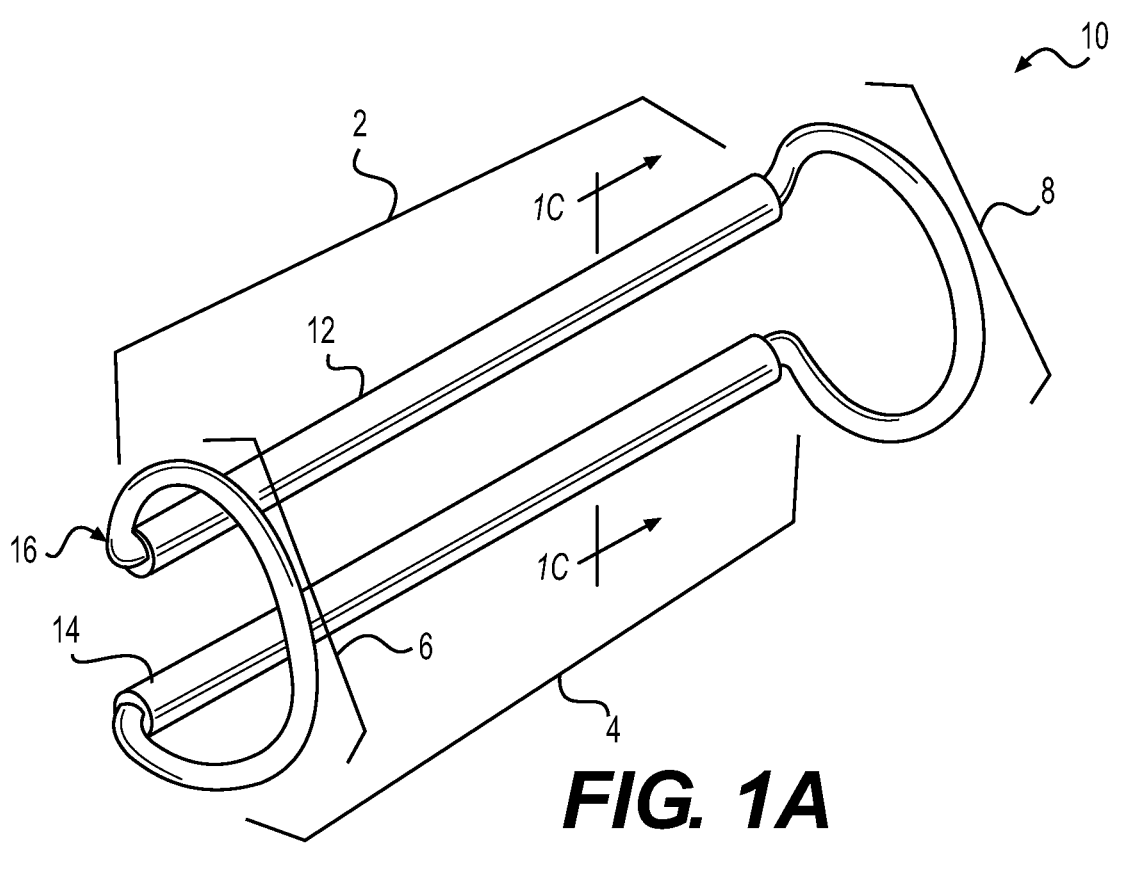
FIG. 1A is an elevated perspective view of an exemplary appendage clamp in the open position.
Figure 1B:
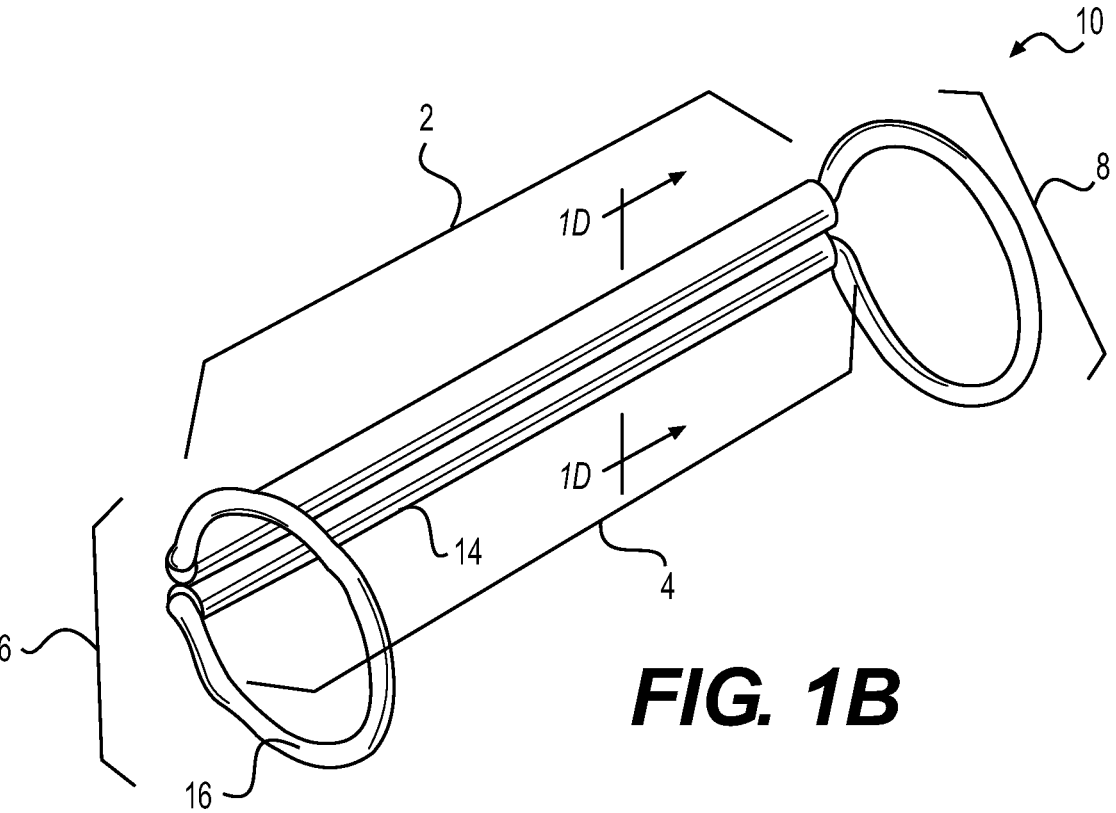
FIG. 1B is an elevated perspective view of the exemplary appendage clamp of FIG. 1 in the closed position.
Figure 1C:
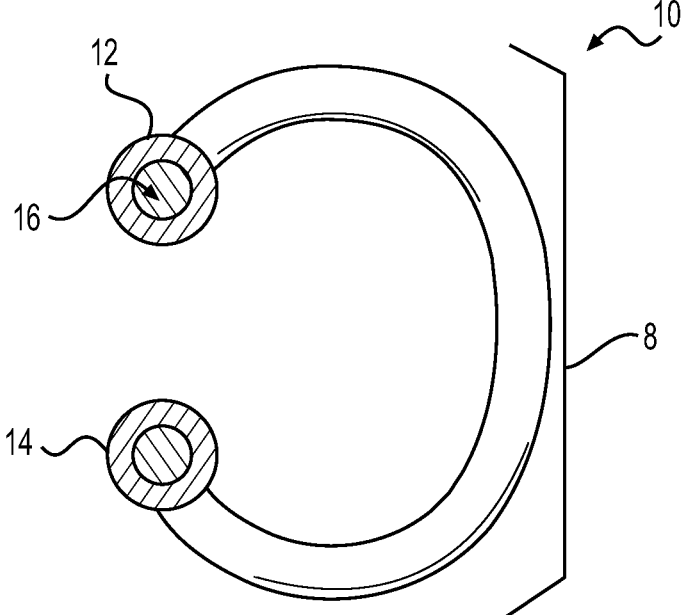
FIG. 1C is a profile view of the exemplary appendage clamp of FIG. 1 in the open position.

FIGS. 1A and 1C show an embodiment of an appendage occlusion clamp 10 in an open position with spaced apart rigid clamping portions 2, 4 and resilient and biased urging members 6, 8 at opposite ends of each clamping portion 2, 4. Clamping portions 2, 4 may be tubular, and both clamping portions 2, 4 may be at least substantially parallel to each other when arrest, i.e., when they are not being used to clamp tissue. Clamping portions 2, 4 may also be of substantially equal length or of different length, and each may be of larger outer diameter than the wire that may be used to form each of the urging members 6, 8. In this regard, the wire forming urging members 6, 8 can extend through the hollow interiors of the clamping portions 2, 4. In this illustrative example, the urging members 6, 8 are each shaped as a loop. The planes defined by the looped configuration of each of the urging members 6, 8 may be substantially parallel to each other and, in turn, substantially perpendicular to each of the clamping portions 2, 4. Of course, other angular orientations are possible as well.

Figure 1D:
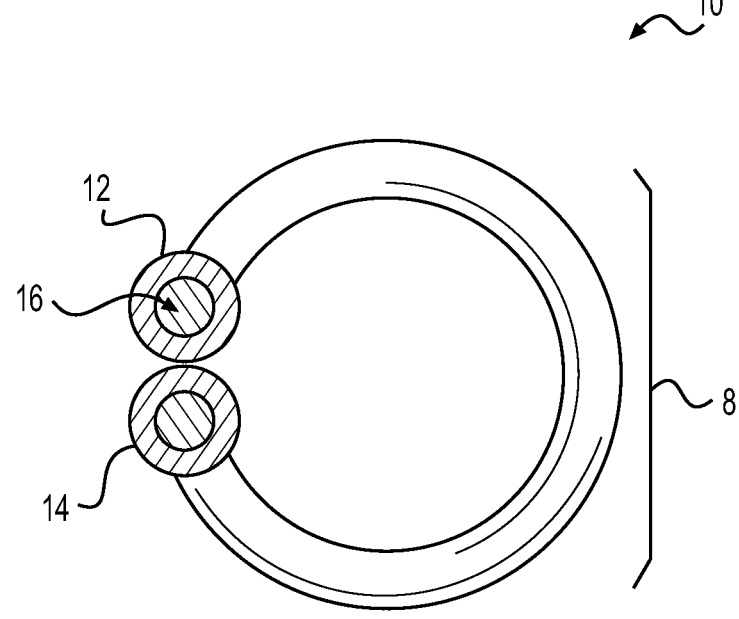
FIG. 1D is a profile view of the exemplary appendage clamp of FIG. 1 in the closed position.
Figure 3:
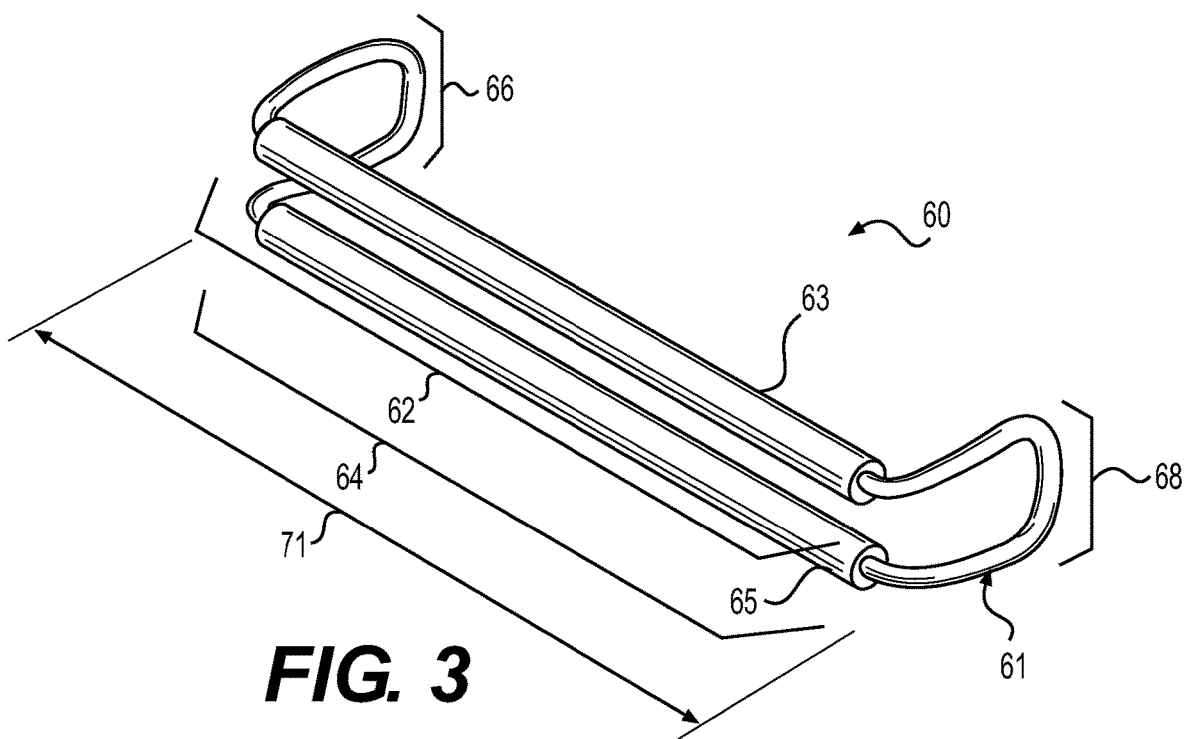
FIG. 3 is an elevated perspective view, from the front, of the exemplary appendage clamp of FIG. 1 without the platens.
Figure 4:
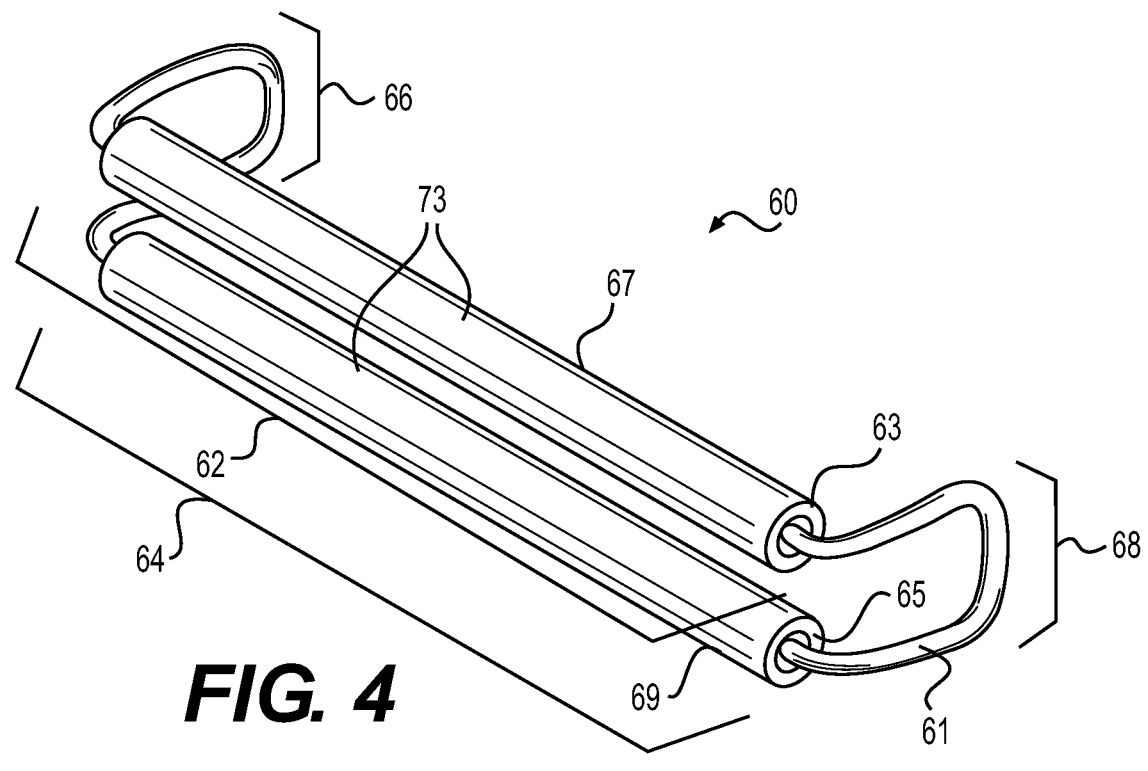
FIG. 4 is an elevated perspective view, from the front, of the exemplary appendage clamp of FIG. 1 with the platens.
Figure 5:
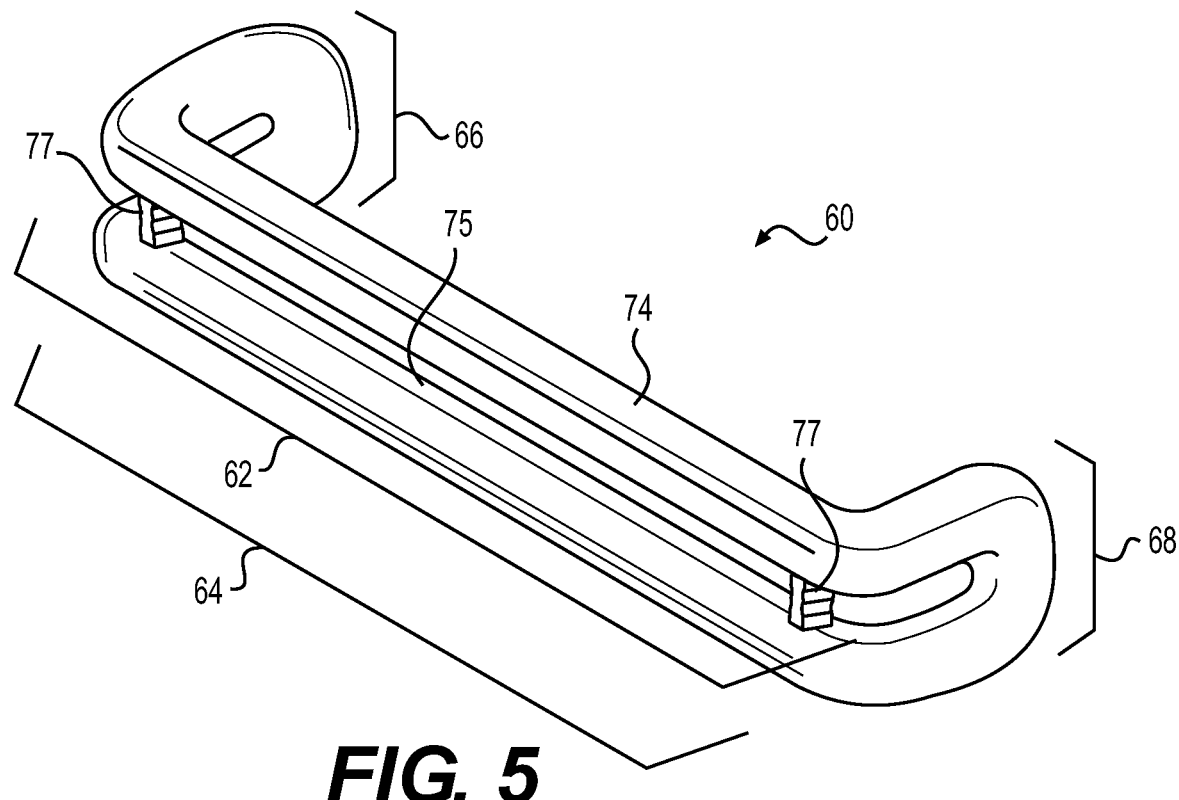
FIG. 5 is an elevated perspective view, from the front, of the exemplary appendage clamp of FIG. 1 with a fabric covering.

FIGS. 1B and 1D show the same clamp 10 of FIGS. 1A and 1C with the clamping portions 2, 4 in their normally biased together positions. Contact between the clamping portions 2, 4 may occur initially along their entire parallel lengths as shown. Of course, when clamping portions 2, 4 are covered in fabric or other material as later described, contact may occur between the fabric or other material that interposes the clamping portions 2, 4. In FIGS. 1A-1D, only the structure and relative positions of the rigid members 2, 4 and urging members 6, 8 are shown. The final assembly is depicted in FIGS. 3, 4 and 5 which, although describing a slightly different embodiment, show the general steps in the construction of each embodiment.

The clamping portions 2, 4 may be made from tubes 12, 14 fabricated from a metal such as titanium disposed over a wire member 16. It should also be understood that the tubes 12, 14 may be fabricated from other metals and other materials such as, without limitation, ceramics and plastics. In this exemplary embodiment, titanium is used for its compatibility with MRI imaging, its biocompatibility and its galvanic compatibility with the wire member 16 when the wire member 16 is formed from superelastic materials such as a nickel titanium alloy.

This embodiment and the other embodiments disclosed herein may use a superelastic material such as a nickel titanium alloy to form the urging members 6, 8. Superelastic properties will allow the material to be greatly extended to open the clamping portions 6, 8 of the clamp 10 without permanently deforming the material. These superelastic materials can also be compatible with MRI imaging and easily tolerated as an implant material in the body.

The rigid tubular members 12, 14 of this embodiment are mechanically fastened to the underlying wire member 16 preferably by mechanically swaging the titanium tubes 12, 14 to the wire members 16. Although a single, continuous wire member is shown directed through both clamping portions 2, 4 and urging members 6, 8, the clamp 10 of this embodiment may also be made with two or more wires, or with any other suitable components.

Figure 2:
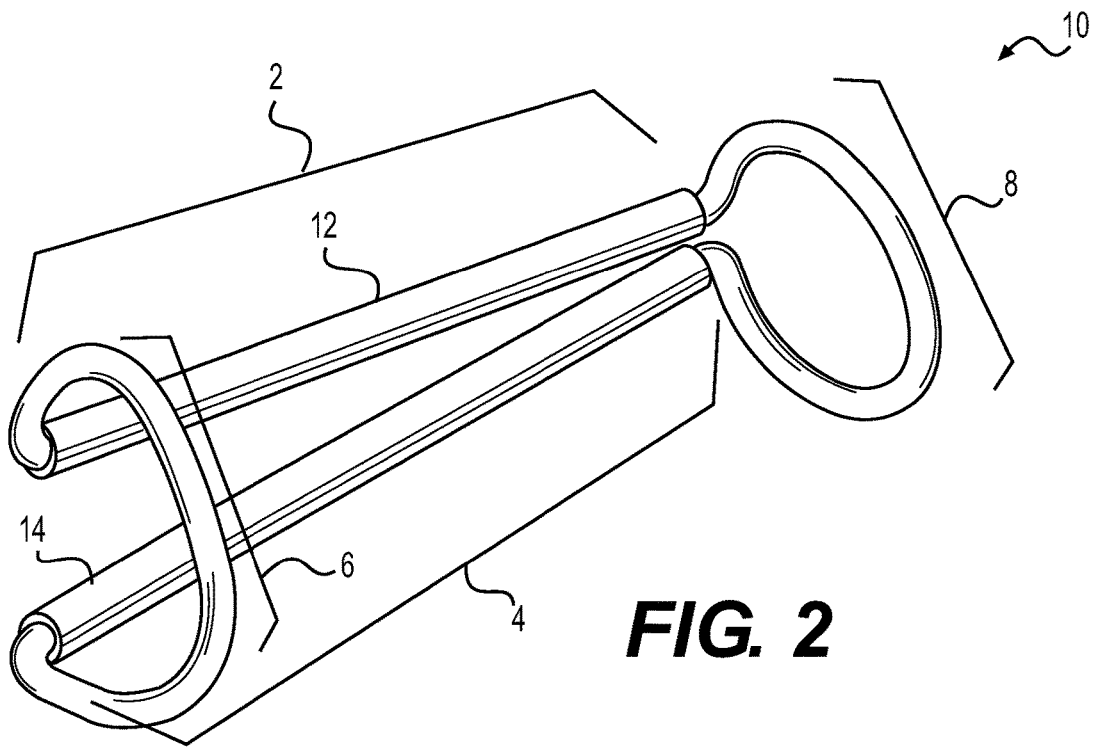
FIG. 2 is an elevated perspective view of the exemplary appendage clamp of FIG. 1 in a partially open position.

As shown in FIG. 2, in addition to being able to close on tissue or anatomical structure in a parallel fashion, the clamp 10 can also apply force to the anatomical structure in a nonparallel clamping fashion. This allows the clamp 10 to accommodate non-uniform tissue thickness over the length of the clamping portions 2, 4. In addition, with separate urging members 6, 8 at opposite ends of the clamping portions 2, 4 the nonparallel clamping can originate from either side of the clamp 10. The non-parallel clamping feature of this embodiment allows the clamp 10 to accommodate a wide range of hollow anatomical structures with varying wall thicknesses throughout its length and breadth. For example, some anatomical structures such as atrial appendages 40 (not shown) of the heart have internal structures called trabeculae, which are non-uniform and very often cause variable thicknesses across one or more of their dimensions. Nonuniform clamping, therefore, can be advantageous in this application for this reason or for other reasons.

FIG. 3 shows an alternate embodiment of a clamp 60 including two urging members 66, 68 shaped to resemble a letter "U" instead of the more circular loop configuration of the embodiment of FIGS. 1A-1D. As is the case with the first clamp 10, the U-shaped urging members 66, 68 of clamp 60 may also lie in planes generally parallel to each other and perpendicular to the axes of the clamping portions 62, 64. A potential use of the embodiment of FIG. 3 may lie in the lesser force exerted by U-shape urging members 66, 68 on the clamping portions 62, 64 with respect to the force exerted by the loop-shape urging members 6, 8 of clamp 10 in FIGS. 1A-1D, making it more suitable for clamping of anatomical structures not requiring a relatively high clamping force. The U-shape configuration of the urging members 66, 68 generally requires less space in the direction perpendicular to the axes of the clamping portions 62, 64. FIG. 3 shows a first stage of assembly of the clamp 60, where the rigid tubular members 63, 65 are joined with the superelastic wire member 61. In this embodiment, mechanical swaging is used to join the tubular members 63, 65 to the wire 61. However, adhesives or laser welding or other methods of attachment could be easily used instead. Similarly, it will be appreciated that rigid tubular members 63, 65 may not necessarily need to be bonded to wire member 61 at all. One may rely, for example, on designing the rigid tubular members 63, 65 so that their inside diameters simply closely fit over the wire 61. In addition, the rigid tubular members 63, 65 could take on many different cross sectional shapes.

Cross-sectional shapes such as ovals, triangles or rectangles with rounded edges could be preferable and may eliminate the addition of the load spreading platens 67, 69 shown in FIG. 4, as these alternate shapes may provide a larger area of contact against the anatomical structure to be engaged by the clamp 50. Since different anatomical structures greatly vary from subject to subject, it is advantageous to have a manufacturing method in which the length 71 (see FIG. 3) of the clamp 60 can be easily varied. By cutting rigid members 63, 65 to various different lengths, different size assemblies can be configured. FIG. 4 shows the next step in the assembly of the clamp. Load spreading platens 67, 69 made of plastic or other biocompatible material such as urethane, may be slipped over the titanium or other suitable material tubing that forms rigid tubular members 63, 65, to provide a resilient surface 73 to spread the load out onto a larger surface area, thereby preventing point source loading of the tissue which might otherwise result in cutting of the tissue before it has had a chance to become internally fused. The platens 67, 69 can be assembled and applied over the rigid tubular members 63, 65 prior to the swaging step or platens 67, 69 can alternatively be manufactured in such a way so as to have a longitudinal split which allows the material to be opened and forced onto the rigid tubular members 63, 65.

Referring to FIG. 5, the clamp 60 may include a fabric cover material 74 made of material such as polyester has been sewn around the clamping portions 62, 64 and urging members 66, 68. It will be appreciated that this material or any other similar materials may be used as a full or partial covering in any of the disclosed embodiments. Such a material is preferably suitable to engage the tissue of the anatomical structure being clamped as well as that of surrounding areas. In exemplary form, the material 74 comprises a circular warp knit fabric tube with a diameter of approximately 4 to 5 mm and made from a combination of 4/100, 2/100 and 1/100 textured polyester. The material 74 may also be heat-treated to cause a velour effect. The fabric or other material 74 is furthermore sewn or otherwise applied over the urging members 66, 68.

Figure 6:
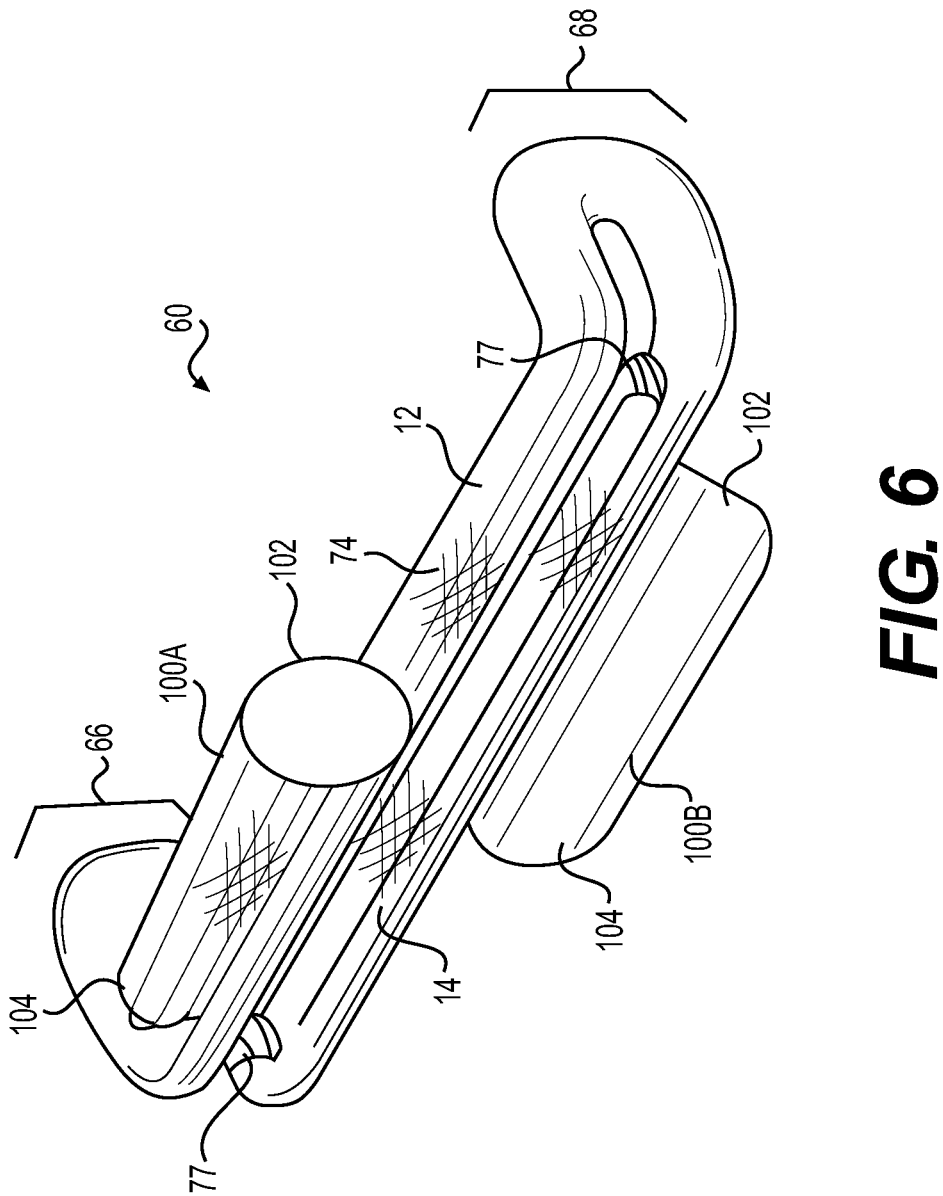
FIG. 6 is an elevated perspective view, from the front, of the exemplary appendage clamp of FIG. 1 with a fabric covering having pockets.

Referring to FIG. 6, the fabric cover material 74 may include one or more pockets 100 that extend substantially in parallel to the tubes 12, 14. Each pocket 100 includes an interior that is circumscribed by the fabric cover material 74 and includes at least one opening at either longitudinal end 102, 104 in order to accommodate insertion of a minimally invasive medical instrument (see FIG. 21, longitudinal shafts 402). In this exemplary embodiment, clamp 60 includes a pair of pockets 100 so that the first pocket 100A is coupled to the material 74 covering the first tube 12 and the second pocket 100B is coupled to the material 74 covering the second tube 14. Each pocket comprises a continuous circumference that is open at one longitudinal end, but closed at an opposing longitudinal. end. By way of example, the first pocket 100A is open at the first longitudinal end 102 and closed at the second longitudinal end 104. But the second pocket 100B is closed at the first longitudinal end 102 and open at the second longitudinal end 104. As will be discussed in more detail hereafter, the openings at opposite ends for the respective pockets 100A, 100B allows for separate minimally invasive tools to couple to the clamp 60 from opposite directions, which may be preferable. It should be noted, however, that the pockets 100 need not include a closed longitudinal end.

Figure 7:
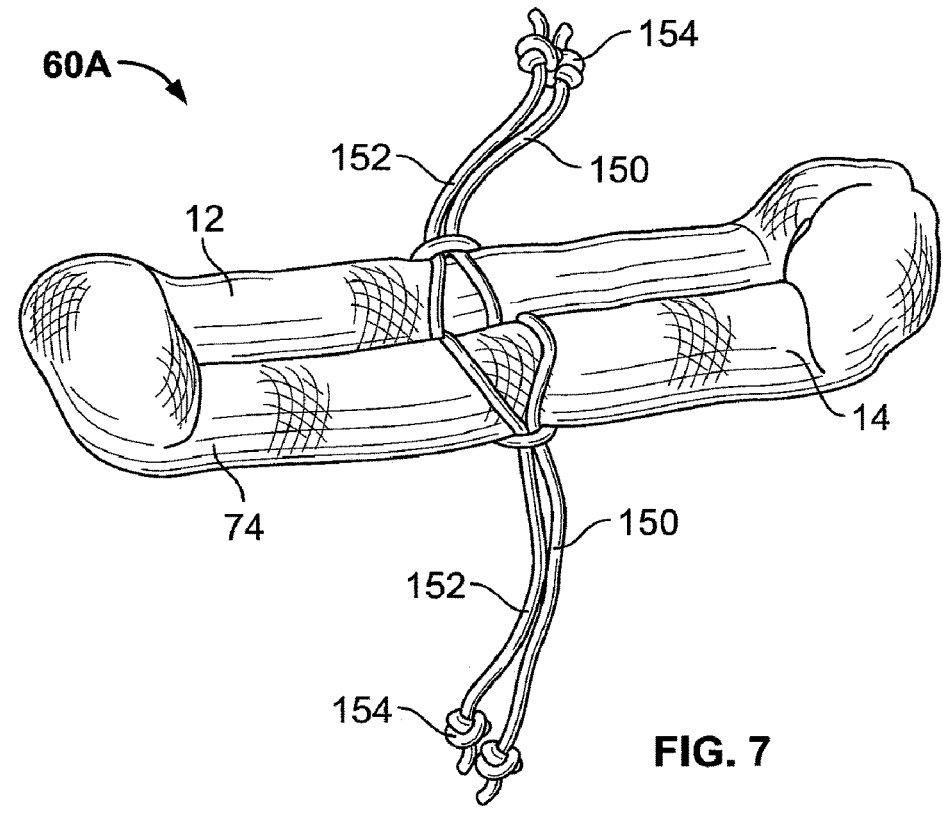
FIG. 7 is an elevated perspective view, from the front, of the exemplary appendage clamp of FIG. 1 with a fabric covering and a first exemplary aid for opening the clamp.

Referring to FIG. 7, the clamp 60 may include suture material 150 circumscribing the tubes 12, 14 and the fabric cover material 74 in order to facilitate opening of the clamp, thereby separating at least a portion of the tubes from one another. A first exemplary suture material 150, shown in FIG. 7, is comprises a closed loop 152 having a knot 154 or some other structure such as a hollow bead (not shown) attached to the loop in order to provide a foothold for a minimally invasive medical instrument to pull on the suture material.

In this first exemplary embodiment, the clamp 60A includes a pair of closed loops 152, with each loop circumscribing a separate one of the tubes 12, 14 and fabric cover material 74. In exemplary form, each loop 152 is positioned proximate the midpoint of a respective tube 12, 14. However, by using a loop 152, repositioning of the loop along the length of the tubes 12, 14 is possible by slackening the loop (i.e., not making the loop taught) and sliding the loop along the exterior of the fabric cover material 74 until reaching the desired location. After reaching the desired location, the loop 152 may be drawn taught to fix its relative position. While this first exemplary embodiment includes one loop for each tube 12, 14, it is also within the scope of the invention to utilize multiple loops 152 for one or both tubes.

Figure 8:
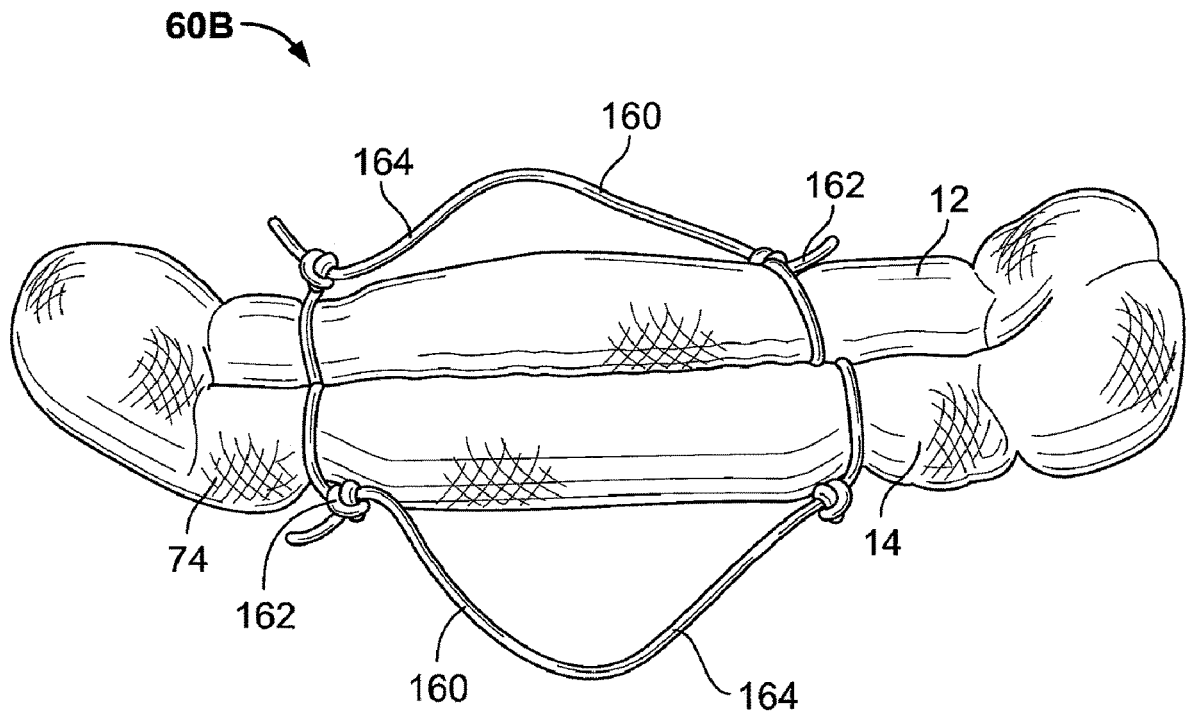
FIG. 8 is an elevated perspective view, from the front, of the exemplary appendage clamp of FIG. 1 with a fabric covering and a second exemplary aid for opening the clamp.

Referencing FIG. 8, a second exemplary clamp 60B includes a pair of corresponding suture handles 160 that circumscribe the tubes 12, 14 and fabric cover material 74 proximate the circumferential ends of the tubes. Each handle 160 comprises two bands 162 that circumscribe the tubes 12, 14 and fabric cover material 74. Each band 162 is concurrently mounted to a suture bridge 164 that extends between the bands and is long enough to bow outward, away from the clamp 60B. In this manner, the suture bridge 164 provides an attachment point for a minimally invasive medical instrument. While this second exemplary embodiment includes one handle for each tube 12, 14, it is also within the scope of the invention to utilize multiple handles 160 for one or both tubes.

Figure 9:
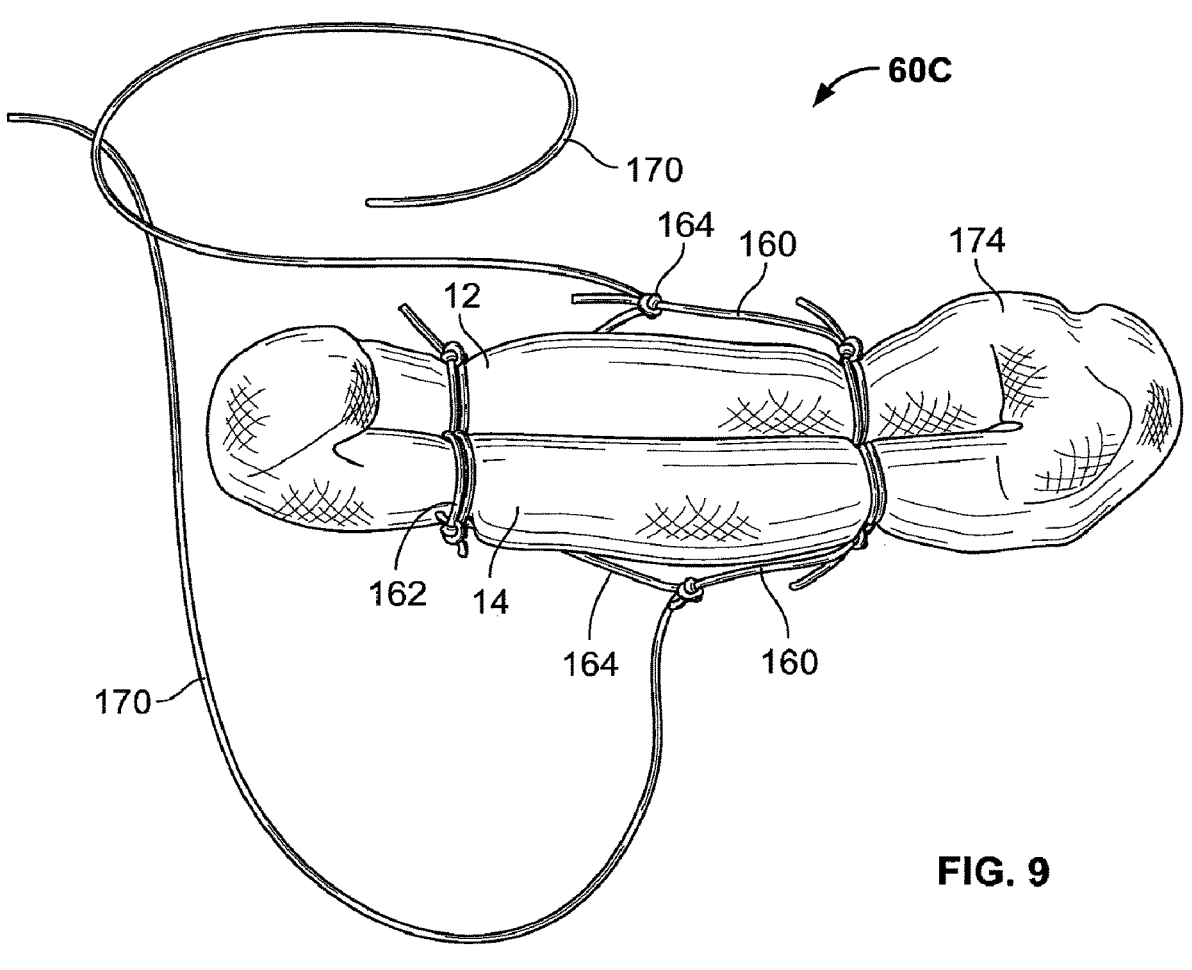
FIG. 9 is an elevated perspective view, from the front, of the exemplary appendage clamp of FIG. 1 with a fabric covering and a third exemplary aid for opening the clamp.

Referring to FIG. 9, a third exemplary clamp 60C includes generally the same structure as the second exemplary clamp 60B, but also includes a suture strand 170 attached to the suture bridge 164. The suture strand 170 may be grasped by a medical instrument and utilized to change the position of the tubes 12, 14 with respect to one another. This change in position may be effectuated by the medical instrument pulling on the strand 170 while the strand is in tension. While the strand 170 is in tension, the strand is concurrently pulling on the suture bridge 164, which operates to pull on the bands 162. When the force of the medical instrument overcomes the spring force of the clamp 60C, the tubes 12, 14 are pulled apart from one another. But when the force of the medical instrument is less than the spring force of the clamp 60C, the tubes 12, 14 are allowed to move toward one another until reaching a default position.

Figure 10:
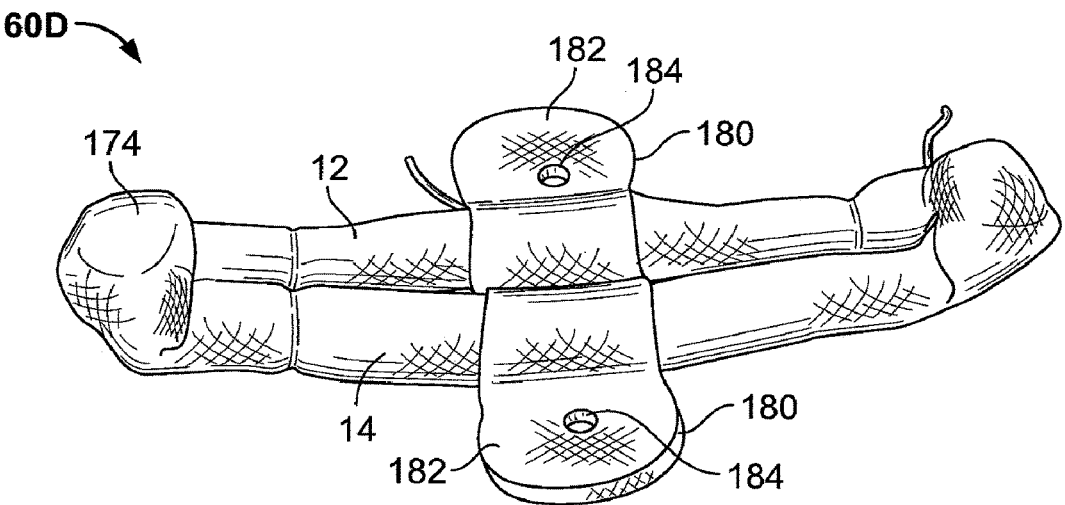
FIG. 10 is an elevated perspective view, from the front, of the exemplary appendage clamp of FIG. 1 with a fabric covering and a fourth exemplary aid for opening the clamp.

Referring to FIG. 10, a fourth exemplary clamp 60D includes the fabric cover material 74. But in this fourth exemplary embodiment, the fabric cover material 74 is supplemented with attachment wings 180 that extend outward, away from the tubes 12, 14 of the clamp 60D. The attachment wings 180 may be integrated into the fabric cover material 74 or may be a separate item that is repositionable along the length of the fabric cover material. Each wing 180 circumscribes a separate tube 12, 14 and includes a flap 182 having at least one through hole 184 that provides a point of attachment for a medical instrument (not shown). In this manner, the medical instrument may include a hook (not shown) that is inserted into the through hole so that the medical instrument may be manipulated and thereby manipulate the wings, and thus the tubes 12, 14 with respect to one another.

By way of example, two separate medical instruments each include a hook that is inserted into a respective through hole 184 on each flap 182. After the hook is inserted, the medical instruments are repositioned so that the flaps 182 are in tension in order to reposition the tubes 12, 14 with respect to one another. While the flaps 182 are in tension, the portion of the wing 180 that circumscribes each tube is operative to pull the tubes apart from one another when the force of the medical instruments overcomes the spring force of the clamp 60D. Alternatively, when the force of the medical instruments is less than the spring force of the clamp 60D, the tubes 12, 14 are allowed to move toward one another until reaching a default position. Because the hook is securely fastened to the flap 182 by way of the through hole 184, it is very unlikely that the medical instrument will become unintentionally disengaged from the flap, which would cause the tubes 12, 14 to rapidly move toward one another and snap shut the clamp 60D.

Figure 11:
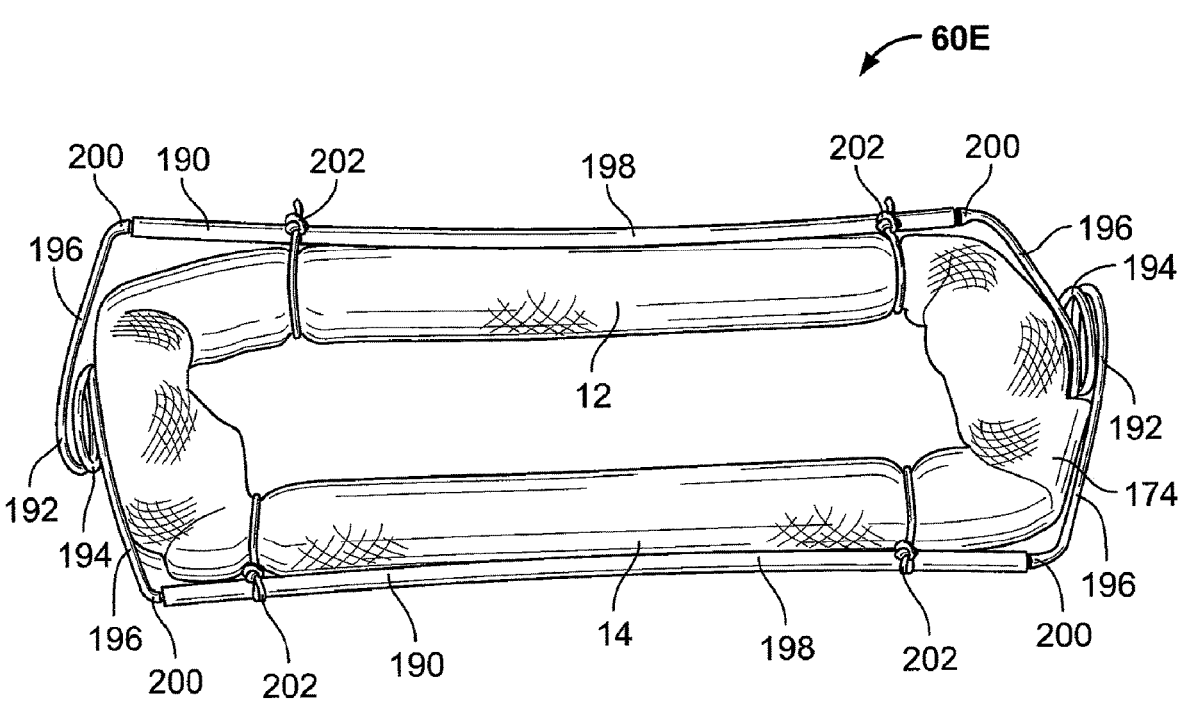
FIG. 11 is a rear view of the exemplary appendage clamp of FIG. 1 with a fabric covering and a fifth exemplary aid for opening the clamp.

Referring to FIG. 11, a fifth exemplary clamp 60E includes a counterbalance spring 190 to decrease the force necessary to open the clamp (i.e., move the tubes 12, 14 apart from one another). The counterbalance spring 190 includes a pair of torsion springs 192 located at the peripheral outline of the wire member 16 and fabric cloth material 74. Each torsion spring 192 comprises metal, cylindrical wire that is shaped to include a coil section 194 and substantially linear sections 196 that transition at one end into the coil section. An opposite end of each of the substantially linear sections 196 transitions into another linear section 198 by way of a rounded corner 200. The two linear sections 198 extend substantially parallel to the tubes 12, 14 and join the torsion springs 192 to one another, Each of the linear sections 198 is joined to a respective one of the tubes 12, 14 by way of suture ties 202 that concurrently circumscribe the tubes, the fabric cover material 74, and the linear sections. In this exemplary embodiment, the clamp 60E includes four suture ties 202, two for each linear section 198.

Figure 12:
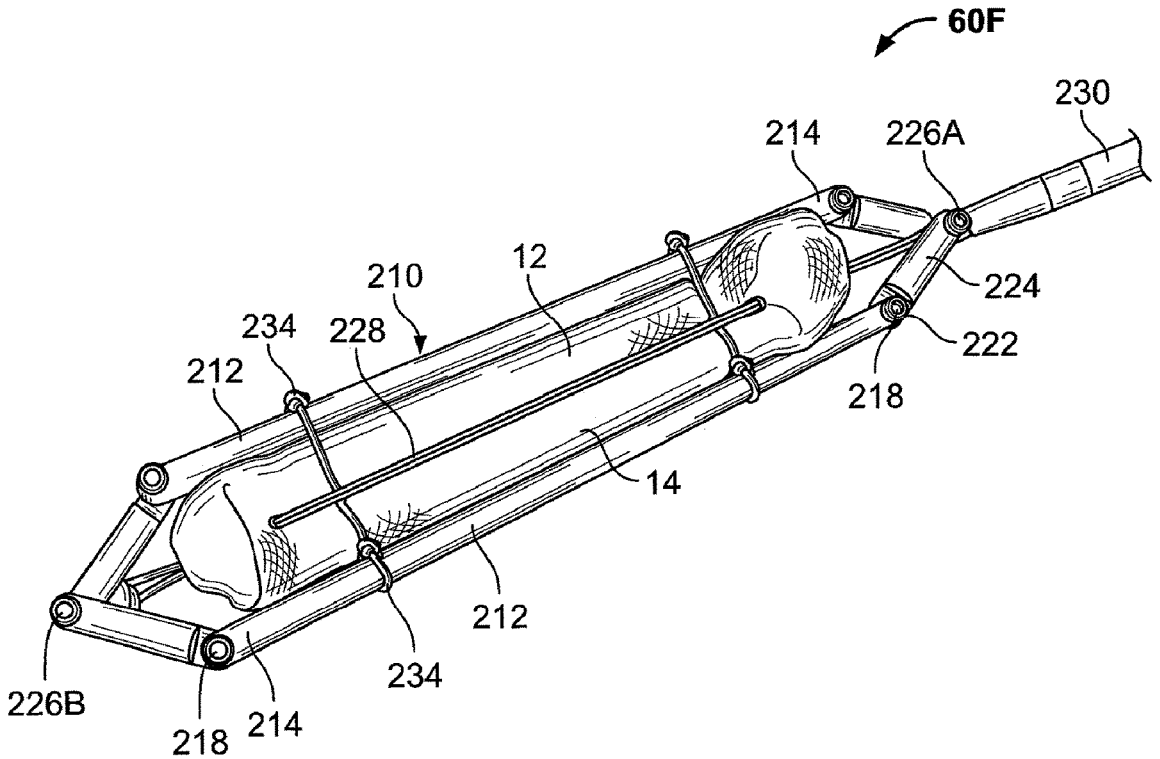
FIG. 12 is a rear view of the exemplary appendage clamp of FIG. 1 with a fabric covering and a rear view of a sixth exemplary aid for opening the clamp.
Figure 13:
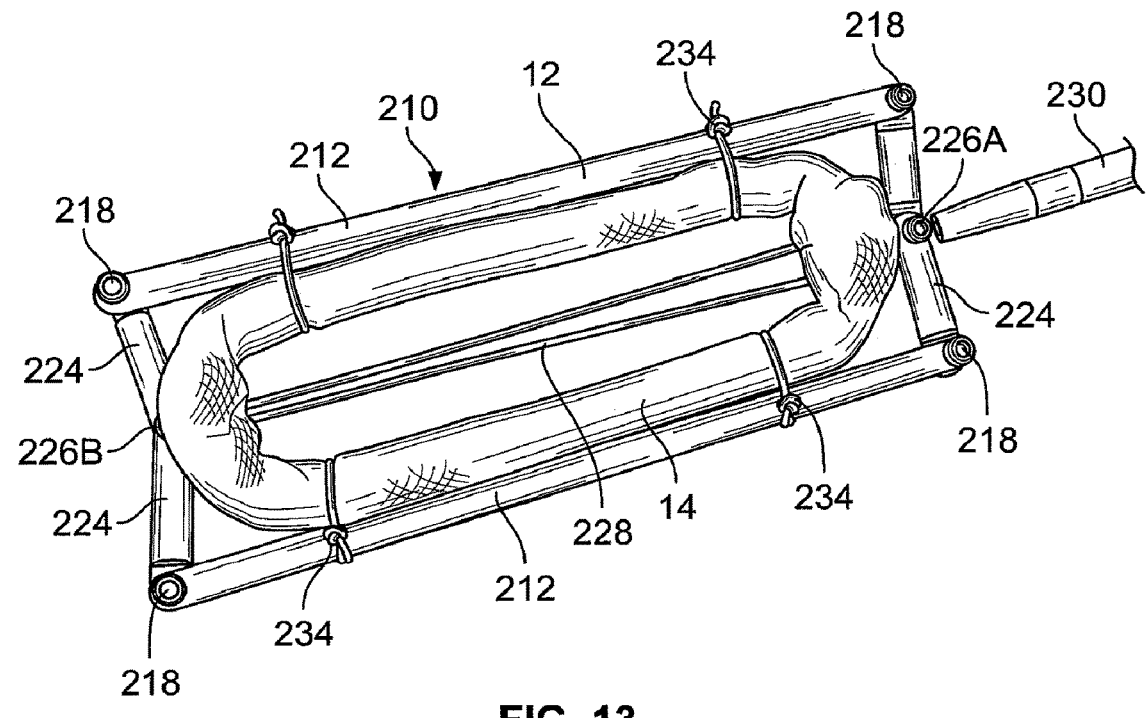
FIG. 13 is a rear view of the exemplary appendage clamp of FIG. 1 with a fabric covering and a rear view of the sixth exemplary aid to deploy the clamp in the open position.
Figure 14:
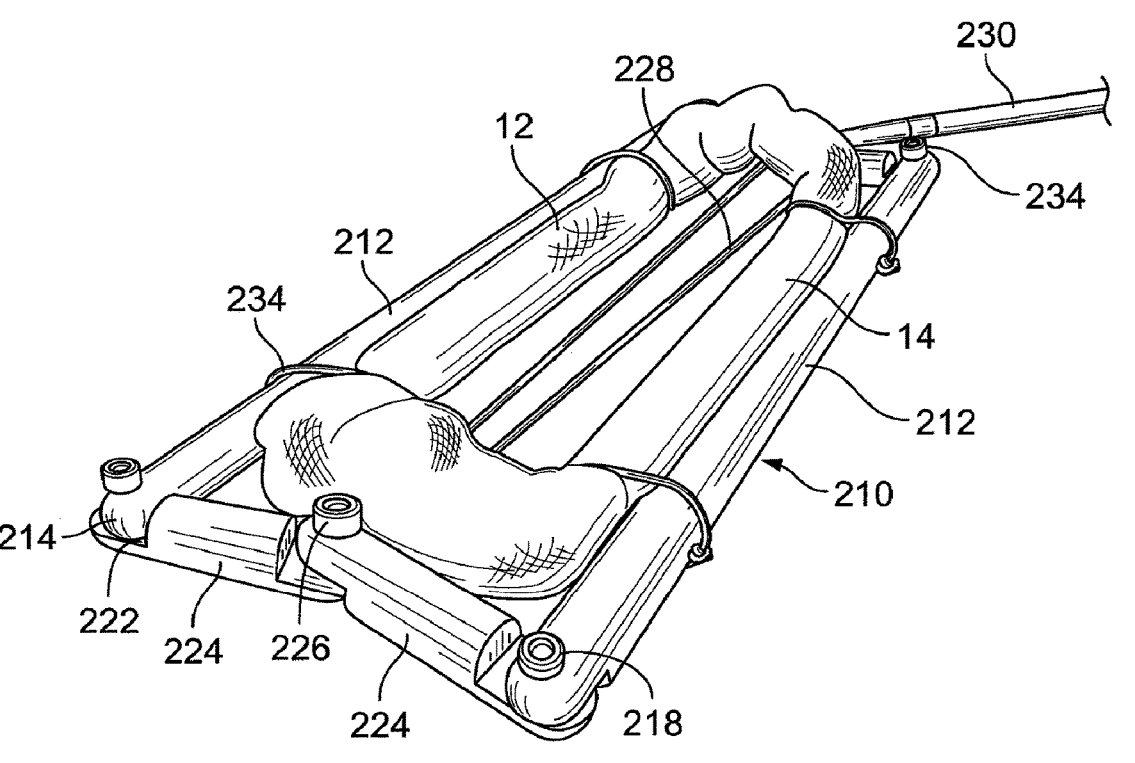
FIG. 14 is an elevated perspective view of the exemplary appendage clamp of FIG. 1 with a fabric covering and an elevated perspective view of the sixth exemplary aid to deploy the clamp in the open position.

Referring to FIGS. 12-14, a sixth exemplary clamp 60F includes an opening mechanism 210 in order open and close the clamp during a surgical procedure. While not required, this clamp 60F is adapted for use in minimally invasive surgical procedures. In exemplary form, the opening mechanism 210 includes a pair of longitudinal cylinders 212 that extend in parallel to the tubes 12, 14. Each cylinder 212 includes a notch formed at each longitudinal end by way of a diametric cut perpendicular to the longitudinal axis that results in a flange 214 comprising the remaining material. The flange 214 includes a through hole that also extends perpendicular to the longitudinal axis and perpendicular to the diametric cut. This through hole receives a pin 218 that is concurrently received by a through hole extending through the flange 222 of a shorter cylinder 224. This shorter cylinder 224 also includes notches at each longitudinal end. In this manner, the shorter cylinders 224 are pivotable at one end about their respective pins 218 that are concurrently received by the longitudinal cylinders 212.

Opposite the longitudinal end of each shorter cylinder 224 that is mounted to a respective longitudinal cylinder 212, the second longitudinal end of the shorter cylinder 224 is mounted to another second longitudinal end of another shorter cylinder 224. The second longitudinal end of each shorter cylinder 224 also includes a through hole that receives a pin 226 so that the shorter cylinders 224 are pivotable with respect to one another about each pin. In other words, there are four shorter cylinders 224 and two longitudinal cylinders 212 that create an enclosed outline that is able to change shapes to "increase or decrease the distance between the longitudinal cylinders 212.

This sixth exemplary clamp 60F is repositionable between an elongated orientation and a generally truncated orientation. In order to reposition the opening mechanism 210 between these two orientations, the mechanism includes a length of suture material 228 having one end securely coupled to the pin 226B extending through two of the shorter cylinders 224. The suture material 228 extends to an opposite pin 226B and is wrapped around the pin 226B and returned back toward the first pin 226A. When the suture material 228 reaches the first pin 226A, it is threaded through a minimally invasive hollow positioning rod 230 so that the free end of the suture material extends beyond the end of the positioning rod. In this manner, the suture material may be drawn taught to reposition the opening mechanism 210 from the elongated orientation to the generally truncated orientation.

Alternatively, the opening mechanism 210 may include one or more lengths of suture material 228 having one end securely coupled the opposite pin 226B and the free end being directed toward the first pin 226A and threaded through a minimally invasive hollow positioning rod 230 so that each free end of the suture material extends beyond the end of the positioning rod. In this manner, issues of the suture material 228 having to move past the opposite pin 226B without catching are obviated.

Once the opening mechanism 210 is positioned in the truncated orientation, the mechanism is effectively locked in this position by the cylinders 224 rotating over center and is locked into position. Accordingly, after reaching the truncated orientation, the suture material 228 may be removed so that the area between the tubes 12, 14 of the clamp 60F. After reaching the truncated orientation, the clamp 60F is positioned so that the desired tissue interposes the tubes 12, 14. Thereafter, the shorter cylinders 24 are manually pushed outward so the mechanism can be repositioned to its elongated orientation (see FIG. 12) with the clamp 60F sandwiching the desired tissue. At this point, the suture material 234 coupling the opening mechanism 210 to the clamp 60F is removed, as well is the opening mechanism, in order to leave the clamp 60F by itself sandwiching the desired tissue.

Figure 15:
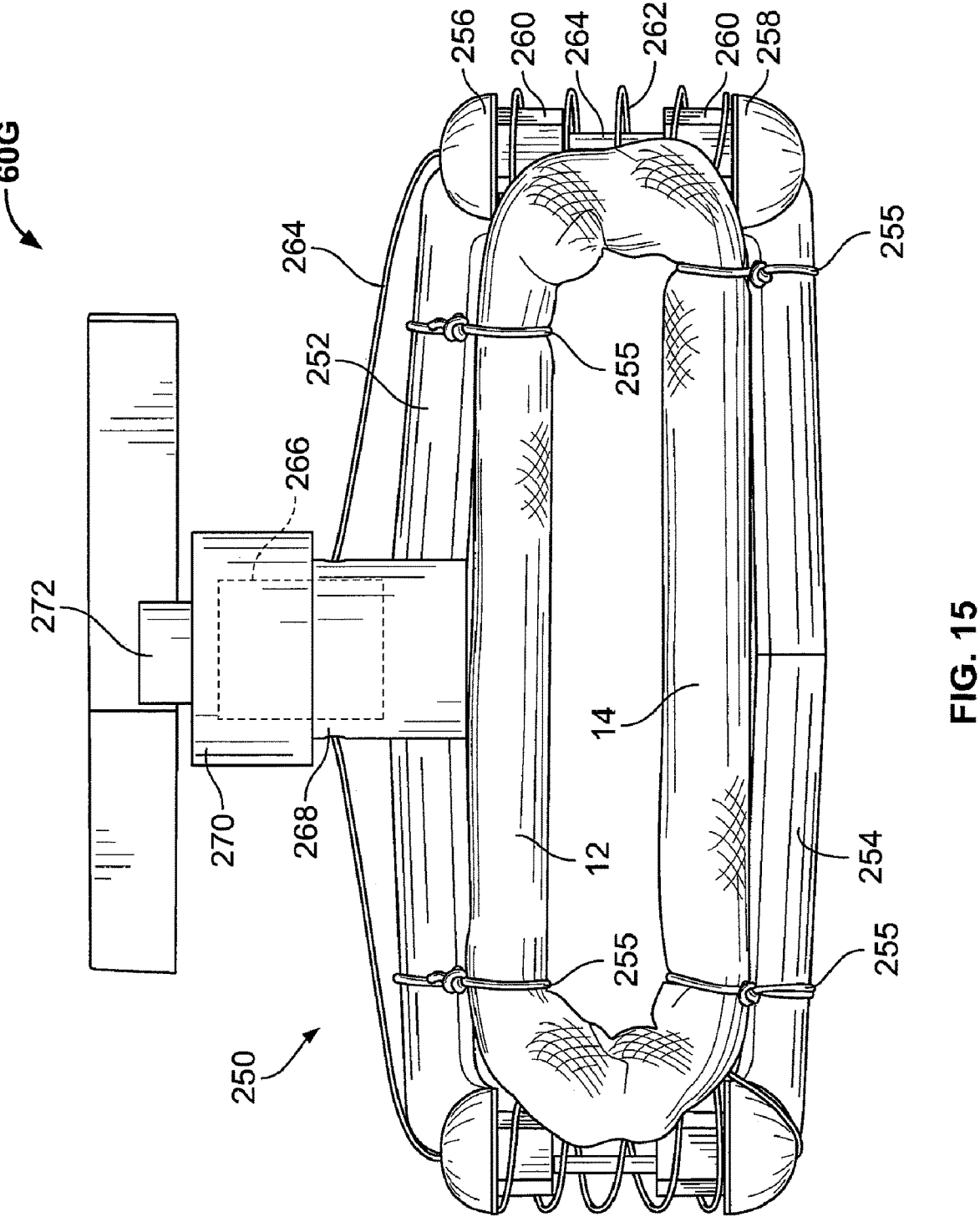
FIG. 15 is a rear view of the exemplary appendage clamp of FIG. 1 with a fabric covering and a seventh exemplary aid for opening the clamp.

Referencing FIG. 15, a seventh exemplary clamp 60G includes an opening mechanism 250 in order open and close the clamp during a surgical procedure. While not required, this clamp 60G may be used in minimally invasive surgical procedures. In exemplary form, the opening mechanism 250 includes a pair of longitudinal beams 252, 254 that extend in parallel to the tubes 12, 14 and are mounted thereto using suture ties 255. Both beams 252, 254 include a pair of circular plateaus 256, 258 upon which a pair of cylindrical bushings 260 are mounted. In this exemplary embodiment, the plateaus 256 of the first beam 252 generally face the plateaus 258 of the second beam 254. Each of the circular plateaus 256, 258 and the cylindrical bushings 260 mounted thereto are separated from one another by a spring 262 that interposes the plateaus. This spring 262 operates to bias the opening mechanism 250 so that the clamp 60G is in the open position. Each plateau 256, 258, as well as each cylindrical bushing 260, includes an opening that receives a cable 264 that extends through the plateaus and bushings.

One end of the cable 264 is mounted to the bottom beam 254, while the cable is routed through the openings through the circular plateaus 256, 258 and the cylindrical bushings 260 and ultimately wound around a drum 266 that is mounted to the top beam 252. Specifically, the top beam 252 is bisected and mounted to a cylindrical housing 268 that at least partially surrounds the drum 266, while allowing the drum to rotate within the housing. This housing 268 includes two openings on opposite sides that allow the cable to enter the housing and be wound around the drum 266. A cap 270 is repositionably mounted to the top of the housing 268 and is directly mounted to the drum 266. In this manner, rotation of the cap 270 correspondingly results in rotation of the drum 266. To facilitate rotation of the cap 270, the cap includes a head 272 dimensioned to receive a driver (not shown) in order to reposition the drum 266.

Repositioning of the drum 266 causes more or less cable 264 to be wound therearound. When more cable 264 is wound around the drum (i.e., retracted), the tension on the cable overcomes the spring bias of the spring 262 and the bias of the damp 60F. This retracting of the cable 264 causes the tubes 12, 14 and the beams 252, 254 to be moved closer to one another. Eventually, when sufficient retraction of the cable 264 is reached, the tubes 12, 14 effectively close off the opening therebetween. In a preferred sequence, tissue (not shown) is inserted between the tubes 12, 14 when the cable 264 is extended, only to have the cable eventually retracted around the drum 266 so that the tubes move closer to one another and the tissue is clamped therebetween. After the tissue is clamped between the tubes 12, 14, the suture ties 255 are severed in order to separate and remove the opening mechanism 250.

Figure 16:
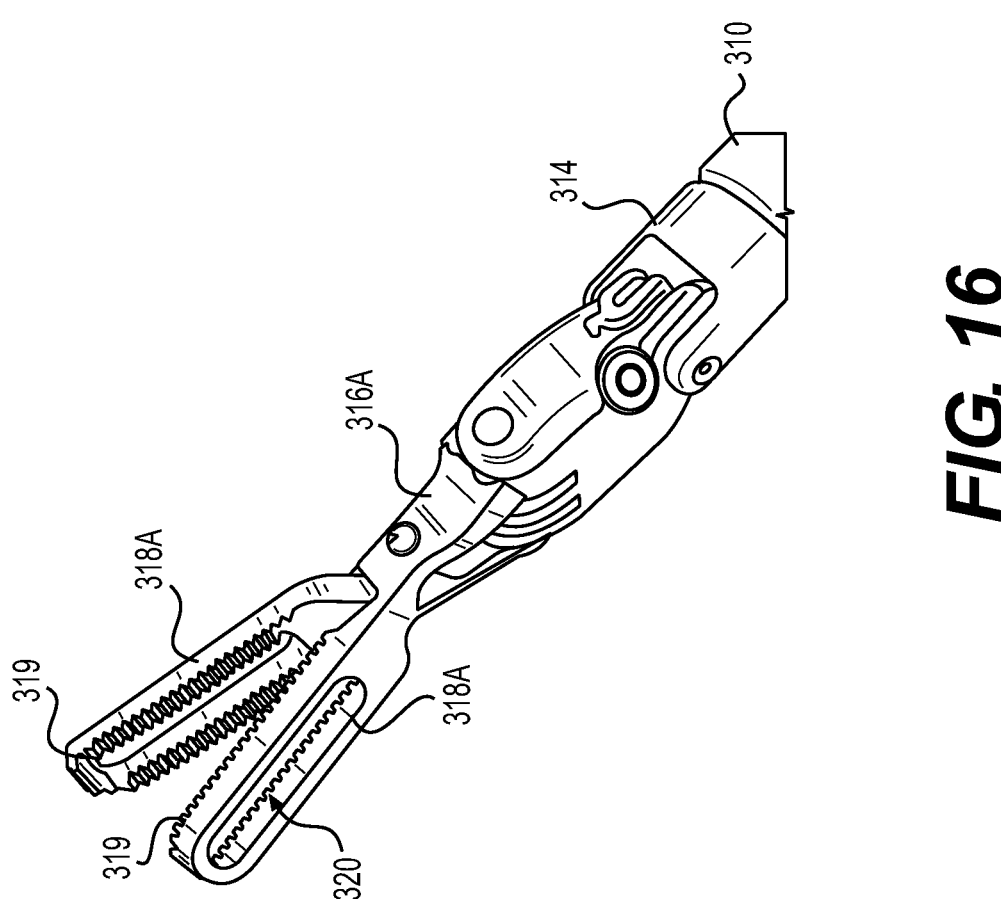
FIG. 16 is an elevated perspective view of a first exemplary robotic end effector.
Figures 17, 18:
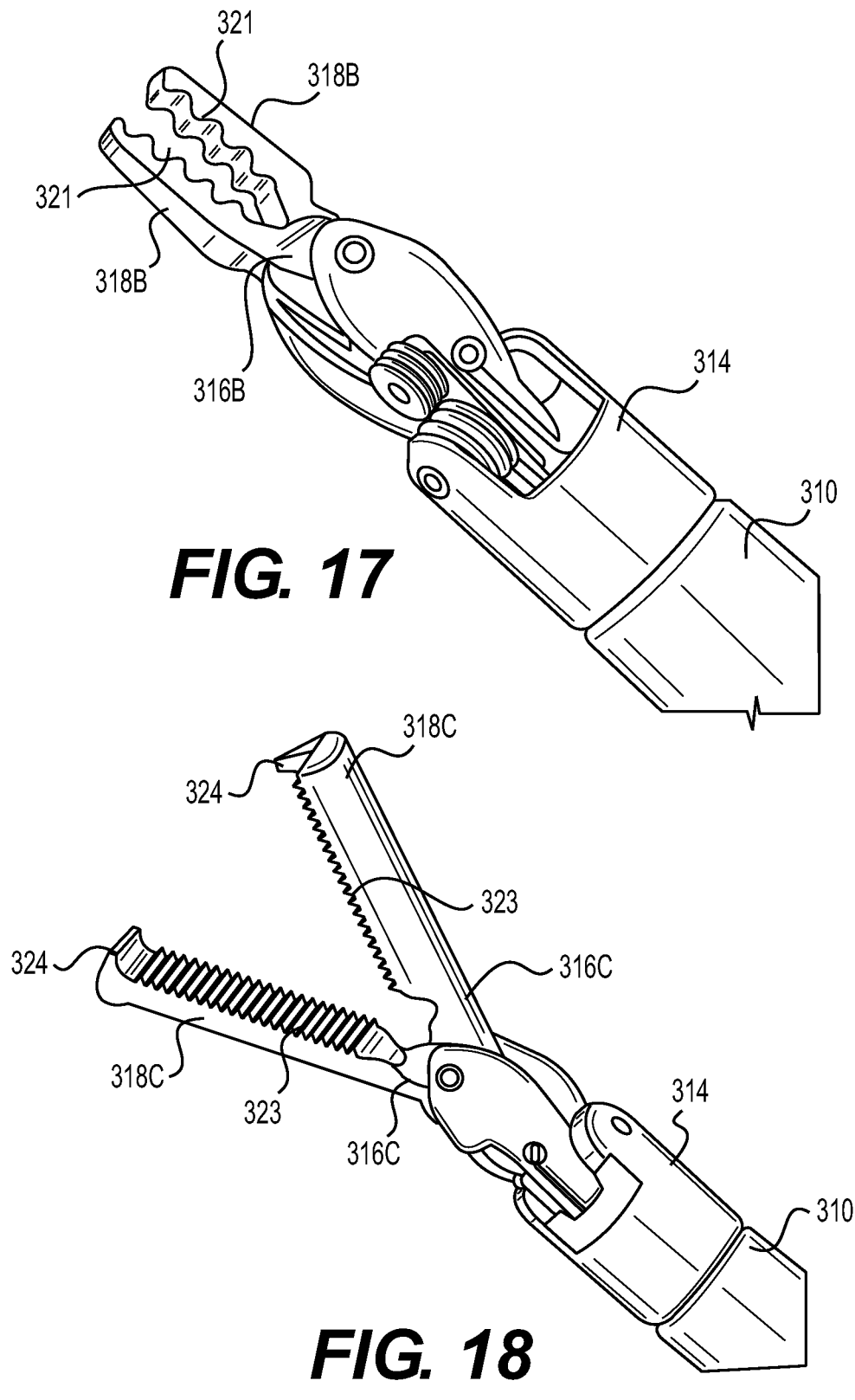
FIG. 17 is an elevated perspective view of a second exemplary robotic end effector.
FIG. 18 is an elevated perspective view of a third exemplary robotic end effector.

Referring to FIGS. 16-19, each of the foregoing and following exemplary embodiments may be manipulated by control arm 310 that is a component of a telesurgical system (not shown). Exemplary telesurgical systems include those such as the daVinci® Surgical System, available from Intuitive Surgical, Inc. of Mountain View, Calif, disclosed in U.S. Pat. No. 6,770,081, the disclosure of which is incorporated herein by reference. The robotic control arm 310 includes an elongated shaft and an axial adjustment coupling 314. FIGS. 16-18 show exemplary end effectors 316A, 316B, 316C, 316D that may be coupled to the adjustment coupling 314 in order to open and close corresponding jaws 318A, 318B, 318C, 318D in order for the end effectors to grip and release aspects of the foregoing and following exemplary embodiments to facilitate opening and/or closing of the clamp. It should also be noted that the foregoing and following exemplary embodiments may be manipulated by a control arm that is directly repositionable by a human operator as opposed to a robotic application.

Referring specifically to FIG. 16, a first exemplary end effector 316A is available from Intuitive Surgical, Inc. of Mountain View, Calif as the ProGrasp Forceps (www.intuitivesurgical.com) and includes oblong jaws 318A that are serrated on opposing contact surfaces 319. Each oblong jaw 318A also include an oblong through opening 320 that, as will be discussed in more detail hereafter, allows for projections to extend through the opening and provides the opportunity for greater control and pulling forces exerted by the jaws 318A.

Referring specifically to FIG. 17, a second exemplary end effector 316B is available from Intuitive Surgical, Inc. of Mountain View, Calif as the Rasano Forceps (www.intuitivesurgical.com) and includes elongated jaws 318B that are serrated on opposing contact surfaces 321. The serrations on each elongated jaw 318B are so pronounced that, as will be discussed in more detail hereafter, the serrations trap sutures or other aspects therebetween to provide the opportunity for greater control and pulling forces exerted by the jaws 318B.

Referencing FIG. 18, a third exemplary end effector 316C is available from Intuitive Surgical, Inc. of Mountain View, Calif as the Cobra Grasper (www.intuitivesurgical.com) and includes elongated jaws 318C that are serrated on opposing contact surfaces 323. In addition, the jaws 318C also include upstanding, triangular teeth 324 at the end of each jaw. The serrations on each elongated jaw 318C, as will be discussed in more detail hereafter, provide the jaws with the opportunity for greater control and pulling forces. Conversely, the triangular teeth 324 may be utilized as wedges or as graspers to direct the contact forces of the jaws 318C into a very small contact area.

Figure 19:
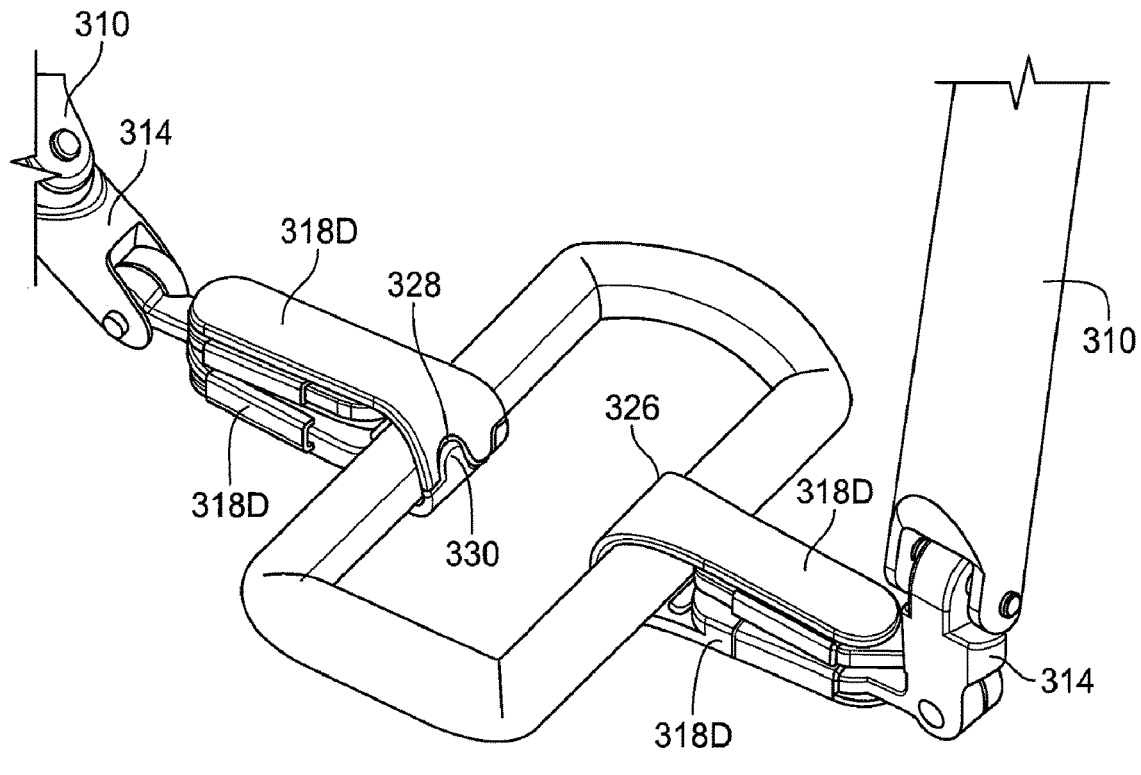
FIG. 19 is an elevated perspective view of a pair of fourth exemplary robotic end effectors with attachment holding the exemplary appendage clamp of FIG. 1 in the open position.

Finally, referring to FIG. 19, a fourth exemplary end effector 316D includes jaws 318D that are rounded over at the distal ends 326. Each jaw 318D includes a curved wave pattern at its distal end the complements the opposing jaw. In other words, where one of the jaws has a curved opening 328, the opposing jaw has a curved projection 330 that precisely fits within the curved opening. The curved projections on each jaw 318D, as will be discussed in more detail hereafter, conform the jaws around cylindrical objects. In addition, the curved projections provide resistance to pulling forces that are attempting to pull objects out from between the jaws 318D.

Figure 20:
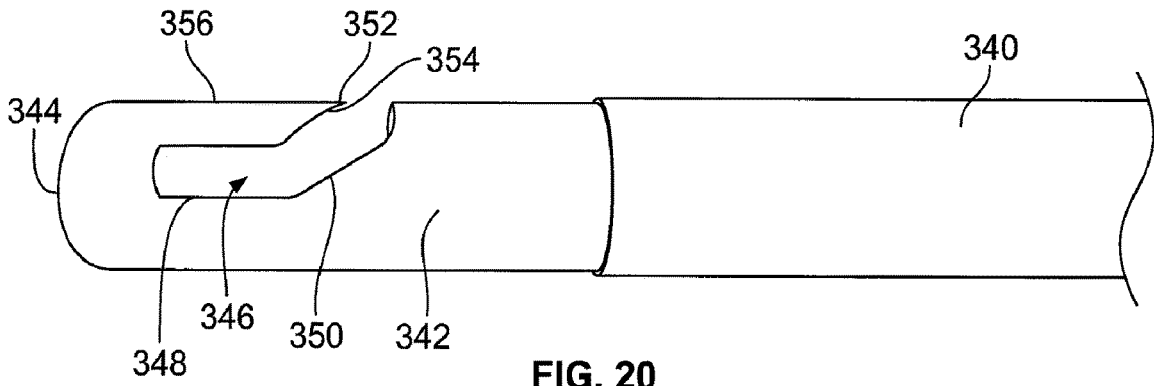
FIG. 20 is a profile view of an exemplary tool for use with some of the exemplary clamps disclosed herein.

Referring to FIG. 20, some of the foregoing and following exemplary embodiments may be manipulated by tool 340 having a hooked end 342. Specifically, the hooked end 342 is generally cylindrical and rounded at its tip 344. A through channel 346 is formed into the end 342 and includes a horizontal segment 348 and an angled segment 350. Partially defining the through channel 346 is a tapered point 352, facing away from the tip 344, having a planar underneath surface 354 and a rounded top surface 356. In exemplary form, the height of the through channel 346 may vary depending upon the application, but in exemplary form, the height is large enough to accommodate throughput of suture material. However, in exemplary form, the height of the through channel 346 is not large enough to allow a suture knot or another larger object from passing through the channel.

By way of example, the tool 340 may be utilized to manipulate the exemplary embodiments shown in FIGS. 7 and 8. Specifically, referring to FIGS. 7 and 20, the hooked end 342 may be positioned over of below the loop 152 of suture extending away from the tubes 12, 14. In this fashion, the hooked end 342 is generally oriented perpendicular to the suture loop 152 and longitudinally repositioned to capture the suture within the channel 346. Then, the tool 340 is further repositioned to pull on the suture 152 and force the suture to contact the far wall 358 and eventually cause the suture to be repositioned with respect to the tool so that the suture knot 154 is adjacent to the hooked end 342. As such, when the tool 340 is further repositioned to pull on the suture 152, the suture then pulls on one of the tubes 12, 14. In exemplary form, two tools 340 would be used to couple to corresponding suture loops 152 and be pulled in opposite directions to pull the tubes 12, 14 apart and thus open the clamp 60A. The tools 340 could then be utilized to reposition the clamp 60A and close the clamp around the desired tissue by moving the hooked ends 342 closer to one another. Thereafter, the sutures may be cut and removed from around the tubes prior, subsequent to, or concurrent with removal of the tools 340 from the clamp 60A deployment location.

Likewise, referring to FIGS. 8 and 20, the hooked end 342 may be positioned over of below a suture bridge 164 operatively coupled to one of the tubes 12, 14 of the clamp 60B. In this fashion, the hooked end 342 is generally oriented perpendicular to the suture bridge 164 and longitudinally repositioned to capture the suture bridge within the channel 346. Then, the tool 340 is further repositioned to pull on the suture bridge 164 and correspondingly pull on the bands 162 coupled to one of the tubes 12, 14. In exemplary form, two tools 340 would be used to couple to corresponding suture bridges 164 and be pulled in opposite directions to pull the tubes 12, 14 apart and thus open the clamp 60B. The tools 340 could then be utilized to reposition the clamp 60B and close the clamp around the desired tissue by moving the hooked ends 342 closer to one another. Thereafter, the sutures may be cut and removed from around the tubes prior, subsequent to, or concurrent with removal of the tools 340 from the clamp 60B deployment location.

Figure 21:
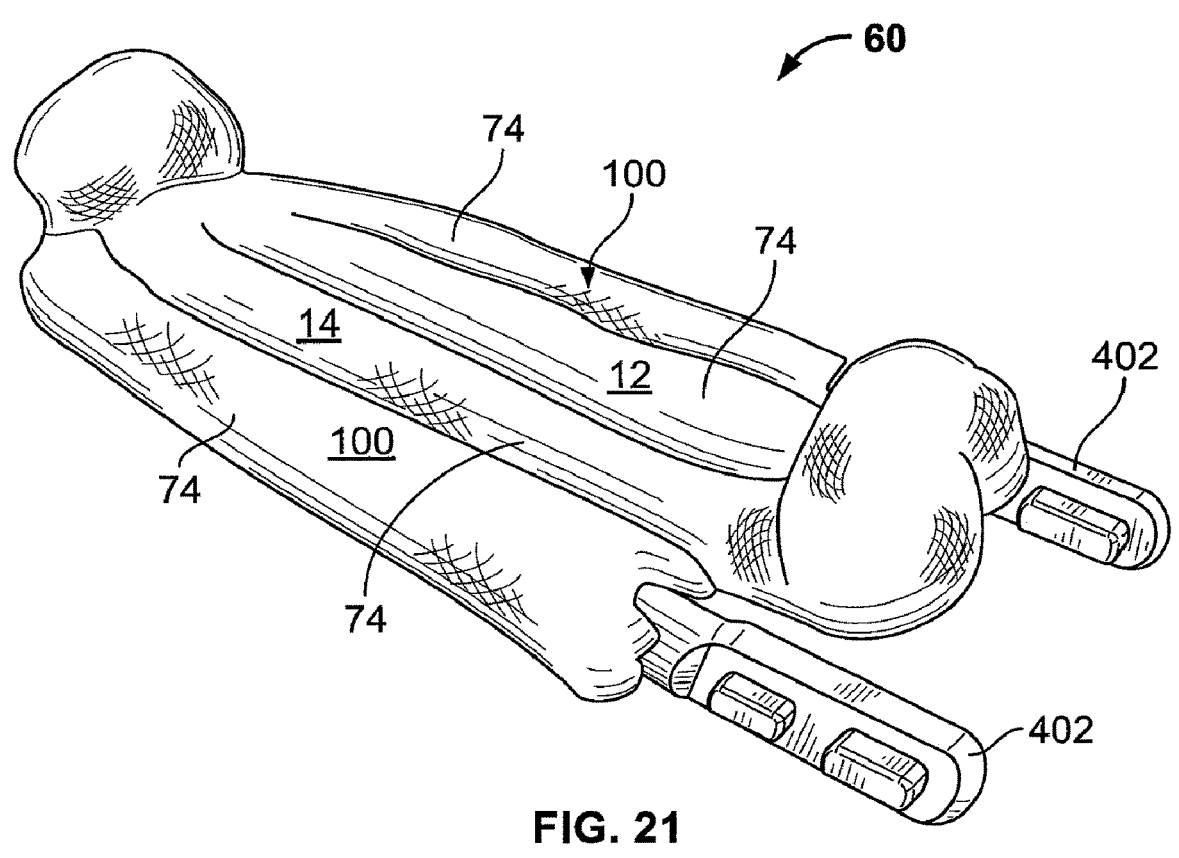
FIG. 21 is an elevated perspective view of the exemplary appendage clamp of FIG. 6 with a fabric covering and an elevated perspective view of the exemplary aid to deploy the clamp in the open position, shown with optional longitudinal shafts inserted into the exemplary aid.
Figure 22:
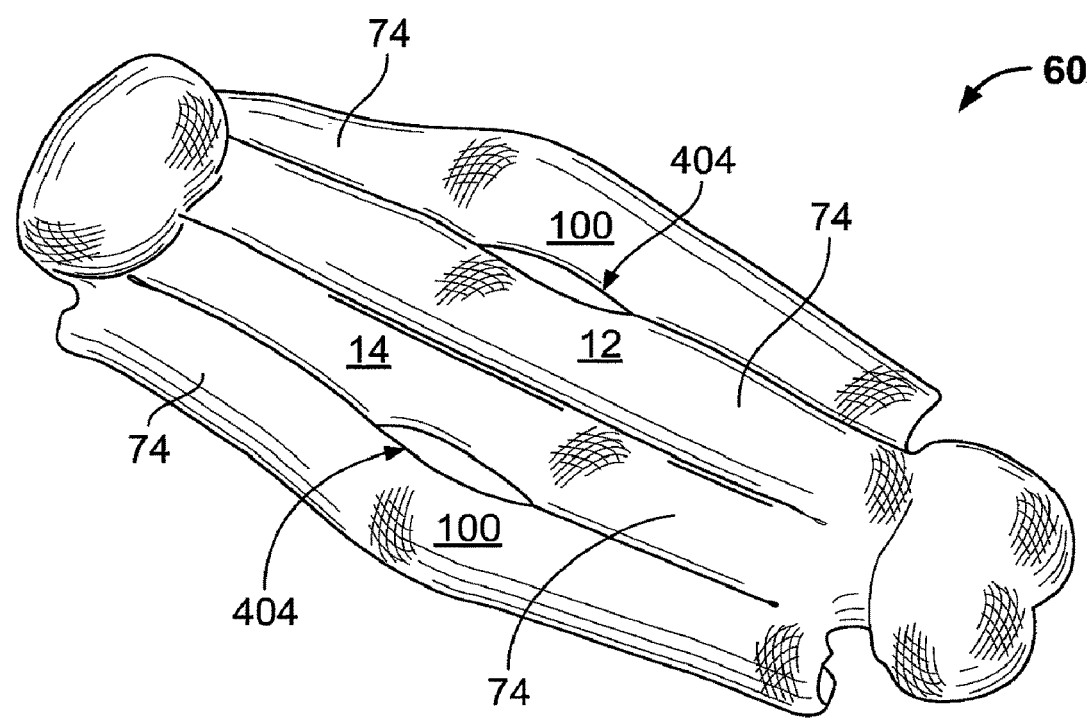
FIG. 22 is a top view of the appendage clamp and the exemplary aid of FIG. 21.
Figure 23:
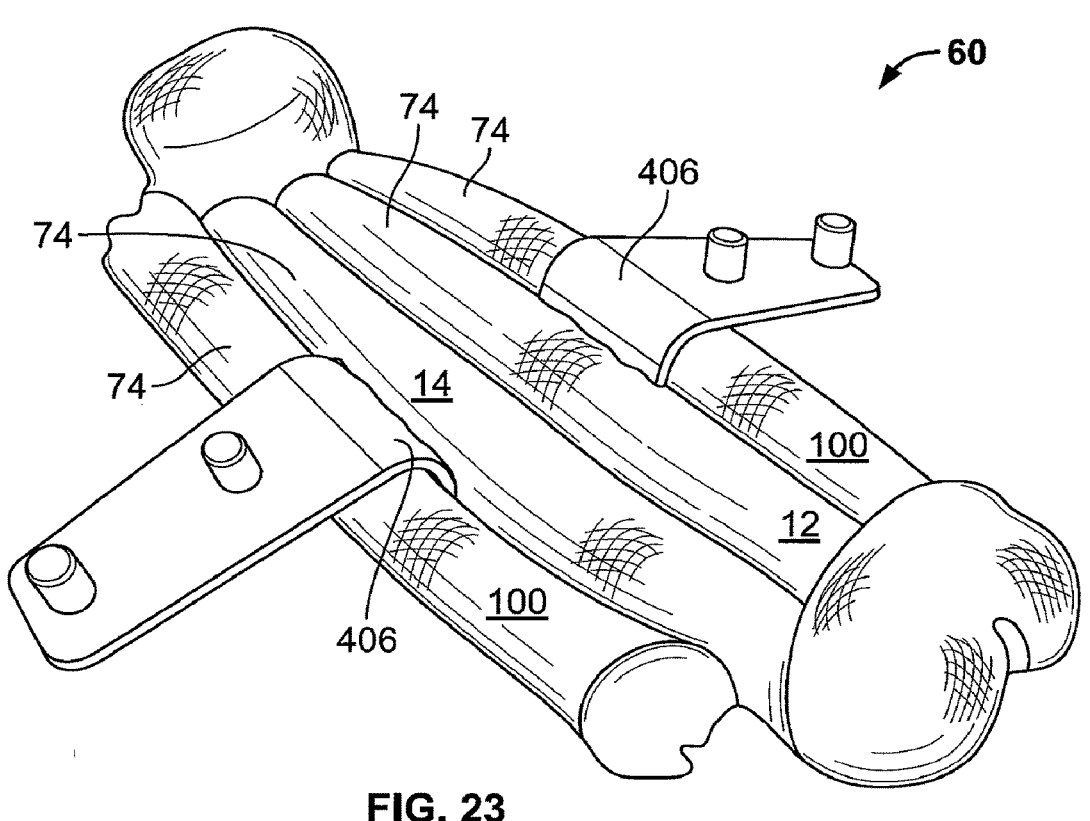
FIG. 23 is an elevated perspective view of the appendage clamp and the eighth exemplary aid of FIG. 21, shown with optional spreaders inserted in between the eighth exemplary aid and the appendage clamp

Referencing FIGS. 21-23, the exemplary clamp 60 of FIG. 6 is shown in some additional views. Referring specifically to FIG. 21, by way of example, the clamp 60 includes a pair of pockets 100 that extend substantially in parallel to the tubes 12, 14. Each pocket 100 is sewn along its longitudinal length to the fabric cover material 74 extending around the tubes 12, 14. This longitudinal stitching does not affect the hollow interior of each pocket 100, which is adapted to accommodate longitudinal shafts 402 that may be grasped by a robotic manipulated or manual end effector (see e.g., FIG. 16, end effector 316A) in order to reposition the shafts away from one another to separate the tubes 12, 14 and open the clamp 60.

Referring to FIGS. 22 and 23, alternatively, each pocket 100 may have its opposing longitudinal ends sewn to the fabric cover material 74 extending around the tubes 12, 14. In this fashion, because each pocket 100 is not sewn to the fabric cover material 74 along its entire length, there are locations where each pocket is separable from the fabric cover material to create a gap 404. This gap 404 may provide an entry point for rounded over spreaders 406 that may be grasped by a robotic manipulated or manual end effector (see e.g., FIG. 16, end effector 316A) in order to reposition the spreaders 406 away, thereby pulling the pockets 100 apart. In this manner, repositioning of the spreaders 406 apart eventually causes the tubes 12, 14 to be pulled apart and the clamp 60 opened.

It should also be understood that the spreaders 406 can be used to open any of the foregoing exemplary clamps 60-60H simply by placing the ends of the spreaders adjacent to one another in between the tubes 12, 14 and thereafter repositioning the spreaders apart from one another to create or increase the gap between the tubes.

Figure 24:
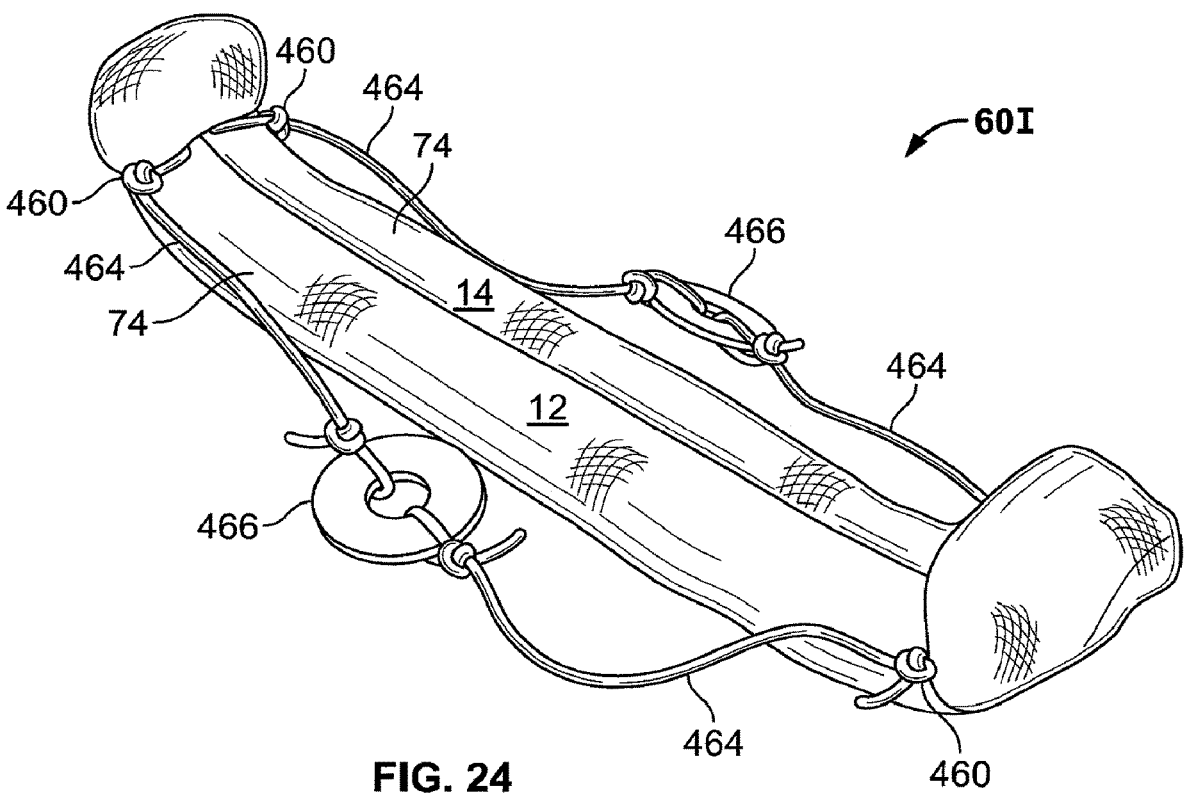
FIG. 24 is an elevated perspective view of an exemplary appendage clamp with a fabric covering and an elevated perspective view of the ninth exemplary aid to deploy the clamp in the open position.

Referencing FIG. 24, a ninth exemplary clamp 601 includes a pair of corresponding suture handles 460 that circumscribe the tubes 12, 14 and fabric cover material 74 proximate the circumferential ends of the tubes. Each handle 460 comprises two bands that circumscribe the tubes 12, 14 and fabric cover material 74. Each band is concurrently mounted to two suture strands 464 that are concurrently mounted to a metal ring 466. In this manner, the two suture strands 464 and the ring 466 each provides an attachment point for a minimally invasive medical instrument, for example, to pull on in order to reposition the tubes 12, 14 with respect to one another. While this ninth exemplary embodiment includes one handle for each tube 12, 14, it is also within the scope of the invention to utilize multiple handles 460 for one or both tubes.

Figure 25:
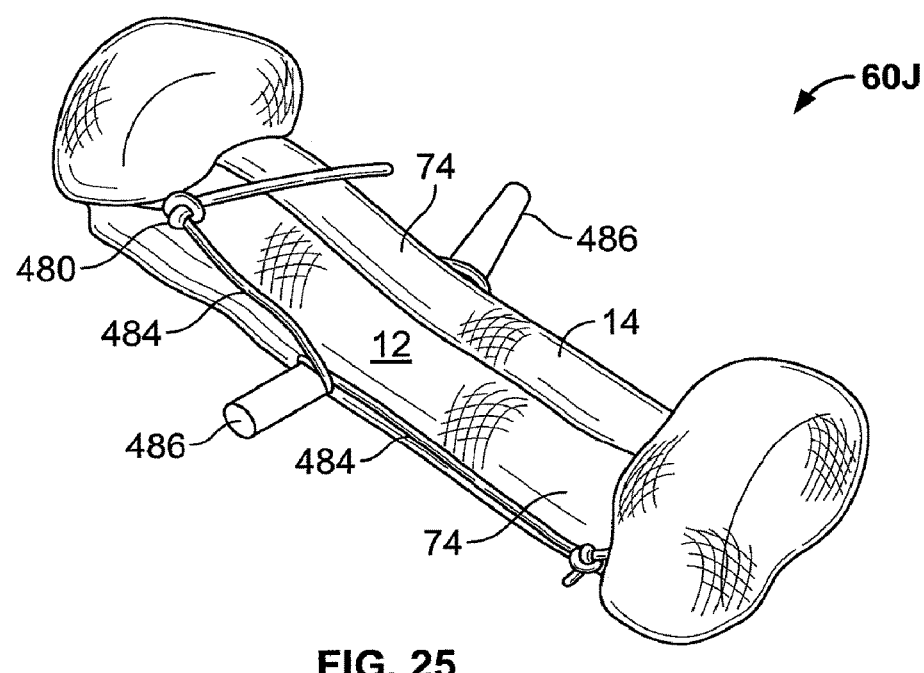
FIG. 25 is an elevated perspective view of an exemplary appendage clamp with a fabric covering and an elevated perspective view of the tenth exemplary aid to deploy the clamp in the open position.

Referring to FIG. 25, a tenth exemplary clamp 601 includes a pair of corresponding suture handles 480 that circumscribe the tubes 12, 14 and fabric cover material 74 proximate the circumferential ends of the tubes. Each handle 480 comprises two bands that circumscribe the tubes 12, 14 and fabric cover material 74. Each band is concurrently mounted to two suture strands 484 that are concurrently mounted to a metal crimp cylinder 486. In this manner, the two suture strands 484 and the crimp cylinder 486 each provides an attachment point for a minimally invasive medical instrument, for example, to pull on in order to reposition the tubes 12, 14 with respect to one another. While this ninth exemplary embodiment includes one handle for each tube 12, 14, it is also within the scope of the invention to utilize multiple handles 480 for one or both tubes.

Figure 26:
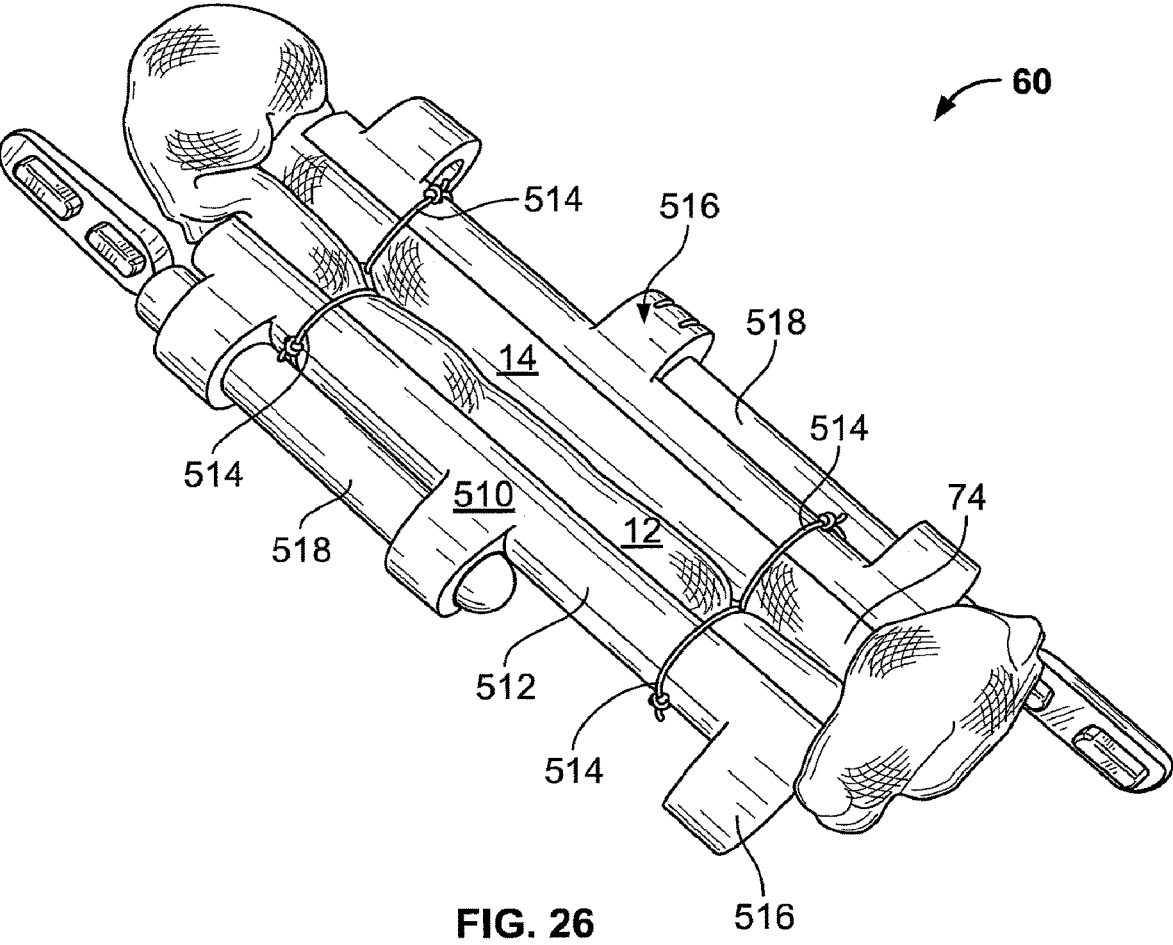
FIG. 26 is an elevated perspective view of an exemplary appendage clamp with a fabric covering and an elevated perspective view of the eleventh exemplary aid to deploy the clamp in the open position.
Figure 27:
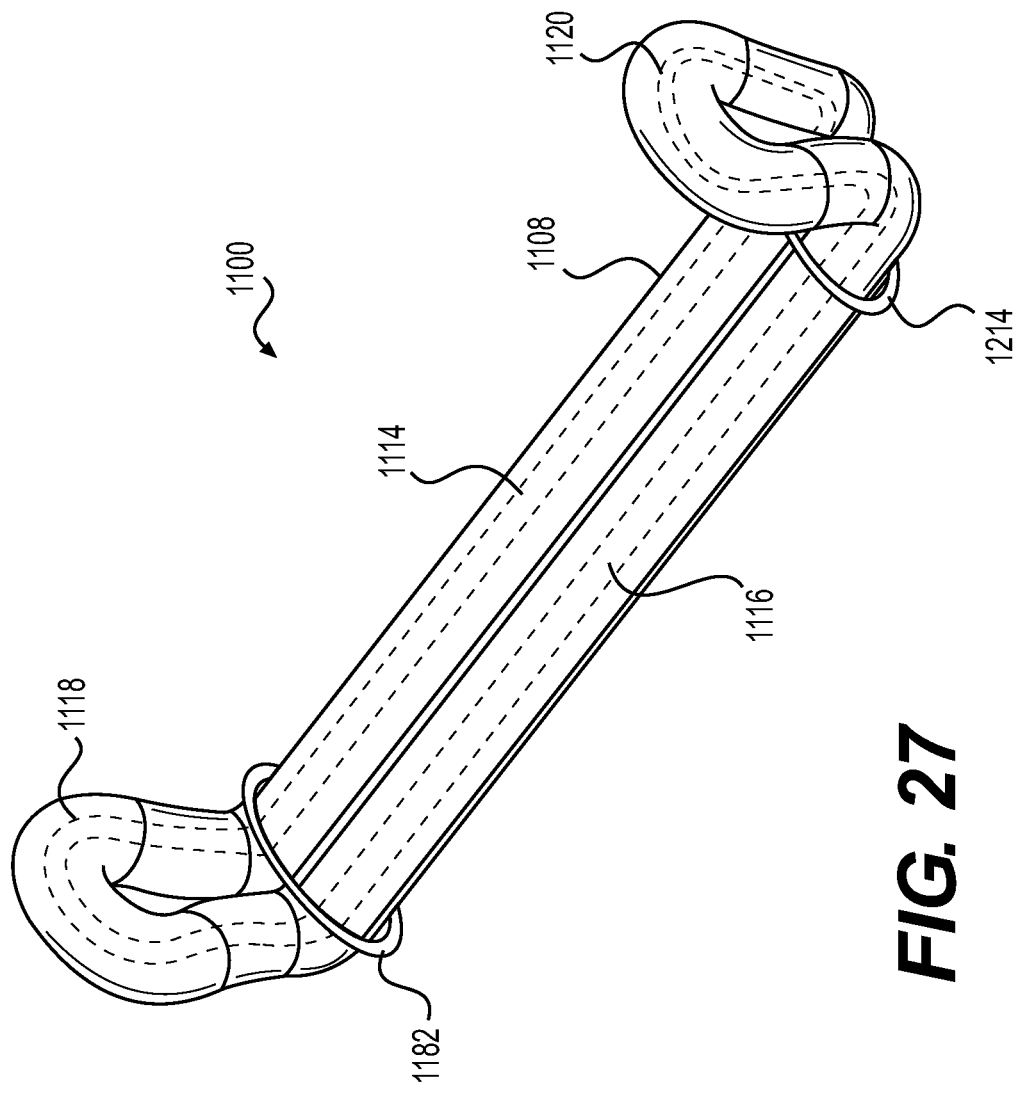
FIG. 27 is an elevated perspective view of an exemplary occlusion clamp in accordance with the present disclosure.
Figure 28:
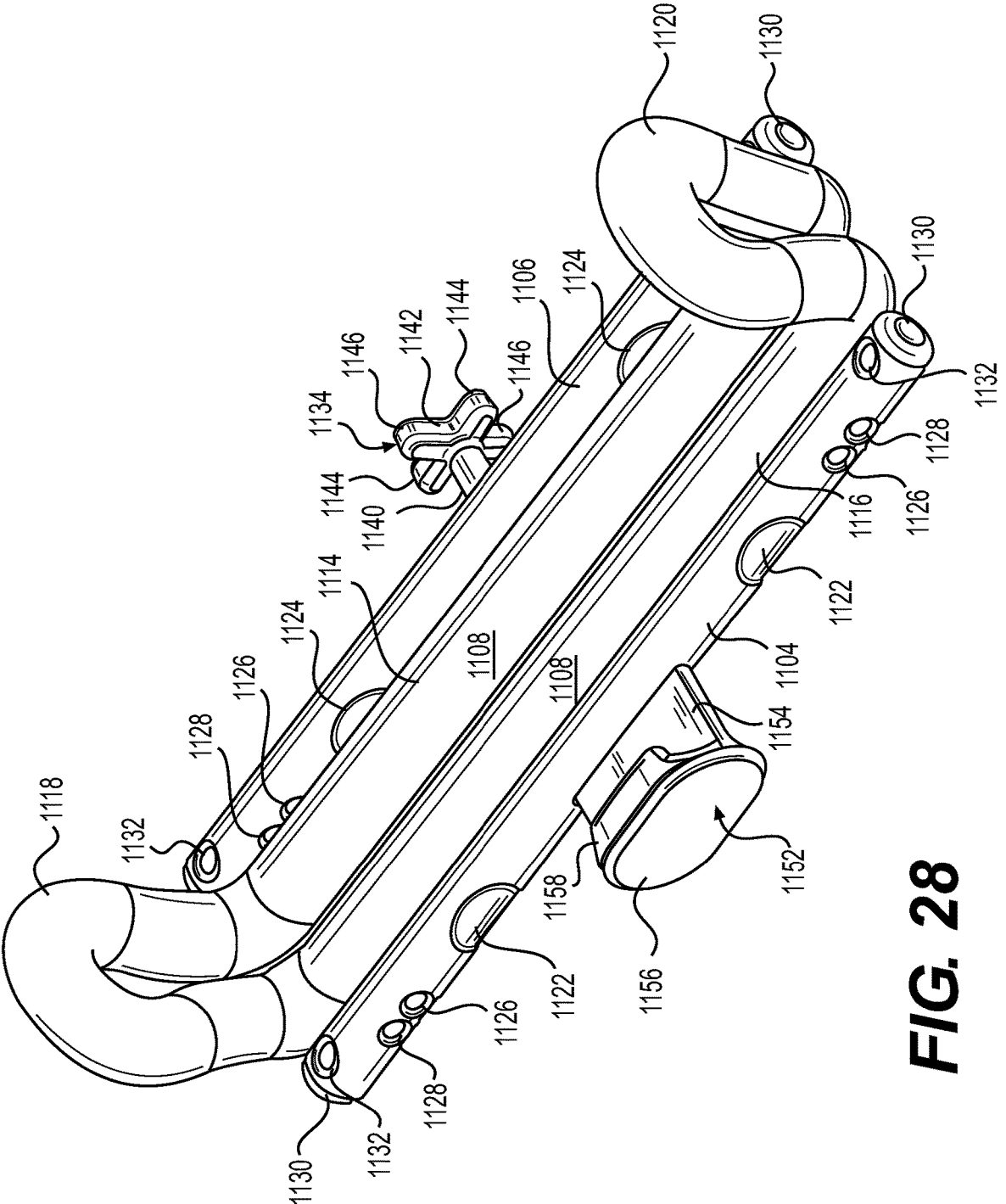
FIG. 28 is an elevated perspective view of the exemplary occlusion clamp of FIG. 1 with a pair of exemplary retainer bars.
Figure 29:
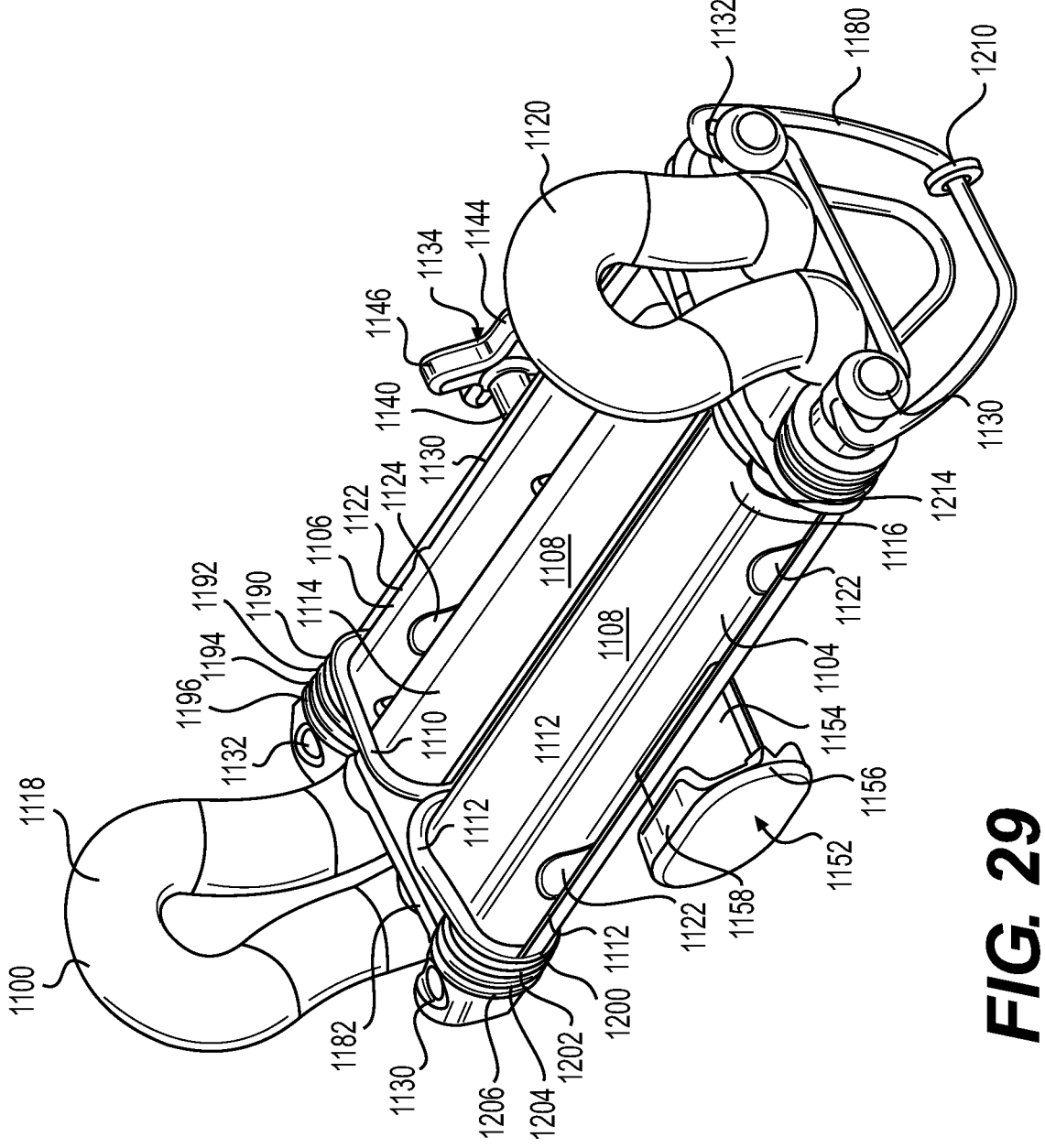
FIG. 29 is an elevated perspective view of the exemplary occlusion clamp and exemplary retainer bars of FIG. 2 being coupled together using sutures.

Referring to FIG. 26, an eleventh exemplary clamp 60K includes pair of plastic retainers 510 that are correspondingly mounted to the tubes 12, 14 on the outside of the fabric covering material 74. In exemplary form, each plastic retainer includes a longitudinal base plate 512 that is mounted to a respective tube 12, 14 using suture bands 514 that concurrently encircle a respective tube and the base plate. Each longitudinal base plate is 512 oriented in parallel with a respective tube 12, 14 to extend outward from the tubes on a lateral side. A series of semicircle loops 516 extend from the base plate and away from the tubes 12, 14 in order to provide a point of attachment for longitudinal shafts 518 that may be grasped by a robotic manipulated or manual end effector (see e.g., FIG. 16, end effector 316A) in order to reposition the shafts away from one another to separate the tubes 12, 14 and open the clamp 60K. In this exemplary embodiment, each base plate 512 includes three semicircle loops 516 that are equally spaced apart from one another. The diameter of the semicircle loops 516 is chosen to match that of the longitudinal shafts 518 so that the shafts are mounted to the retainers using a friction fit between the loops.

Once corresponding longitudinal shafts 518 are coupled to the plastic retainers 510 and separate robotic tools, or manually actuated device designed to fit into these holes, the tools may be repositioned to open and close the clamp 60K. In exemplary form, the longitudinal shafts 518 are moved apart from one another, while remaining in parallel, in order to reposition the plastic retainers 510 and increase the distance therebetween. This repositioning movement of the retainers 510 causes the suture bands 514 to pull on respective tubes 12, 14, thereby increasing the spacing between the tubes and opening the clamp 60K. In contrast, after the clamp 60K is opened, the longitudinal shafts 518 are moved closer to one another, while remaining in parallel, in order to reposition the plastic retainers 510 and decrease the distance therebetween. This repositioning movement of the retainers 510 allows the suture bands 514 be correspondingly repositioned, thereby decreasing the spacing between the tubes 12, 14.

Referencing FIGS. 27-31, an exemplary occlusion clamp 1100, as shown and described in U.S. patent application Ser. No. 11/994,725, filed on Jul. 8, 2008, the disclosure of which is incorporated herein by reference, includes an applicator assembly 1102 in order to reposition and deploy the occlusion clamp. The exemplary applicator assembly 1102 includes a pair of retainer bars 1104, 1106 mounted to a fabric cover material 1108 using sutures 1110, 1112. In this exemplary embodiment, the fabric cover material 1108 may be made of a material such as polyester having been sewn around the clamping portions 1114, 1116 and the urging members 1118, 1120.

Each retainer bar 1104, 1106 includes complementary depressions 1122, 1124 formed into the circumferential surface on opposite sides at two different longitudinal locations. Two primary through holes 1126, 1128 are longitudinally outset from each set of depressions 1122, 1124 and extend perpendicularly through the bars 1104, 1106. The bars 1104, 1106 can contain more or less than two through holes. These primary through holes 1126, 1128 are also centered from side to side with respect to the diameter of the retainer bars 1104, 1106 so that the central axis of each hole intersects the central, longitudinal axis of the retainer bar. More specifically, each primary through hole 1126, 1128 includes complementary top and bottom openings that are on the same sides as the depressions 1122, 1124. In other words, the rounded sides of the retainer bars 1104, 1106 that are offset approximately ninety degrees from the depressions 1122, 1124 are also offset approximately 90 degrees from the top and bottom openings of each primary through hole 1126, 1128. Inset from the ends 1130 of each retainer bar 1104, 1106 are secondary through holes 1132 extending perpendicularly through the bar and are centered from side to side. But these secondary through holes 1132 are perpendicular with respect to, but do not intersect, the primary through holes 1126, 1128. As with the primary through holes 1126, 1128, the secondary through holes 1132 also have opposed top and bottom openings. As will be discussed in more detail below, the holes 1126, 1128 accommodate sutures 1110, 1112 to couple the bars 1104, 1106 to the occlusion clamp 1100.

Figure 30:
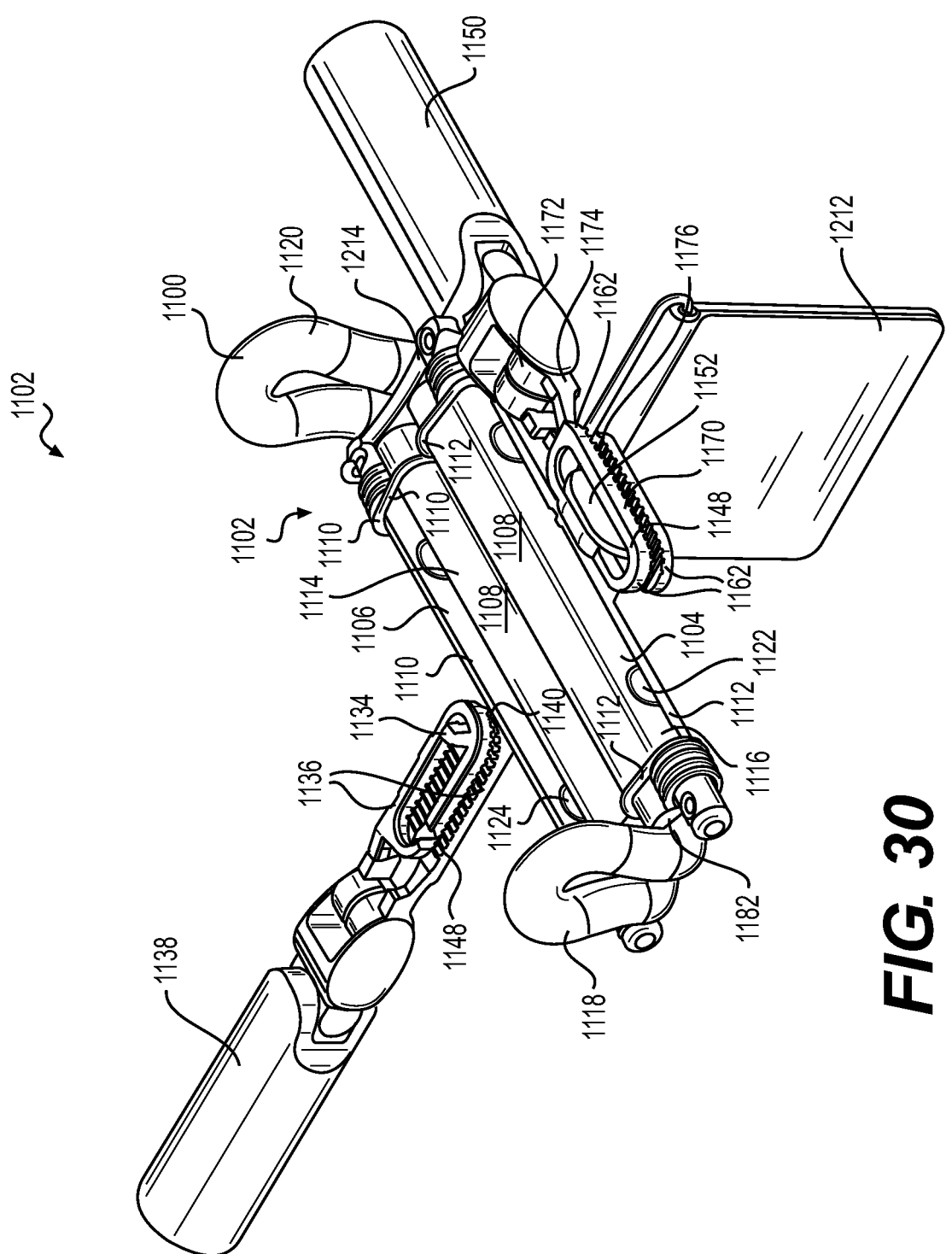
FIG. 30 is an elevated perspective view of an exemplary occlusion clamp and applicator assembly, along with a partial view of pair of robotic devices similar to the robotic device shown in FIG. 16
Figure 31:
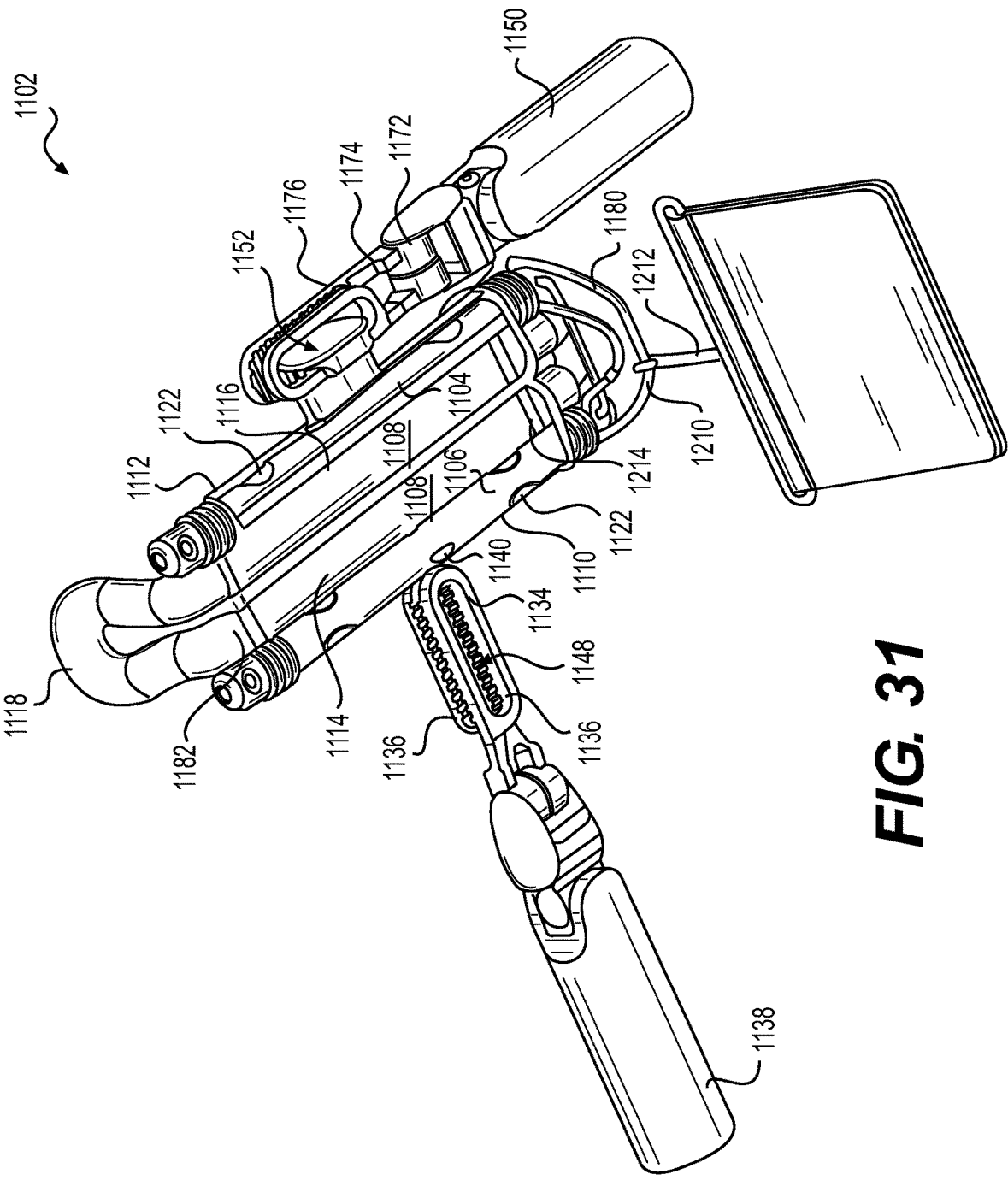
FIG. 31 is an underneath, perspective view of the exemplary occlusion clamp and applicator assembly, along with a partial view of pair of robotic devices, of FIG. 4.

While the retainer bars 1104, 1106 are similar, there are some distinct differences between the two. For example, the retainer bars 1104, 1106 need not be exact compliments or mirrors of each other. In this exemplary embodiment, the second retainer bar 1106 includes a projection 1134 shaped to conform to the jaws 1136 of a first endoscopic grasper 1138. An exemplary endoscopic grasper 1138 that may be used coincident with the applicator assembly 1102 includes, without limitation, the da Vinci surgical system available from Intuitive Surgical, Inc. (www.intuitivesurgical.com/products/davinci_surgicalsystem/index.aspx). This projection 1134 extends perpendicularly away from the retainer bar 1106 in a direction opposite the occlusion clamp 1100. In this exemplary embodiment, the projection 1134 extends from the same side of the retainer bar 1106 as where the depressions 1122 are formed. The projection 1134 includes a cylindrical post 1140 having mounted thereto a crucifix 1142. The crucifix is oriented so that one set of coaxial projections 1144 is parallel to the longitudinal axis of the retainer bar 1106, while a second set of coaxial projections 1146 is perpendicular to the longitudinal axis. The length of the post 1140 allows the jaws 1136 of the endoscopic grasper 1138 to sandwich the first set of coaxial projections 1144, while the second set of coaxial projections 1146 extend through a respective oblong opening 1148 of each endoscopic grasper 1136. In particular, as shown in FIG. 30, the shape of the crucifix 1142 is well suited for gripping by the jaws 1136 and accommodating tension forces when the jaws 1136 are repositioned to open the occlusion clamp 1100 while a second endoscopic grasper 1150 is coupled to the first retainer bar 1104. It should also be noted that the retainer bars 1104, 1106 can be of varying or equivalent cross-sectional geometry.

The first retainer bar 1104 may differ from the second retainer bar 1106 in the shape of its projection 1152. The projection 1152 includes a longitudinal flange 1154 having a perpendicular end plate 1156 that is tapered and rounded over at its ends to form a pair of stops 1158. These stops 1158 generally face the longitudinal flange 1154 and are oriented toward the retainer bar 1104, thereby forming a pair of hooks. In other words, the projection includes a T-shaped cross-section and extends perpendicularly away from the retainer bar 1104 in a generally opposite direction from the other projection 1134. In this exemplary embodiment, the longitudinal flange 1154 is generally rectangular in shape and is dimensioned to allow for gripping by the jaws 1162 of the second endoscopic grasper 1150. An exemplary endoscopic grasper 1150 that may be used coincident with the applicator assembly 1102 includes, without limitation, the da Vinci surgical system available from Intuitive Surgical, Inc. (www.intuitivesurgical.com/products/davinci_surgicalsystem/index.aspx).

By way of example, the jaws 1136, 1162 of the endoscopic graspers 1138, 1150 comprise a pair of individual jaws 1170 pivoting around a common axis. Each jaw 1170 includes a cylindrical base 1172 having a bar 1174 coupled to an oblong frame 1176 extending perpendicularly away from the bar. The oblong frame 1176 outlines the central opening 1148 and is serrated on one side to facilitate gripping. As is shown in the figures, two of the jaws 1170 are stacked upon one another so that the cylindrical bases 1172 are aligned to be coaxial. In an exemplary configuration, the jaws 1170 are oriented so that the oblong openings 1148 overlap one another when the jaws 1136, 1162 are closed. Because of the openings 1148 in the jaws 1170, the jaws are able to receive portions of the projections 1134, 1152 and capable of exerting tensile forces against aspects of the projections in addition to possibly exerting compressive (i.e., gripping) forces on the projections.

Referring back to FIGS. 30 and 31, the end plate 1156 is dimensioned to extend far enough beyond the longitudinal flange 1154 to accommodate the jaws 1162 on opposing sides. Likewise, the height of the stops 1158 and the tapered nature of the stops are dimensioned to pass into the through opening of one of the jaws 1170. As will be discussed in more detail below, the jaws 1162 of the second endoscopic grasper 1150 grip the projection 1152 and pull the projection in a direction generally opposite to the direction of the first endoscopic grasper 1138 pulling on the first projection 1134. This action operates to open the occlusion clamp 1100.

Five distinct sutures 1110, 1112, 1180, 1182, 1214 are utilized as part of the applicator assembly 1102. The first suture 1110 is coupled to the second retainer bar 1106, while the other second suture 1112 is coupled to the first retainer bar 1104. In contrast, the third suture 1180 is concurrently mounted to corresponding near ends of the first retainer 1104 and the second retainer bar 1106. The fourth suture 1182 loosely circumscribes the clamping portions 1114, 1116 and is mounted to at least one of the clamping portions in close proximity to the urging member 1118 using a subordinate suture (not shown). The fifth suture 1214 also loosely circumscribes the clamping portions and is mounted to at least one of the clamping portions in close proximity to the urging member 1120 using a subordinate suture (not shown). Both the fourth and fifth sutures are adapted to remain attached to the clamping portions 1114, 1116 post clamp 1100 deployment. As will be discussed in more detail below, the third suture 1180 is adapted to remain attached to the retainer bars 1104, 1106 in order to withdraw the retainer bars after the occlusion clamp 1100 has been positioned to sandwich the appropriate tissue. Conversely, the first and second sutures are adapted to be severed to disengage the retainer bars 1104, 1106 from the occlusion clamp 1100 post positioning. The cutting zones for severing the sutures are demarcated by the depressions 1122.

In this exemplary embodiment, the manner in which the sutures 1110, 1112 are mounted to the retainer bars 1104, 1106 will now be discussed, starting with the second retainer bar 1106. The second retainer bar 1106 is positioned to be longitudinally parallel with the clamping portion 1114 so the ends of the retainer bar are generally centered along the longitudinal length of the clamping portion 1114. At the same time, the retainer bar 1106 is positioned so that the projection 1134 extends away from the other clamping portion 1114. Likewise, the retainer bar 1106 is positioned so that one opening of each of the primary through holes 1126, 1128 also faces toward the clamping portion 1114 and the second opening of each of the primary holes faces away from the clamping portion. Finally, when the retainer bar 1106 is properly positioned, the first suture 1110 is concurrently attached to the retainer bar and the first clamping portion 1114.

Initially, a predetermined length of suture 1110 is positioned so that its midpoint is generally positioned to be on top of the cylindrical post 1140 of the projection 1134, with the suture being extended longitudinally to lie in parallel with the clamping portion 1114. In this position, the suture 1110 lies on top of the retainer bar 1106 so that that suture extends across the top depressions 1122. Each end of the suture 1110 is then threaded through the nearest 1126 of the primary holes so that the suture lies across the nearest of the two clamping portions 1114, 1116 (in this case, clamping portion 1114). The ends of the suture 1110 are then looped around the clamping portion 1114 and then threaded through the farthest 1128 of the primary holes and drawn taught. In this manner, the suture 1110 has circumscribed the outside of the clamping portion 1114. After the suture 1110 is drawn taught, having been threaded through the farthest 1128 of the primary holes, a first half hitch knot 1190 is tied. Thereafter, a second 1192 and a third 1194 half hitch knots are tied in the ends of the suture 1110 toward the ends of the retainer bar 1106. After the three hitch knots are tied, the ends of the suture 1110 are then utilized to tie a timberline knot 1196, with any excess suture being removed at the end of the timberline knot. Methods of knot tying can be found in numerous resources, as can many types of knots that may be used to secure the retainer bars 1104, 1106 to the occlusion clamp 1100 using sutures 1110, 1112.

An adhesive may be placed on the knots 1190, 1192, 1194, 1196 to secure the knots and eliminate or limit fraying and migration. Alternative methods of knot tying or retainer bar design may eliminate or decrease utilization of adhesives on the knots. For example, a compressive or constriction type of knot may also be used to secure the suture to the bar 1104, 1106. In addition, or in the alternative, heat staking or other methods of combining, lapping, and/or fixating suture-to-suture, suture-to-metal, or suture-to-plastic may be used. When the knots 1190, 1192, 1194, 1196 are completed, the suture 1110 is generally taught around the retainer bar 1106 and clamping portion 1114 so that pulling on the retainer bar 1106 away from the clamping portion 1114 is operative to reposition the clamping portion 1114.

The foregoing process is generally repeated for the first retainer bar 1104 by positioning the retainer bar to be longitudinally parallel with the first clamping portions 1116 so the ends of the retainer bar are generally centered along the longitudinal length of the clamping portion 1116. At the same time, the retainer bar 1104 is positioned so that the projection 1152 extends away from the clamping portion 1116. Likewise, the retainer bar 1104 is positioned so that one opening of each of the primary through holes 1126, 1128 also faces toward the clamping portion 1116 and a second opening of each of the primary holes faces away from the clamping portions. Finally, when the retainer bar 1104 is properly positioned, the second suture 1112 is attached using the following process.

Initially, a predetermined length of suture 1112 is positioned so that its midpoint is generally positioned to be on top of the longitudinal flange 1154 of the projection 1152, with the suture being extended longitudinally to lie in parallel with the clamping portion 1116. In this position, the suture 1112 lies on top of the retainer bar 1104 so that that suture extends across the top depressions 1122. Each end of the suture 1112 is then threaded through the nearest 1126 of the primary holes so that the suture lies across the nearest of the two clamping portions 1114, 1116 (in this case, clamping portion 1116). The ends of the suture 1112 are then looped around the clamping portion 1116 and then threaded through the farthest 1128 of the primary holes and drawn taught. In this manner, the suture 1112 has circumscribed the outside of the clamping portion 1116. After the suture 1112 is drawn taught, having been threaded through the farthest 1128 of the primary holes, a first half hitch knot 1200 is tied. Thereafter, a second 1202 and a third 1204 half hitch knots are tied in the ends of the suture 1112 toward the ends of the retainer bar 1104. After the three hitch knots are tied, the ends of the suture 1112 are then utilized to tie a timberline knot 1206, with any excess suture being removed at the end of the timberline knot. When the knots are completed, the suture 1112 is generally taught around the retainer bar 1104 and clamping portion 1116 so that pulling on the retainer bar 1104 away from the clamping portion 1116 is operative to reposition the clamping portion 1116.

In this exemplary embodiment, the manner in which the suture 1180 is mounted to the retainer bars 1104, 1106 will now be discussed. The first retainer bar 1104 and the second retainer bar 1106 each include a secondary through hole 1132 located proximate each longitudinal end. These through holes 1132 are adapted to receive predetermined lengths of suture 1180 in order to couple the retainer bars 1104, 1106 to one another. As will be discussed in more detail below, the suture 1180 is not adapted to be severed, but instead remains coupled to the retainer bars 1104, 1106 after the sutures 1110, 1112 are severed to remove the retainer bars 1104, 1106 and remaining sutures 1110, 1112 attached to the retainer bars subsequent to deployment of the occlusion clamp 1100.

In exemplary form, the third suture 1180 is threaded through one of the secondary through holes 1132 of the second retainer bar 1106 so that the end of the suture extending from the opening nearest the urging member 1120 is wrapped around the outside of the retainer bar 1106 (and held in position) and is in proximity to the other end of the suture 1180 exiting the opening facing away from the urging member 1120. The end of the suture 1180 exiting the opening that faces away from the urging member 1120 travels across the ends of the two clamping portions 1114, 1116 and is threaded into the an opening of the nearest secondary through hole 1132 of the first retainer bar 1104, where the opening faces away from the urging member 1120. When the suture 1180 is threaded into this through hole 1132, the end of the suture 1180 travels through the hole 1132 and exits nearer to the urging member 1120. This free end 1180 is then looped around the outside of the first retainer bar 1104 and meets the other end of the suture 1180 that was previously held in position to create a knot 1210 to close the third suture 1180, thereby forming a closed loop. In this exemplary embodiment, the third suture 1180 loop is coupled to a tab 1212 that provides a quickly apparent attachment point for one of the endoscopic graspers 1138, 1150 to grasp and withdraw the remaining sutures and retainer bars 1104, 1106 after the occlusion clamp 1100 is deployed.

The fourth and fifth sutures 1182, 1214 are respectively loosely looped around the two clamping portions 1114, 1116 proximate the urging members 1118, 1120. A subordinate suture (not shown) is used to couple the sutures 1182, 1214 to the fabric cover material 1108. In exemplary form, the length of the sutures 1182, 1214 is chosen to that when taught, the sutures operate to limit the travel of the clamping portions 1114, 1116. In other words, the sutures 1182, 1214 constrain just how far apart the clamping portions 1114, 1116 may be repositioned. It should be noted that the sutures may or may not be removed post occlusion clamp 1100 deployment.

An exemplary deployment of the occlusion clamp 1100 using the applicator assembly 1102 presumes the sutures 1110, 1112 have been attached to the retainer bars 1104, 1106 as discussed above. Likewise, the exemplary deployment explanation also presumes that the sutures 1180, 1182, 1214 have been respectively attached to the retainer bars and the clamping portions 1114, 1116. In exemplary form, deployment of the occlusion clamp 1100 in a surgical procedure includes positioning the clamp in proximity to tissue to be clamped. Exemplary tissue that may be clamped by the occlusion: clamp 1100 includes, without limitation, the left atrial appendage of the heart. After the clamp 1100 has been introduced proximate the tissue to be occluded, the endoscopic graspers 1138, 1150 are utilized to grasp the applicator assembly 1102 in order to more precisely position the clamp 1100.

Specifically, the jaws 1136 of the first endoscopic grasper 1138 are opened so that the openings 1148 of each jaw overlap the coaxial projections 1146 of the crucifix 1142 and are thereafter shut or brought closer together to grasp the coaxial projections 1144. In such an orientation, the jaws 1136 of the endoscopic grasper 1138 are able to pull on the crucifix 1142 in a direction opposite, and coaxial with, the longitudinal direction of the cylindrical post 1140. Concurrently, the jaws 1162 of the second endoscopic grasper 1150 are opened and oriented so that the openings 1148 completely overlap the end plate 1156 and stops 1158. Thereafter, the jaws 1162 are shut or brought closer together to grasp the longitudinal flange 1154 of the projection 1152. It should be noted that when the openings of the jaws 1162 are oriented to completely overlap the end plate 1156 and stops 1158, this orientation coincides with the second endoscopic grasper 1150 being oriented generally in parallel with the first retainer bar 1104. After the endoscopic graspers 1138, 1150 have been positioned to grasp the projections 1134, 1152, the endoscopic graspers are repositioned to open the clamp 1100.

By way of example, the second endoscopic grasper 1150 may remain stationary, while the first endoscopic grasper 1138 pulls on the projection 1134 in a direction away from the clamp 1100. This force mustered by the endoscopic graspers 1138, 1150 working in tandem is greater than the spring force associated with the urging members 1118, 1120, which results in the clamping portions 1114, 1116 being repositioned to create a gap therebetween. While this gap is maintained, using the relative position of the endoscopic graspers 1138, 1150, the clamp 1100 is repositioned so that the tissue to be occluded is directed between the clamping portions 1114, 1116. After the tissue is placed between the clamping portions 1114, 1116 to the satisfaction of the surgeon, the endoscopic graspers 1138 are repositioned toward one another so that the spring force of the clamping portions 1114, 1116 is applied to the tissue in question. Thereafter, surgical snips (not shown) are introduced, while the clamp 1100 is positioned to clamp the tissue in question, to sever the sutures 1110, 1112. Specifically, the snips are introduced proximate the depressions 1122 on each of the retainer bars 1104, 1106 to sever the sutures 1110, 1112, thereby creating a new pair of free ends for each suture. But it should be noted that the sutures 1180 remain, thereby linking the retainer bars 1104, 1106 to one another. It is the new free ends of the sutures 1110, 1112 that discontinue the sutures being taught and the coupling between the retainer bars 1104, 1106 and the clamping portions 1114, 1116. In this manner, a surgeon grasps the tab 1212 and pulls the retainer bars 1104, 1106 from the surgical region and the clamp 300. Because the tab 1212 remains attached to the retainer bars 1104, 1106 by way of the suture 1180, and because the sutures 1110, 1112 remain attached to the retainer bars by way of the knots 1190, 1192, 1194, 1196, 1200, 1202, 1204, 1206, pulling on the tab 1212 removes concurrently removes the retainer bars and the sutures. In exemplary form, the tab 1212 is adapted to be positioned at all times outside of the body cavity.

The foregoing components may be fabricated from any surgical grade material. By way of example, the retainer bars

1104, 1106 are fabricated from a metal, such as stainless steel, aluminum, or titanium, while the sutures can be obtained commercially available from Ethicon (J&J) or fabricated for use. Whilst not necessary to use adhesive on the knots, a person skilled in knot tying may create a compressive or constrictive type of knot in order to eliminate or reduce the amount of adhesive. Adhesives for use with the foregoing exemplary embodiments may include CA, UV-CA, or other medical or non-medical grade adhesives. The projections can be of similar geometry or differing geometries. The retainer bars 1104, 1106 can be of varying or equivalent cross-sectional geometries, as well as have the same or differing projections 1134, 1152. For example, the retainer bars 1104, 1106 may both include the same projection 1134 or the same projection 1152.

Figure 32:
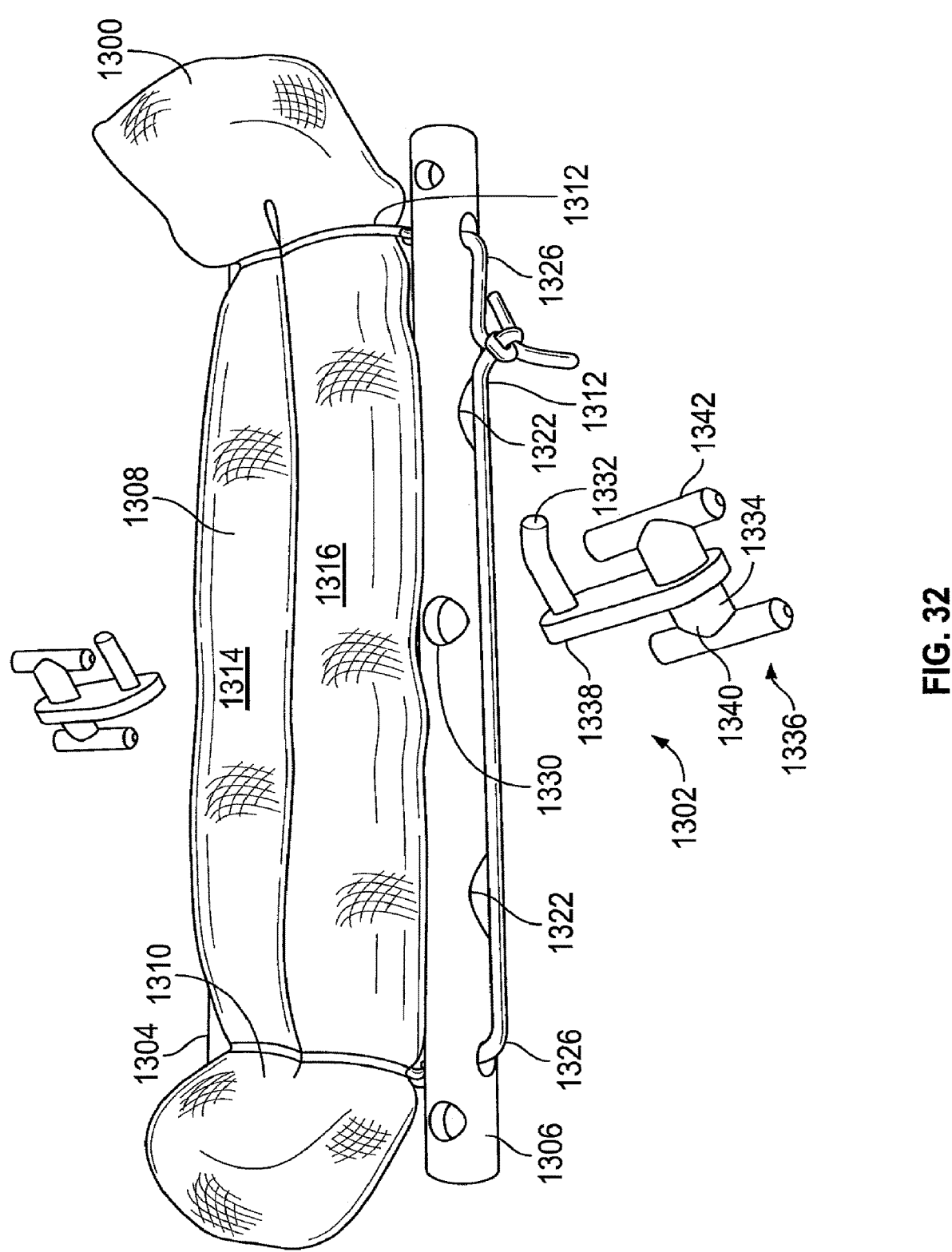
FIG. 32 is an elevated perspective view of the exemplary occlusion clamp and another exemplary applicator assembly.

Referring to FIG. 32, an alternate exemplary occlusion clamp 1300, as shown and described in U.S. patent application Ser. No. 11/994,725, filed on Jul. 8, 2008, the disclosure of which is incorporated herein by reference, includes an applicator assembly 1302 in order to reposition and deploy the occlusion clamp. The exemplary applicator assembly 1302 includes a pair of retainer bars 1304, 1306 mounted to a fabric cover material 1308 using sutures 1310, 1312. In this exemplary embodiment, the fabric cover material 1308 may be made of a material such as polyester having been sewn around the clamping portions 1314, 1316 and the urging members.

Each retainer bar 1304, 1306 includes complementary depressions 1322 formed into the circumferential surface on opposite sides at two different longitudinal locations. A primary through holes 1326 is longitudinally outset from each set of depressions 1322 and extend perpendicularly through the bars 1304, 1306 and are adapted to receive the sutures 1310, 1312 that concurrently couple the respective retainer bars 1304, 1306 to one of the clamping portions 1314, 1316.

In this exemplary embodiment, each retainer bar 1304, 1306 includes a central opening or through hole 1330 that accepts a hook 1332 of a removable hitch 1334. The removable hitch 1334, in this exemplary embodiment, includes a pair of T-shaped projections 1336 extending from opposite sides of a hitch plate 1338. In exemplary form, the hook 1332 is mounted proximate a first end of the hitch plate 1338 and is curved toward the T-shaped projections 1336 that are mounted proximate a second, opposite end of the hitch plate. More specifically, the T-shaped projections 1336 include a base portion 1340 perpendicularly extending from the hitch plate 1338, and a pair of arms 1342 that perpendicularly extend from the base portion in opposite directions. By way of example, the arms are oriented to be generally perpendicular with a respective retainer bar 1304, 1306 when the hitch 1334 is coupled to a retainer bar.

The removable hitch 1334 is adapted to be grasped by a manual or robotic end effector, such as those described herein (See end effector 316A is available from Intuitive Surgical, Inc. of Mountain View, Calif as the ProGrasp Forceps (www.intuitivesurgical.com)). In this fashion, the end effector grips at least one of the T-shaped projections 1336 and repositions the hitch 1334 so that the hook 1332 is received within a through hole 1330 of a respective retainer bar 1304, 1306. Thereafter, the end effector may be repositioned to correspondingly reposition the hitch 1334 in a direction where the hook 1332 pulls against the portion of the retainer bar 1304/1306 defining the through hole 1330 and thereby pulls a respective clamping portion 1314/1316 in the same direction that the end effector is being pulled.

Specifically, it is envisioned that a pair of end effectors are utilized in conjunction with a pair of hitches 1334, thereby providing a means to reposition the retainer bars 1304, 1306 and the clamping portion 1314, 1316 by repositioning the end effectors in generally opposite directions. In exemplary form, each end effector grasps a separate hitch 1334 and repositions each hitch so that its hook 1332 is received within a separate through hole 1330 of a respective retainer bar 1304, 1306. Thereafter, the end effectors are pulled in generally opposite directions to overcome the bias exerted by the clamping portions 1314, 1316 in order to open the clamping portions (i.e., create a gap or large gap between the clamping portions). After the clamping portions 1314, 1316 have been opened, the tissue to be occluded is oriented between the clamping portions.

After the tissue to be occluded has been positioned between the open clamping portions 1314, 1316, the applicator assembly 1302 is removed from the clamp 1300. In exemplary form, the end effectors may be repositioned toward one another, thereby allowing the biased clamping portions 1314, 1316 to sandwich the tissue to be occluded. Thereafter, the sutures 1310, 1312 are severed by positioning snips (not shown) proximate the depressions 1322 to discontinue the coupling between the clamping portions 1314, 1316 and the retainer bars 1304, 1306. At this point, the end effectors may be utilized to remove the retainer bars 1304, 1306 using the hitches 1334. Specifically, the hooks 1332 of each hitch 1334 remain engaged with the retainer bars 1304, 1306 so that movement of the hitch results in corresponding movement of the retainer bars.

Figure 33:
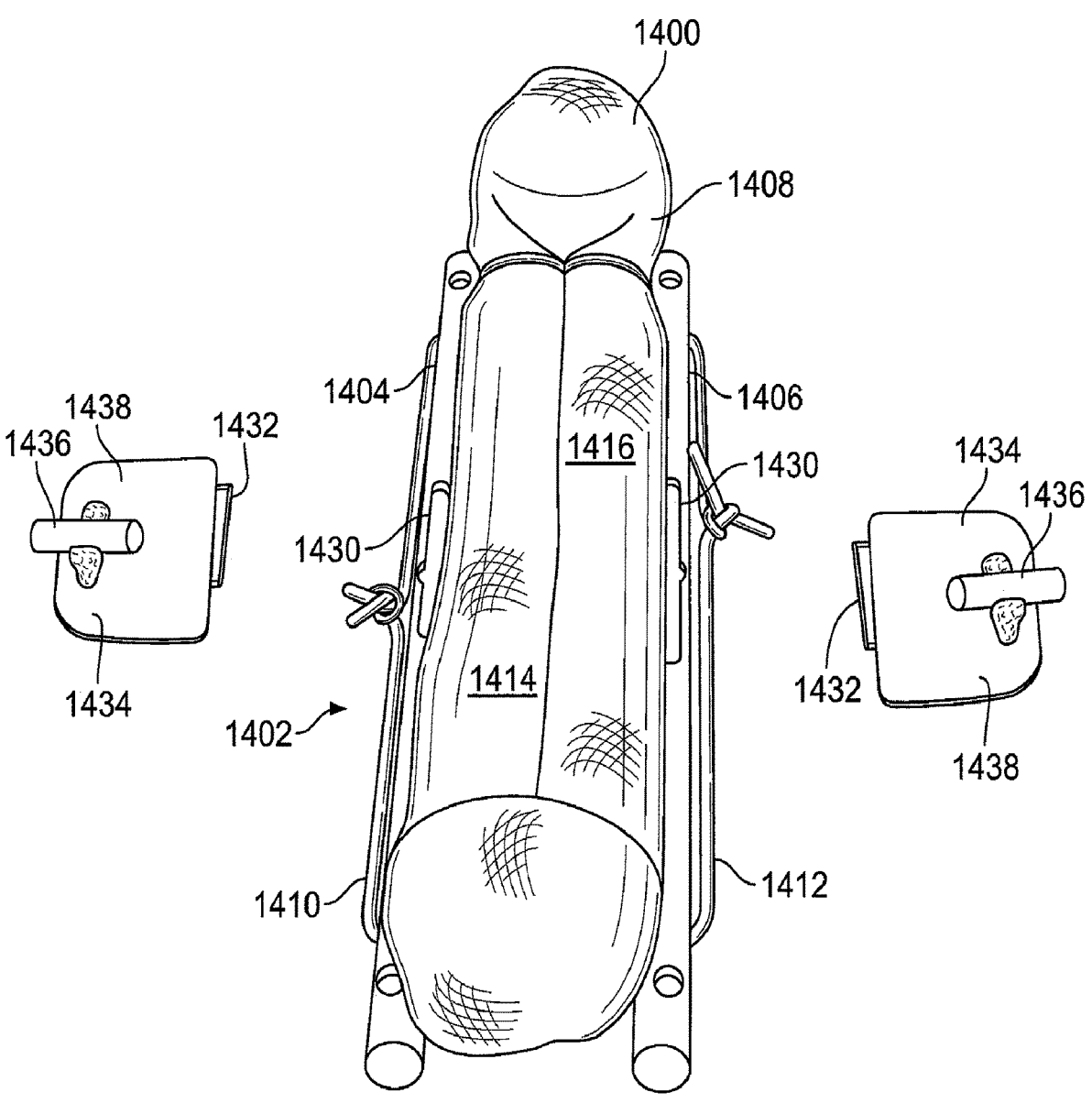
FIG. 33 is an elevated perspective view of the exemplary occlusion clamp and a further exemplary applicator assembly.

Referring to FIG. 33, another alternate exemplary occlusion clamp 1400, as shown and described in U.S. patent application Ser. No. 11/994,725, filed on Jul. 8, 2008, the disclosure of which is incorporated herein by reference, includes an applicator assembly 1402 in order to reposition and deploy the occlusion clamp. The exemplary applicator assembly 1402 includes a pair of retainer bars 1404, 1406 mounted to a fabric cover material 1408 using sutures 1410, 1412. In this exemplary embodiment, the fabric cover material 1408 may be made of a material such as polyester having been sewn around the clamping portions 1414, 1416 and the urging members.

Each retainer bar 1404, 1406 includes complementary depressions formed into the circumferential surface on opposite sides at two different longitudinal locations. Two primary through holes are longitudinally outset from each set of depressions and extend perpendicularly through the bars 1404, 1406 and are adapted to receive the sutures 1410, 1412 that concurrently couple the respective retainer bars 1404, 1406 to one of the clamping portions 1414, 1416.

In this exemplary embodiment, each retainer bar 1404, 1406 includes a longitudinal channel 1430 that accepts a flange 1432 of a removable hitch 1434. The removable hitch 1434, in this exemplary embodiment, includes a pair of T-shaped projections 1436 extending from opposite sides of a hitch plate 1438. In exemplary form, the flange 1432 is mounted proximate a first end of the hitch plate 1438, while the T-shaped projections 1436 are mounted proximate a second, opposite end of the hitch plate. More specifically, the T-shaped projections 1436 include a base portion perpendicularly extending from the hitch plate 1438, and a pair of arms that perpendicularly extend from the base portion in opposite directions. By way of example, the arms are oriented to be generally perpendicular with a respective retainer bar 1404, 1406 when the hitch 1434 is coupled to a retainer bar.

The removable hitch 1434 is adapted to be grasped by a manual or robotic end effector, such as those described herein (See end effector 316A is available from Intuitive Surgical, Inc. of Mountain View, Calif as the ProGrasp Forceps (www.intuitivesurgical.com)). In this fashion, the end effector grips at least one of the T-shaped projections 1436 and repositions the hitch 1434 so that the flange 1432 is received within a longitudinal channel 1430 of a respective retainer bar 1404, 1406. Thereafter, the end effector may be repositioned to correspondingly reposition the hitch 1434 in a direction where the flange 1432 pulls against the portion of the retainer bar 1404/1406 defining the longitudinal channel 1430 and thereby pulls a respective clamping portion 1414/1416 in the same direction that the end effector is being pulled.

Specifically, it is envisioned that a pair of end effectors are utilized in conjunction with a pair of hitches 1434, thereby providing a means to reposition the retainer bars 1404, 1406 and the clamping portion 1414, 1416 by repositioning the end effectors in generally opposite directions. In exemplary form, each end effector grasps a separate hitch 1434 and repositions each hitch so that its flange 1432 is received within a separate longitudinal channel 1430 of a respective retainer bar 1404, 1406. Thereafter, the end effectors are pulled in generally opposite directions to overcome the bias exerted by the clamping portions 1414, 1416 in order to open the clamping portions (i.e., create a gap or large gap between the clamping portions). After the clamping portions 1414, 1416 have been opened, the tissue to be occluded is oriented between the clamping portions.

After the tissue to be occluded has been positioned between the open clamping portions 1414, 1416, the applicator assembly 1402 is removed from the clamp 1400. In exemplary form, the end effectors may be repositioned toward one another, thereby allowing the biased clamping portions 1414, 1416 to sandwich the tissue to be occluded. Thereafter, the sutures 1410, 1412 are severed by positioning snips (not shown) proximate the depressions 1422 to discontinue the coupling between the clamping portions 1414, 1416 and the retainer bars 1404, 1406. At this point, the end effectors may be utilized to remove the retainer bars 1404, 1406 using the hitches 1434. Specifically, the flanges 1432 of each hitch 1434 remain engaged with the retainer bars 1404, 1406 so that movement of the hitch results in corresponding movement of the retainer bars.

Following from the above description and invention summaries, it should be apparent to those of ordinary skill in the art that, while the methods and apparatuses herein described constitute exemplary embodiments of the present invention, the invention is not limited to the foregoing and changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A left atrial appendage occlusion device comprising:
a first beam and a second beam biased toward one another by a first spring coupled thereto, wherein the first and second beams are covered by a fabric, the fabric coupled to a first fabric pocket and a second fabric pocket, wherein the first fabric pocket extends parallel to a longitudinal axis of the first beam and the second fabric pocket extends parallel to a longitudinal axis of the second beam so the first fabric pocket and the second fabric pocket are interposed by the first beam, the second beam, and the fabric covering the first beam and the second beam, and wherein each of the first fabric pocket and the second fabric pocket is peripherally enclosed along its longitudinal length to delineate a longitudinal cavity open on at least one longitudinal end.

2. The occlusion device of claim 1, wherein each of the first and second beams receives a portion of the first spring.

3. The occlusion device of claim 1, wherein the first and second fabric pockets are permanent.

4. The occlusion device of claim 1, wherein a length of the first fabric pocket is less than a length of the first beam.

5. The occlusion device of claim 4, wherein a length of the second fabric pocket is less than a length of the second beam.

6. The occlusion device of claim 1, wherein the first and second beams each comprise a load spreading platen.

7. The occlusion device of claim 1, further comprising a deployment device removably coupled to each of the first and second fabric pockets.

8. The occlusion device of claim 7, wherein the deployment device is configured to transition the left atrial appendage occlusion device from a closed position to an open position.

9. The occlusion device of claim 7, wherein the deployment device includes a first shaft configured to be removably received within the first fabric pocket, and a second shaft configured to be removably received within the second fabric pocket.

10. A left atrial appendage occlusion device comprising:
a first beam and a second beam biased toward one another by a pair of U-shaped springs, wherein each of the first beam and the second beam comprises a permanent pocket extending parallel to a longitudinal axis of at least one of the first beam and the second beam, and wherein each permanent pocket includes an open, first longitudinal end and a closed, second longitudinal end peripherally bounded therebetween to delineate a longitudinal cavity configured to receive a repositionable shaft for repositioning the first beam with respect to the second beam.

11. The occlusion device of claim 10, wherein each of the first and second beams receives a portion of each of the pair of U-shaped springs.

12. The occlusion device of claim 10, wherein the pair of U-shaped springs are parallel to one another.

13. The occlusion device of claim 10, wherein a length of at least one of the permanent pockets is less than a length of the first beam.

14. The occlusion device of claim 10, wherein a length of each of the permanent pockets is less than a length of the first beam.

15. The occlusion device of claim 10, wherein each of the first beam and the second beam comprises a load spreading platen.

16. The occlusion device of claim 10, further comprising a deployment device removably coupled to each of the first beam and the second beam.

17. The occlusion device of claim 16, wherein the deployment device includes a pair of repositionable shafts configured to be received within the permanent pockets, wherein the pair of repositionable shafts are configured to move apart from one another to reposition the occlusion device from a closed position to an open position.

18. A left atrial appendage occlusion device comprising:
a first beam and a second beam biased toward one another using a first spring, wherein the first beam and the second beam are covered by a fabric, and a first fabric pocket is sewn along its longitudinal length to the fabric covering the first beam, and a second fabric pocket is sewn along its longitudinal length to the fabric covering the second beam, wherein the first fabric pocket has a dominant longitudinal dimension extending parallel to a longitudinal axis of the first beam and the second fabric pocket has its own dominant longitudinal dimension extending parallel to a longitudinal axis of the second beam, and wherein a majority of the dominant longitudinal dimension of each of the first and second constituent pockets is peripherally enclosed to delineate a longitudinal cavity open at one longitudinal end.

19. The occlusion device of claim 18, wherein a length of the first fabric pocket is less than a length of the first beam, and a length of the second fabric pocket is less than a length of the second beam.

20. The occlusion device of claim 18, further comprising a deployment device removably coupled to each of the first beam and the second beam, wherein the deployment device includes a first shaft configured to be received within the first fabric pocket, and a second shaft configured to be received within the second fabric pocket, wherein the first shaft is repositionable with respect to the second shaft when the first and second shafts are received within the first and second fabric pockets in order to reposition the occlusion device from a closed position to an open position.

* * * * *